US012570652B2

(12) United States Patent
Gu et al.

(10) Patent No.: US 12,570,652 B2
(45) Date of Patent: Mar. 10, 2026

(54) PYRROLIDINE COMPOUND AND USE THEREOF

(71) Applicants: SIMCERE PHARMACEUTICAL CO., LTD., Jiangsu (CN); JIANGSU SIMCERE PHARMACEUTICAL CO., LTD., Jiangsu (CN)

(72) Inventors: Peng Gu, Shanghai (CN); Lei Liu, Shanghai (CN); Guobao Zhang, Shanghai (CN); Feng Zhou, Shanghai (CN); Renhong Tang, Shanghai (CN); Jinsheng Ren, Shanghai (CN)

(73) Assignees: SIMCERE PHARMACEUTICAL CO., LTD., Jiangsu (CN); JIANGSU SIMCERE PHARMACEUTICAL CO., LTD., Jiangsu (CN)

( * ) Notice: Subject to any disclaimer, the term of this patent is extended or adjusted under 35 U.S.C. 154(b) by 624 days.

(21) Appl. No.: 17/925,102

(22) PCT Filed: May 14, 2021

(86) PCT No.: PCT/CN2021/093736
§ 371 (c)(1),
(2) Date: Nov. 14, 2022

(87) PCT Pub. No.: WO2021/228210
PCT Pub. Date: Nov. 18, 2021

(65) Prior Publication Data

US 2023/0348459 A1 Nov. 2, 2023

(30) Foreign Application Priority Data

May 15, 2020 (CN) ......................... 202010414013.9

(51) Int. Cl.
*C07D 471/04* (2006.01)
*A61P 35/00* (2006.01)

(52) U.S. Cl.
CPC ............ *C07D 471/04* (2013.01); *A61P 35/00* (2018.01)

(58) Field of Classification Search
CPC .............................. A61P 35/00; C07D 471/04
See application file for complete search history.

(56) References Cited

U.S. PATENT DOCUMENTS

| | | | |
|---|---|---|---|
| 9,855,270 | B2 | 1/2018 | Hager et al. |
| 2011/0190246 | A1 | 8/2011 | Blume et al. |
| 2016/0175289 | A1 | 6/2016 | Labadie et al. |
| 2018/0111931 | A1 | 4/2018 | Barlaam et al. |
| 2018/0291019 | A1 | 10/2018 | Guan et al. |
| 2022/0204488 | A1 | 6/2022 | Bouaboula et al. |

FOREIGN PATENT DOCUMENTS

| | | | | | |
|---|---|---|---|---|---|
| CN | 102105484 | A | | 6/2011 | |
| CN | 106488767 | A | | 3/2017 | |
| CN | 107108611 | A | * | 8/2017 | ........... A61K 31/565 |
| CN | 107428758 | A | | 12/2017 | |
| CN | 109963848 | A | | 7/2019 | |
| JP | 2017-538725 | A | | 12/2017 | |
| JP | 2019-537570 | A | | 12/2019 | |
| JP | 2020-502060 | A | | 1/2020 | |
| WO | WO-2016097072 | A1 | * | 6/2016 | ........... A61K 31/565 |
| WO | 2017/216279 | A1 | | 12/2017 | |
| WO | 2018001232 | A1 | | 1/2018 | |
| WO | 2018077630 | A1 | | 5/2018 | |
| WO | WO-2018091153 | A1 | * | 5/2018 | .............. A61P 43/00 |
| WO | 2019/002442 | A1 | | 1/2019 | |
| WO | 2019223715 | A1 | | 11/2019 | |
| WO | 2019245974 | A1 | | 12/2019 | |

OTHER PUBLICATIONS

Johnson et al., (British J. of Cancer 2001, p. 1424-1431) (Year: 2001).*
Gura et al. (Science 1997, Nov 7, 278) (Year: 1997).*
Neidle, Stephen, ed., Cancer Drug Design and Discovery:(Elsevier/Academic Press, 2008) (Year: 2008).*
Cecil Textbook of Medicine, 20th Edition, vol. 1, 1996 (Year: 1996).*
Cecil reference (Cecil Textbook of Medicine, 2000) (Year: 2000).*
CN107108611A- English translation (Year: 2017).*
Chen, Frontiers in Endocrinology, 2022 (Year: 2022).*
Office Action (The First Office Action) issued Aug. 26, 2024, by the State Intellectual Property Office of People's Republic of China in corresponding Chinese Patent Application No. 202180035358.6 and an English translation of the Office Action. (21 pages).

(Continued)

*Primary Examiner* — Umamaheswari Ramachandran
(74) *Attorney, Agent, or Firm* — Buchanan Ingersoll & Rooney PC

(57) ABSTRACT

Disclosed are a pyrrolidine compound as represented by formula (I) or a pharmaceutically acceptable salt thereof, a pharmaceutical composition containing same, and the use of the pharmaceutical composition as a selective estrogen receptor degrader (SERD) in the prevention or treatment of estrogen receptor-related diseases.

(I)

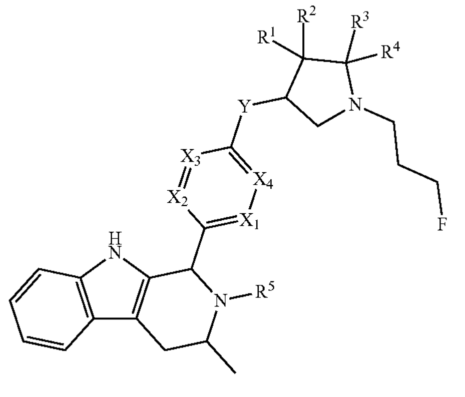

12 Claims, 3 Drawing Sheets

(56) References Cited

OTHER PUBLICATIONS

Office Action (The Second Office Action) issued Feb. 6, 2025, by the State Intellectual Property Office of People's Republic of China in corresponding Chinese Patent Application No. 202180035358.6 and an English translation of the Office Action. (28 pages).

Office Action (Notice of Reasons for Refusal) issued Jan. 28, 2025, by the Japan Patent Office in corresponding Japanese Patent Application No. 2023-513900 and an English translation of the Office Action. (6 pages).

International Search Report issued in PCT Application No. PCT/CN2021/093736, mailed Jul. 29, 2021, 8 pages.

Nathan et al., A Review of Fulvestrant in Breast Cancer, Oncol. Ther. (2017) 5:17-19, 13 Pages.

Patel et al., Selective Estrogen Receptor Modulators (SERMs) and Selective Estrogen 3 Receptor Degraders (SERDs) in Cancer, Pharmacology and Therapeutics 186 (2018), 128 Pages.

* cited by examiner

PYRROLIDINE COMPOUND AND USE THEREOF

CROSS REFERENCE TO RELATED APPLICATIONS

This application is a U.S. National Phase Application of PCT International Application No. PCT/CN2021/093736, filed May 14, 2021, which claims the right of priority for the prior application with the patent application number of CN202010414013.9, entitled "Pyrrolidine Compound and Use Thereof" and submitted to the China National Intellectual Property Administration on 15 May, 2020. The above-mentioned prior applications are incorporated into the present application by reference in their entirety.

TECHNICAL FIELD

The present invention relates to a novel pyrrolidine compound or a pharmaceutically acceptable salt thereof, a pharmaceutical composition containing same, and the use thereof as a selective estrogen receptor degrader (or selective estrogen receptor downregulator, SERD) in the prevention or treatment of related diseases.

BACKGROUND ART

Estrogens (E2) and estrogen a receptors (ERα) are important driving factors for the occurrence and development of breast cancer. In more than two-thirds of patients with breast cancer, ER transcription factors are expressed, and in the majority of ER-positive patients, ER remains a key driving factor for tumors that progress even after early endocrine therapy, and therefore, ER is a major target for breast cancer therapy (Pharmacology & Therapeutics 186 (2018) 1-24). The purpose of endocrine therapy is to reduce ER activity. There are mainly three types of therapies, including selective estrogen receptor modulators (SERMs), such as tamoxifen, which are allosteric modulators of ER and inhibit the transcriptional activity of ER after binding thereto; aromatase inhibitors (AIs), which reduce the level of estrogens in the body by inhibiting the conversion of androgens into estrogens; and selective estrogen receptor downregulators, such as fulvestrant, which not only act as ER antagonists to inhibit the activity of ER, but also induce ER protein degradation. Although endocrine therapy is the first choice for patients with estrogen receptor-positive breast cancer, about 30% of patients will relapse after treatment, and almost all patients with metastatic breast cancer will develop drug resistance and thus, the disease progresses. There are mainly two types of mechanisms of resistance to endocrine therapies, one is focused on the estrogen receptor signaling pathway itself, including the activating mutation, amplification and fusion with other genes of the gene ESR1 encoding the estrogen receptor, dysregulation of co-regulatory factors and downstream cell cycle regulation factors of the estrogen receptor, etc.; another mechanism includes activation of signaling pathways that cross-react with the estrogen receptor signaling pathway, such as growth factor receptor pathways (*Oncol Ther,* 2017, 5:17-29).

According to clinical detection results, about 70-80% of patients with breast cancers are estrogen receptor (ER)-positive, the proliferation of such breast cancer cells is critically dependent on ER, and 50% of breast cancer death cases are of this subtype. Early-stage ER-positive breast cancer has a better prognosis, with a 5-year survival rate of over 90%. About 30% of patients with postoperative endocrine therapy (TAM or AI drugs) experience relapse within 10 years, but can still receive standard endocrine therapy. Nonetheless, acquired drug resistance and the emergence of distant metastases (such as to bone, brain, liver, lung, and lymph nodes, about 10%-15% of patients with brain metastasis) mainly caused by ESR1-LBD mutation, patients become resistant to treatment, resulting in an increasing number of drug-resistant patients. In patients with advanced metastatic breast cancer, brain metastasis is later than lung, liver, and bone metastases, the prognosis thereof is poor and the median survival period after clinical drug treatment is only 2-9 months.

Fulvestrant is the first and only SERD drug clinically approved for the treatment of postmenopausal patients with ER-positive metastatic breast cancer whose disease progresses after being treated with tamoxifen or aromatase inhibitors. Currently, AstraZeneca (see patent application WO 2018077630 A1) and Genentech (see patent application WO 2019245974 A1), each of which are incorpoared by reference herein, have also disclosed a series of SERD compounds with novel structures and the corresponding medical uses. Data from multiple studies have shown that ER degradation in patients treated with fulvestrant has not been fully achieved. In addition, the obvious reactions such as pain, swelling, and redness at the injection site caused by intramuscular injection, the slow absorption, the limited exposure in the body (fulvestrant cannot permeate through the blood-brain barrier, and the maximum dose of single intramuscular injection is only 500 mg, the pharmacodynamic characteristics thereof and intramuscular route of administration limit the maximum dose that can be given to patients) and other characteristics greatly limit its clinical application. Therefore, new treatment options are urgently needed for patients with ER-positive breast cancer.

SUMMARY OF THE INVENTION

The present invention provides a compound as represented by formula (I) or a pharmaceutically acceptable salt thereof:

(I)

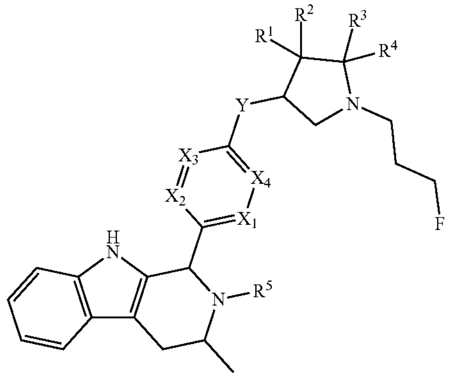

wherein $R^1$, $R^2$, $R^3$ and $R^4$ are independently selected from H, F, Cl, Br, I, CN, $C_1$-$C_6$alkyl, $C_1$-$C_6$alkoxy or $C_3$-$C_6$cycloalkyl;

$X_1$, $X_2$, $X_3$ and $X_4$ are independently selected from $CR^6$ or N;

$R^6$ is selected from H, F, Cl, Br, I, OH, CN, $C_1$-$C_{10}$alkyl, $C_3$-$C_{10}$cycloalkyl, 3-10 membered heterocyclyl, $C_1$-$C_{10}$alkoxy, $C_3$-$C_{10}$cycloalkyloxy or 3-10 membered heterocyclyloxy;

Y is selected from O or NH;

$R^5$ is independently selected from $C_1$-$C_6$alkyl, and the $C_1$-$C_6$alkyl is optionally substituted with $R^a$;

$R^a$ is selected from F, Cl, Br, I, OH, CN, $C_1$-$C_6$alkyl, $C_1$-$C_6$alkoxy or $C_3$-$C_6$cycloalkyl; provided that the compound as represented by formula (I) does not comprise

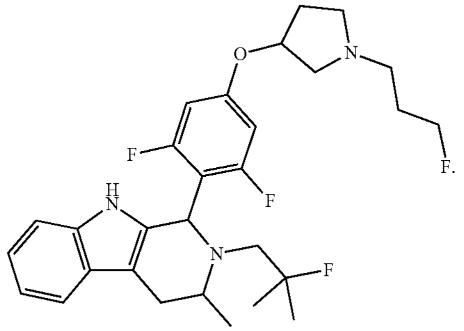 [SMILES: CC1Cc2c([nH]c3ccccc23)C(c2c(F)cc(OC3CCN(CCCF)C3)cc2F)N1CC(C)(C)F]

In some embodiments, the compound as represented by formula (I) or the pharmaceutically acceptable salt thereof is selected from a compound as represented by formula (II) or a pharmaceutically acceptable salt thereof:

(II)

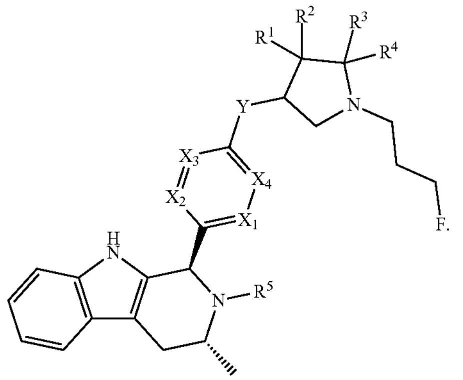

In some embodiments, the compound as represented by formula (I) or a pharmaceutically acceptable salt thereof is selected from a compound as represented by formula (III) or a pharmaceutically acceptable salt thereof:

(III)

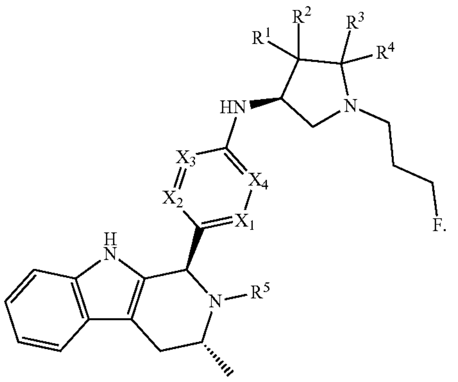

In some embodiments, $R^1$, $R^2$, $R^3$ and $R^4$ are independently selected from H, F, Cl, Br, I, CN or $C_1$-$C_6$alkyl.

In some embodiments, $R^1$, $R^2$, $R^3$ and $R^4$ are independently selected from H, F, Cl, Br, I, CN or $C_1$-$C_3$alkyl.

In some embodiments, $R^1$, $R^2$, $R^3$ and $R^4$ are independently selected from H, F, Cl, Br, I, CN or methyl.

In some embodiments, $R^1$, $R^2$, $R^3$ and $R^4$ are independently selected from H, F, Cl, Br, I or $C_1$-$C_3$alkyl.

In some embodiments, $R^1$, $R^2$, $R^3$ and $R^4$ are independently selected from H, F, Cl, Br, I or methyl.

In some embodiments, $R^1$, $R^2$, $R^3$ and $R^4$ are independently selected from H, F or methyl.

In some embodiments, $R^1$ and $R^2$ are independently selected from H, F or methyl.

In some embodiments, $R^3$ and $R^4$ are independently selected from H or methyl.

In some embodiments, $R^3$ and $R^4$ are independently selected from H.

In some embodiments, the structure unit

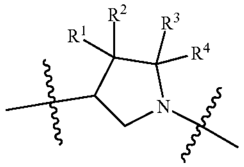

is selected from

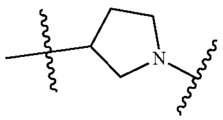

,

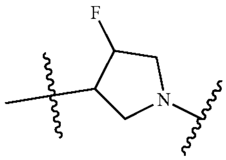

,

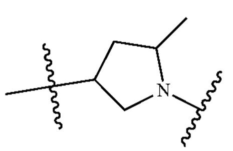

or

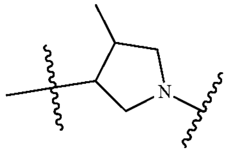

.

In some embodiments, the structure unit

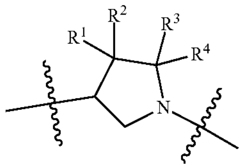

is selected from
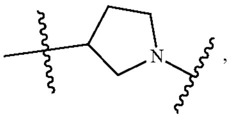
,
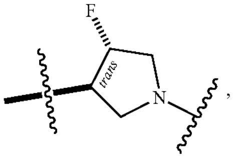
,
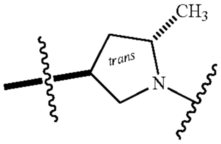
or
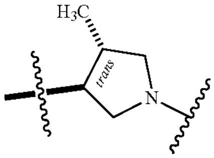
.
In some embodiments, the structure unit
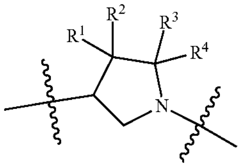
is selected from
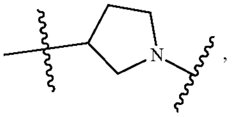 [SMILES: *C1CCN(*)C1]
,
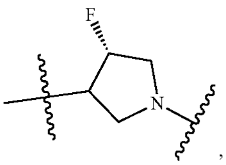
,
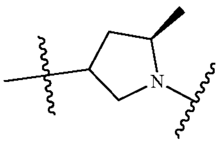
,
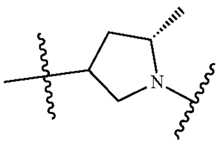
or
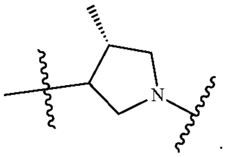
.
In some embodiments, the structure unit
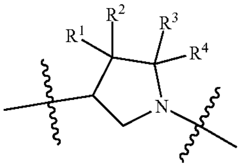
is selected from
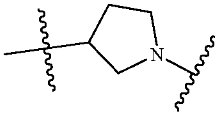
,
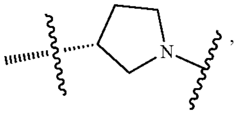
,
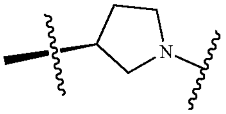
,
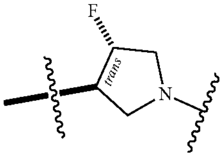
or
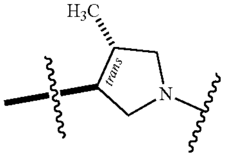
.
In some embodiments, the structure unit
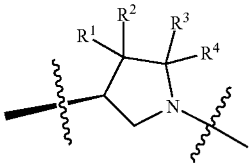
is selected from
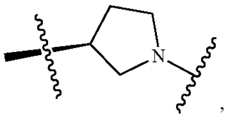
,
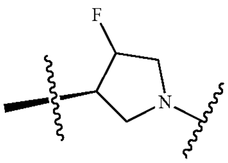
,
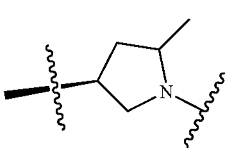
or
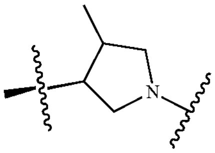
.

In some embodiments, the structure unit

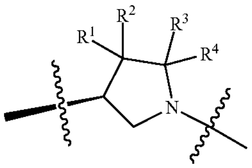

is selected front

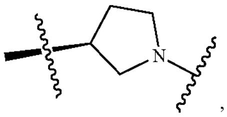

,

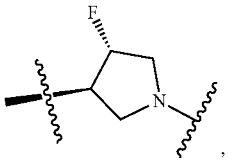

,

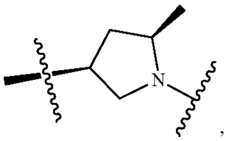

,

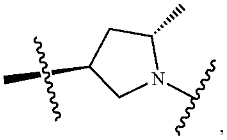

, or

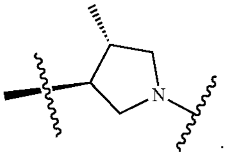

.

In some embodiments, the structure unit

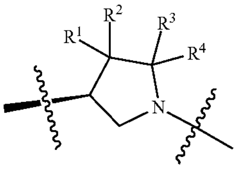

is selected front

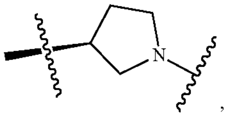

,

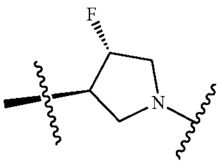

or

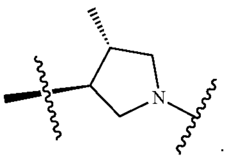

.

In some embodiments, $X_1$, $X_2$, $X_3$ and $X_4$ are independently selected from $CR^6$ or N, and at least 2 of $X_1$, $X_2$, $X_3$ and $X_4$ groups are selected from $CR^6$.

In some embodiments, $X_1$, $X_2$, $X_3$ and $X_4$ are independently selected from $CR^6$ or N, and at least 3 of $X_1$, $X_2$, $X_3$ and $X_4$ groups are selected from $CR^6$.

In some embodiments, the $R^6$ is selected from H, F, Cl, Br, I, CN, $C_1$-$C_3$alkyl or $C_1$-$C_3$alkoxy.

In some embodiments, the $R^6$ is selected from H, F, Cl, Br, I, CN or $C_1$-$C_3$alkoxy.

In some embodiments, the $R^6$ is selected from H, F, Cl, Br, I, CN or methoxyl.

In some embodiments, the $R^6$ is selected from H, F, Cl, Br, I or CN.

In some embodiments, the $R^6$ is selected from H, F, Cl, Br or I.

In some embodiments, the $R^6$ is selected from H or F.

In some embodiments, the structure unit

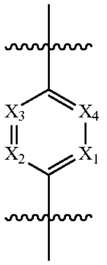

is selected from

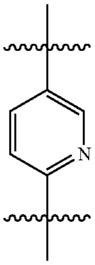 [SMILES: *c1ccc(*)nc1]

or

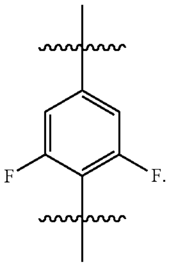 [SMILES: *c1cc(F)c(*)c(F)c1]

.

In some embodiments, the structure unit

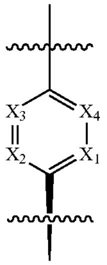

is selected from

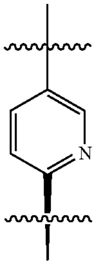

or

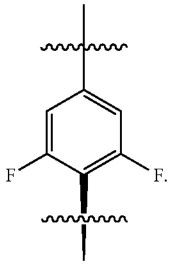

In some embodiments, $R^5$ is selected from $C_1$-$C_3$alkyl, and the $C_1$-$C_3$alkyl is optionally substituted with $R^a$.

In some embodiments, the $R^a$ is selected from F, Cl, Br, I, OH or CN.

In some embodiments, the $R^a$ is selected from F, OH or CN.

In some embodiments, the $R^a$ is selected from F or OH.

In some embodiments, $R^5$ is selected from $CH_2CF_3$, $CH_2CHF_2$, $CH_2CF_2CH_2OH$ or $CH_2CF_2CH_2CN$.

In some embodiments, $R^5$ is selected from $CH_2CF_3$ or $CH_2CF_2CH_2OH$.

In some embodiments, Y is selected from NH.

In some embodiments, the compound as represented by formula (I) or the pharmaceutically acceptable salt thereof is selected from the following compound or a pharmaceutically acceptable salt thereof:

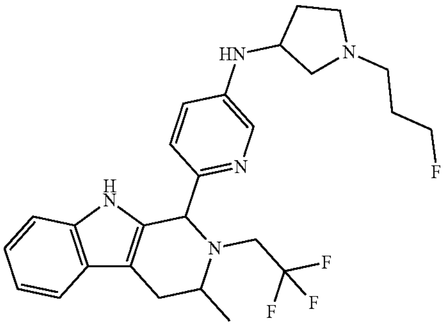

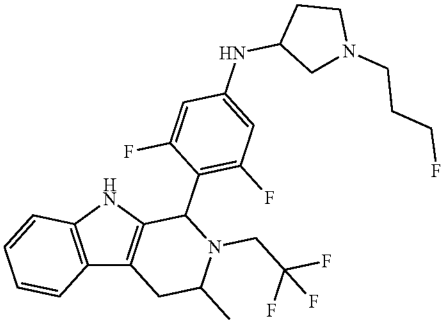

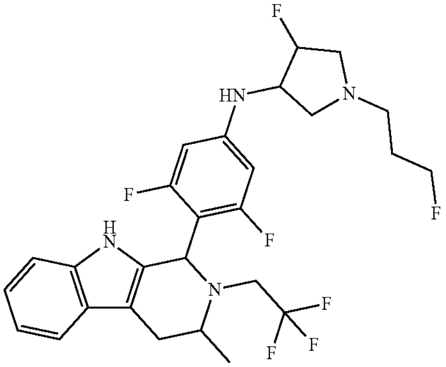

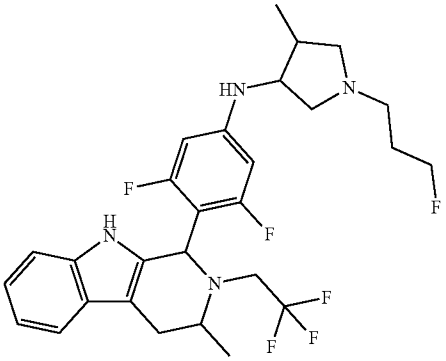

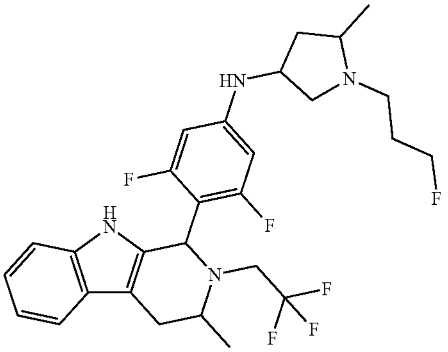

or

-continued

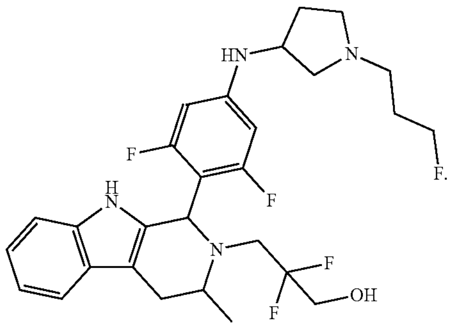

In some embodiments, the compound as represented by formula (I) or the pharmaceutically acceptable salt thereof is selected from the following compound or a pharmaceutically acceptable salt thereof:

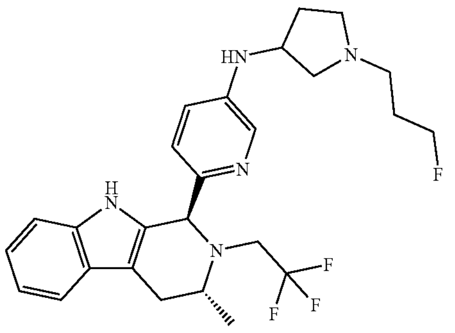

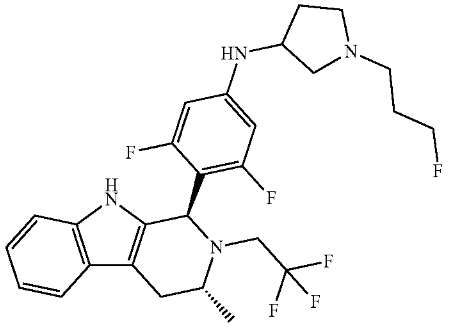

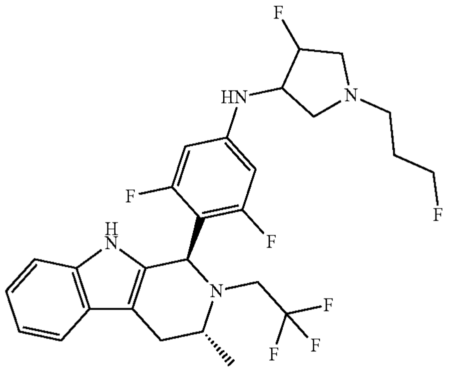

-continued

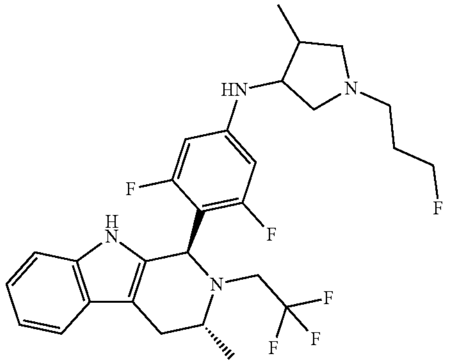

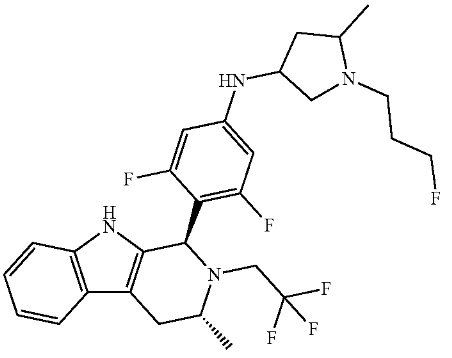

or

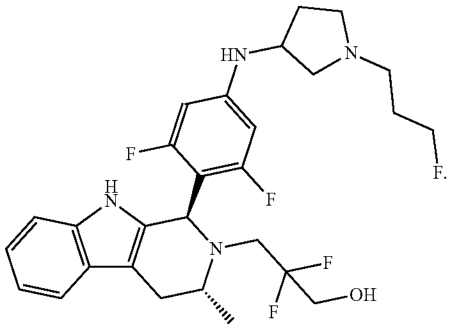

In some embodiments, the compound as represented by formula (I) or the pharmaceutically acceptable salt thereof is selected from the following compound or a pharmaceutically acceptable salt thereof:

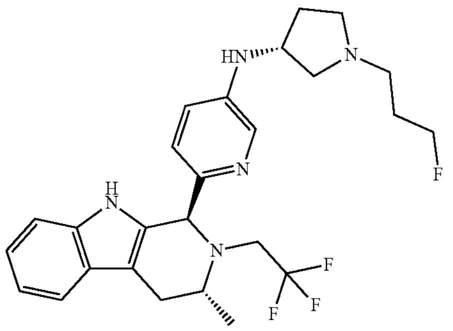

-continued
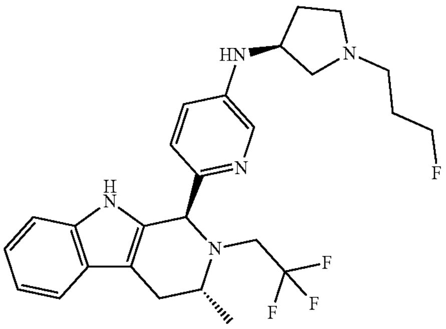
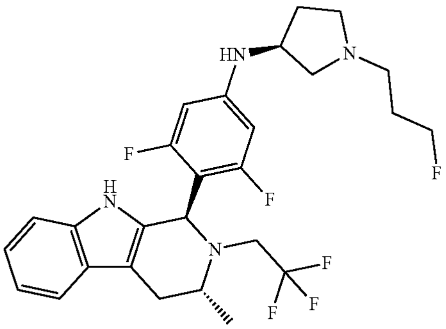
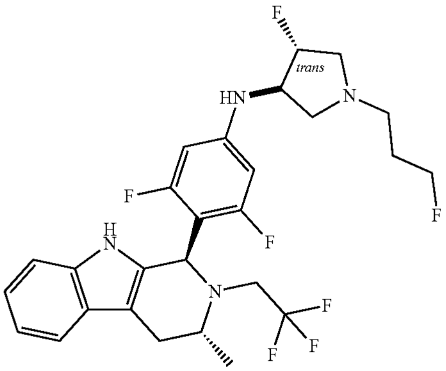
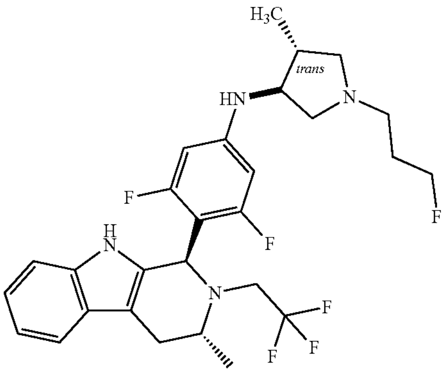
-continued
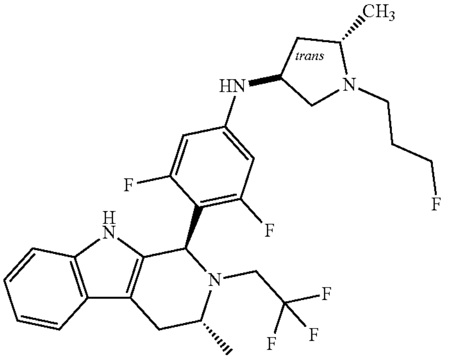
or
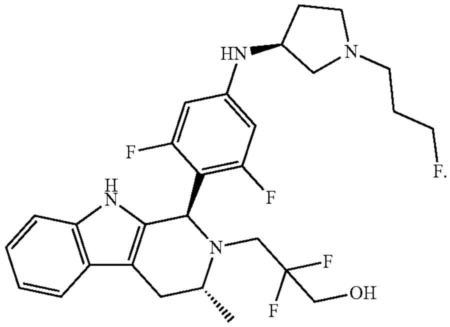
In some embodiments, the compound as represented by formula (I) or the pharmaceutically acceptable salt thereof is selected from the following compound or a pharmaceutically acceptable salt thereof:
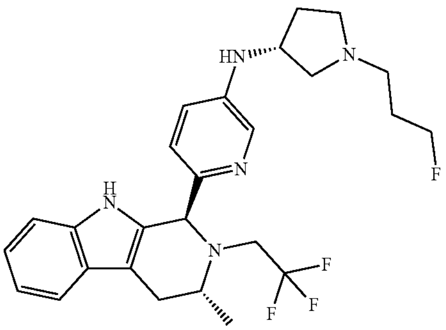
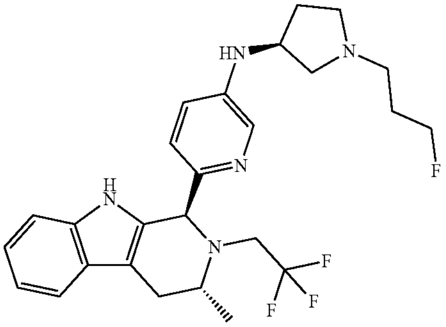

-continued
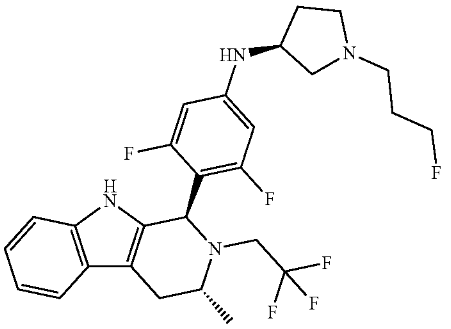
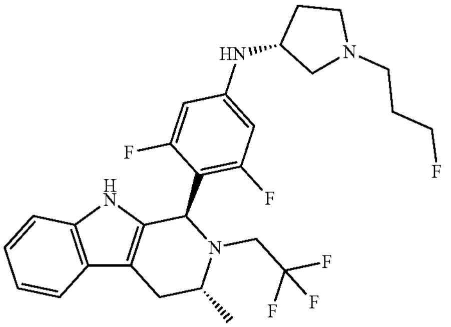
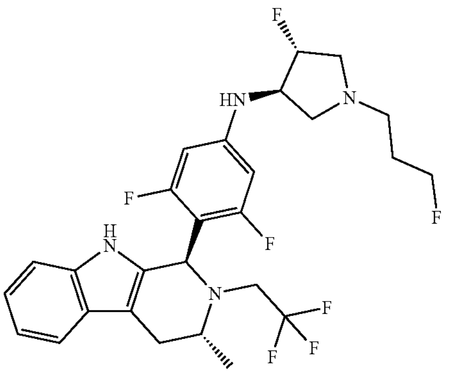
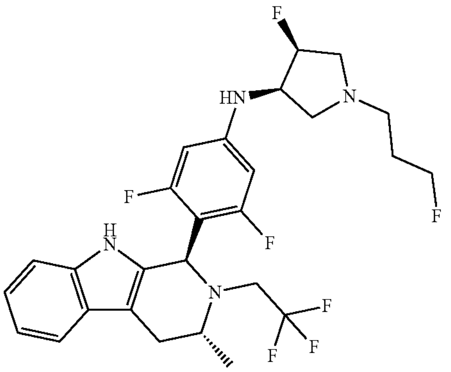
-continued
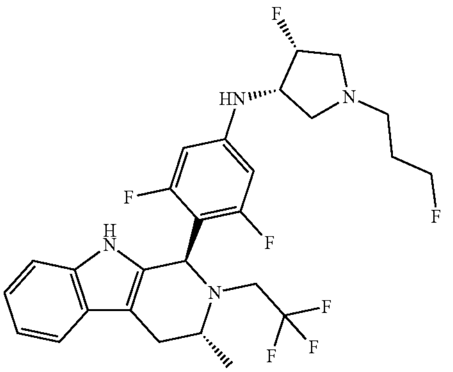
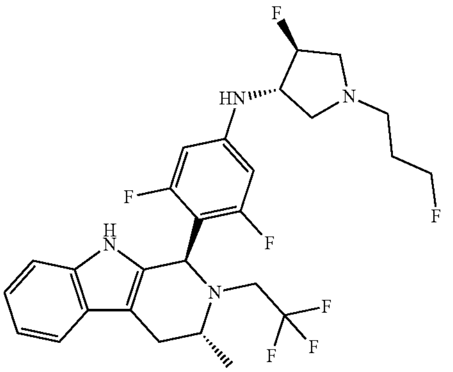
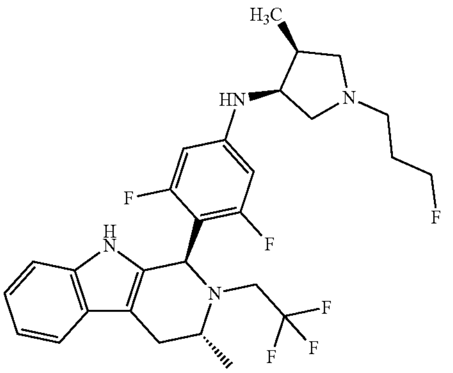
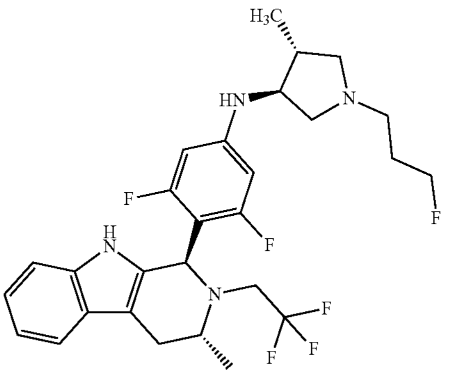

-continued
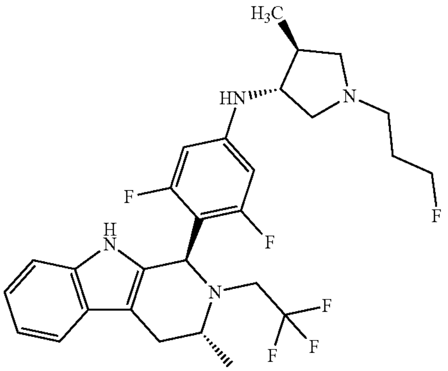
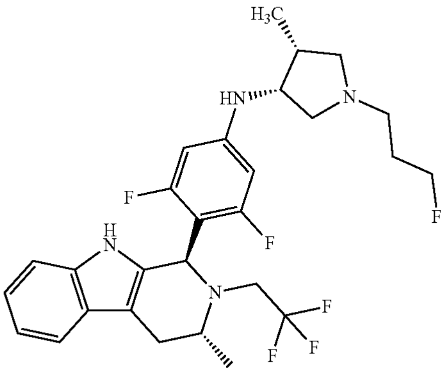
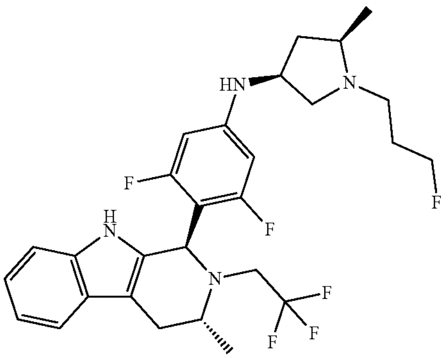
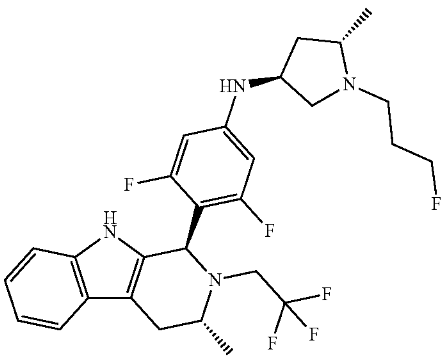
-continued
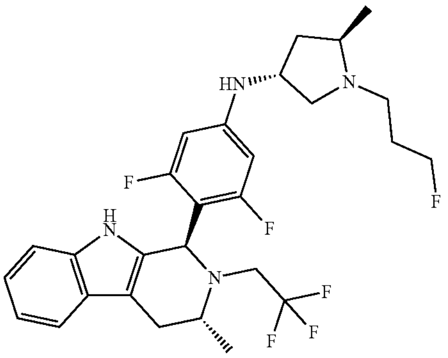
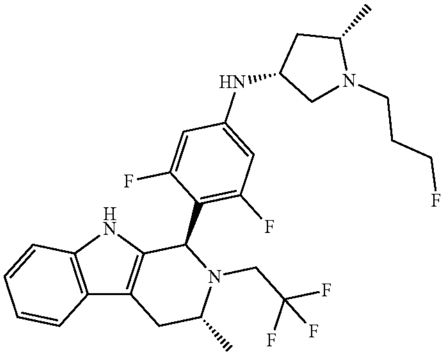
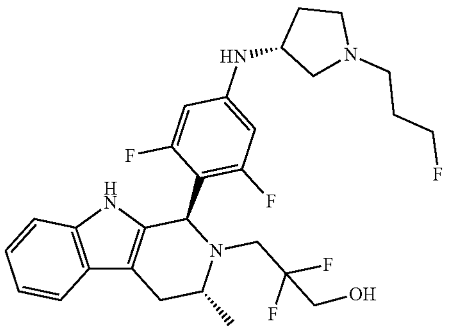
or
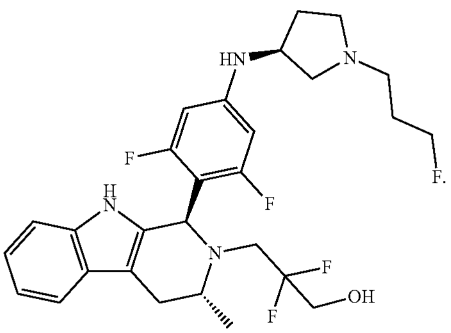
In some embodiments, the compound as represented by formula (I) or the pharmaceutically acceptable salt thereof is selected from the following compound or a pharmaceutically acceptable salt thereof:

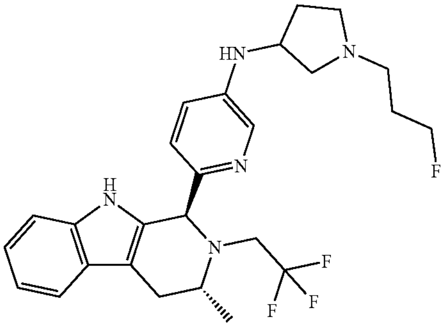

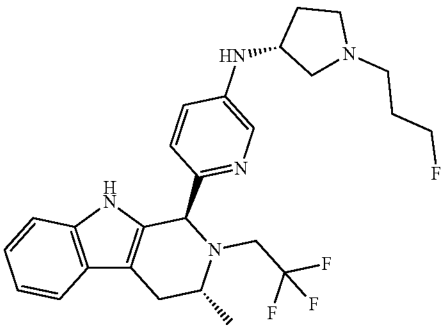

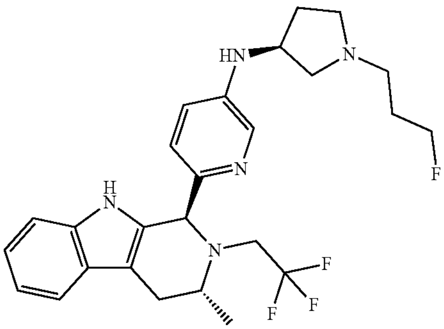

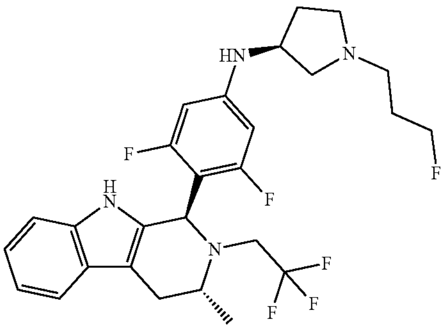

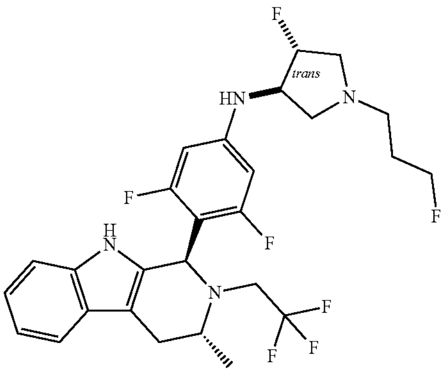

-continued

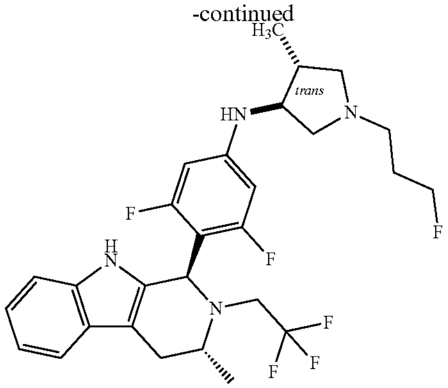

or

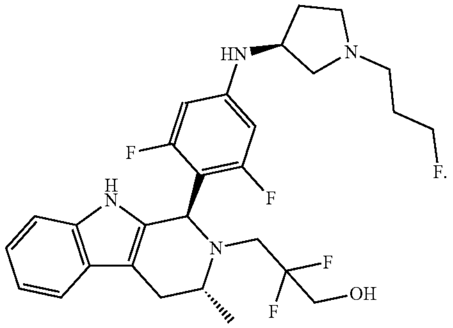

The present invention also provides a pharmaceutical composition, comprising a compound as represented by formula (I) or a pharmaceutically acceptable salt thereof and a pharmaceutically acceptable adjuvant.

Furthermore, the present invention relates to the use of the compound as represented by formula (I) or a pharmaceutically acceptable salt thereof, or the pharmaceutical composition thereof in the preparation of a drug for preventing or treating estrogen receptor-related diseases.

Furthermore, the present invention relates to a compound as represented by formula (I) or a pharmaceutically acceptable salt thereof, or a pharmaceutical composition thereof, for use in the prevention or treatment of estrogen receptor-related diseases.

Furthermore, the present invention relates to the use of a compound as represented by formula (I) or a pharmaceutically acceptable salt thereof, or the pharmaceutical composition thereof in the prevention or treatment of estrogen receptor-related diseases.

Furthermore, the present invention relates to a compound as represented by formula (I) or a pharmaceutically acceptable salt thereof, or a pharmaceutical composition thereof for the prevention or treatment of estrogen receptor-related diseases.

The present invention also relates to a method for treating estrogen receptor-related diseases, comprising administering to a patient a therapeutically effective amount of a pharmaceutical preparation comprising the compound as represented by formula (I) or a pharmaceutically acceptable salt thereof of the present invention.

In a preferred embodiment of the present invention, the estrogen receptor-related diseases include but are not limited to tumors.

In a preferred embodiment of the present invention, the estrogen receptor-related disease is breast cancer.

In a preferred embodiment of the present invention, the estrogen receptor-related disease is ER-positive breast cancer.

In a preferred embodiment of the present invention, the estrogen receptor-related disease is ER-positive breast cancer brain metastasis.

In a preferred embodiment of the present invention, the patient is a patient with breast cancer.

In a preferred embodiment of the present invention, the patient is a patient with ER-positive breast cancer.

In a preferred embodiment of the present invention, the patient is a patient with ER-positive breast cancer brain metastasis.

The compounds of the present invention have good anti-tumor activity in vitro and in vivo and druggability. The experiments in vivo found that the compounds of the present invention can significantly inhibit the tumor growth in the mouse model of ER-positive breast cancer, and significantly improve the survival period in the intracranial mouse model of ER-positive breast cancer. In addition, the compound of the present invention has a high bioavailability and a strong ability for the degradation of ER, can be administrated orally, and has a good blood-brain barrier permeability and the potential to effectively treat ER-positive breast cancer (especially ER-positive breast cancer brain metastasis).

Definition and Description of Terminology

Unless otherwise stated, the definitions of groups and terms described in the description and claims of the present invention, including their definitions as examples, exemplary definitions, preferred definitions, definitions described in tables, and definitions of specific compounds in the examples, may be mutually combined and incorporated. The group definitions and compound structures obtained after such combinations and incorporations should fall within the scope described in the description of the present invention.

As used herein, "

" refers to a linking site.

The term "pharmaceutically acceptable salt" refers to a pharmaceutically acceptable salt of a non-toxic acid or base, including salts of inorganic acids and bases and salts of organic acids and bases.

The term "stereoisomer" refers to an isomer created as a result of different spatial arrangement of atoms in molecules, including cis and trans isomers, enantiomers and diastereomers.

The compounds of the present invention may have asymmetric atoms, such as carbon atoms, sulfur atoms, nitrogen atoms, phosphorus atoms (optical centers) or asymmetric double bonds. Racemates, enantiomers, diastereomers, geometric isomers are encompassed within the scope of the present invention.

The diagrammatic presentation of the racemate or enantiomerically pure compound herein is from Maehr, J. Chem. Ed. 1985, 62:114-120. Unless otherwise specified, the wedged solid bond and wedged dashed bond ( and ) are used to represent the absolute configuration of a stereocenter, and the straight solid bond and straight dashed bond ( and ) are used to represent the cis or trans configuration of alicyclic compounds. When the compounds described herein contain olefinic double bonds or other centers of geometric asymmetry, and unless specified otherwise, it is intended that the compounds include both E and Z geometric isomers. Likewise, all tautomeric forms are encompassed within the scope of the present invention.

The compounds of the present invention may exist in specific geometric or stereoisomeric forms. The present invention contemplates all such compounds, including cis and trans isomers, (−)- and (+)-enantiomers, (R)- and (S)-enantiomers, diastereomers, (D)-isomers, (L)-isomers, and racemic mixtures and other mixtures thereof, such as enantiomerically or diastereomerically enriched mixtures, all of which fall within the scope of the present invention. Additional asymmetric carbon atoms, asymmetric sulfur atoms, asymmetric nitrogen atoms, or asymmetric phosphorus atoms may be present in substituents such as alkyl group. All these isomers and mixtures thereof are encompassed in the scope of the present invention. The compound comprising asymmetric atoms of the present application can be separated in optically active-pure or racemic forms. The optically active-pure form can be resolved from the racemic mixture or synthesized by utilizing chiral raw materials or chiral reagents. Non-limiting examples of stereoisomers include, but are not limited to:

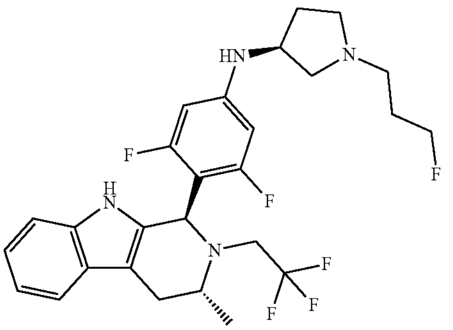

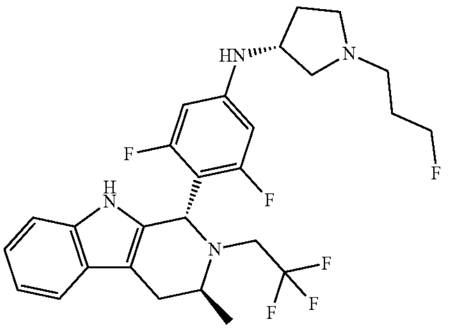

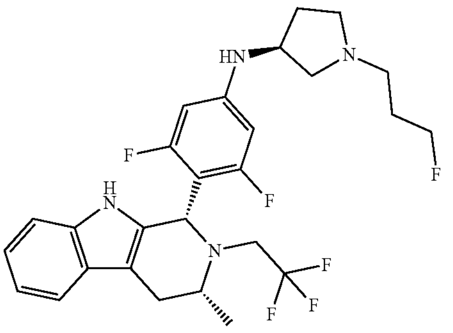

-continued

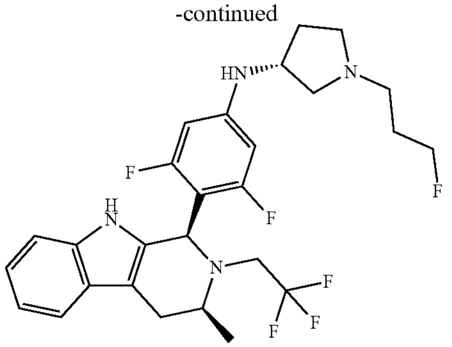

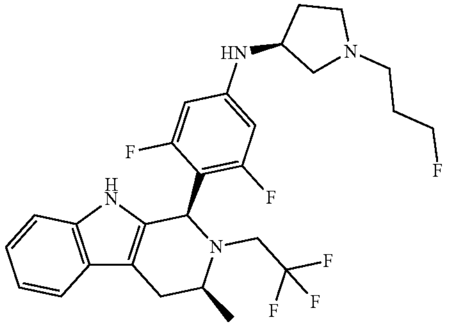

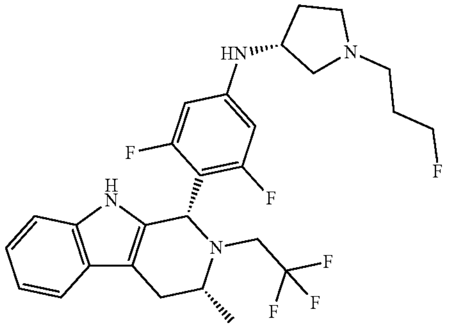

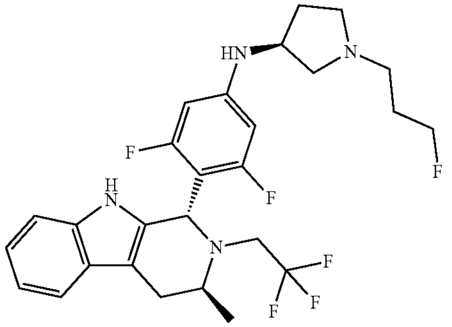

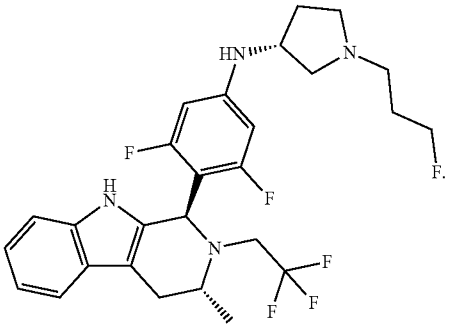

The term "tautomer" refers to a functional group isomer resulting from the rapid movement of an atom in two positions in a molecule. The compounds of the present invention may exhibit tautomerism. Tautomeric compounds can exist as two or more interconvertible forms. Tautomers generally exist in equilibrium form, so that the attempts to separate a single tautomer usually result in the formation of a mixture, whose chemical and physical properties are consistent with a mixture of the compounds. The position of equilibrium depends on the chemical properties within the molecule. For example, in many aliphatic aldehydes and ketones such as acetaldehyde, the ketone form is dominant; and in phenols, the enol form is dominant. The present invention encompasses all tautomeric forms of the compounds.

The term "pharmaceutical composition" means a mixture of one or more compounds described herein, or a physiologically/pharmaceutically acceptable salt or a prodrug thereof, and other chemical components, such as physiologically/pharmaceutically acceptable adjuvants. The purpose of the pharmaceutical composition is to facilitate the administration of a compound to an organism.

The term "substituted" means that any one or more hydrogen atoms on the designated atom are substituted with a substituent, provided that the valence state of the designated atom is normal, and the substituted compound is stable. When the substituent is oxo (i.e., =O), it means that two hydrogen atoms are substituted, which would not occur on aromatic groups.

The terms "optional" or "optionally" mean that the subsequently described event or circumstance may or may not occur, and the description includes the occurrence and the non-occurrence of the event or circumstance. For example, the expression "ethyl is "optionally" substituted with halogen" means that ethyl may be unsubstituted ($CH_2CH_3$), mono-substituted (such as $CH_2CH_2F$), polysubstituted (such as $CHFCH_2F$, $CH_2CHF_2$), or completely substituted ($CF_2CF_3$). With respect to any group containing one or more substituents, it will be understood by those skilled in the art that any substitution or substitution patterns that are sterically impractical and/or synthetically non-feasible are not intended to be introduced into such groups.

Where any variable (such as $R^a$, $R^b$) appears more than once in the constitution or structure of a compound, its definition in each case is independent. For example, if a group is substituted with two $R^b$, then each $R^b$ has an independent option.

When the number of a linking group is 0, such as $-(CH_2)_0-$, it means that the linking group is a bond.

When one of the variables is selected from a chemical bond or absent, it means that the two groups to which it is connected are directly connected. For example, when L represents a bond in A-L-Z, it means that the structure is actually A-Z.

When the linking direction of the linking group referred to herein is not indicated, the linking direction is arbitrary. For example, in the case where $L^1$ in the structural unit

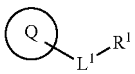

is selected from "$C_1$-$C_3$alkylene-O", $L^1$ can connect ring Q and $R^1$ in the same direction as the reading order from left to right to form "ring Q-$C_1$-$C_3$alkylene-O—$R^1$", and can also connect ring Q and $R^1$ in the opposite direction as the reading order from left to right to form "ring Q-O—$C_1$-$C_3$alkylene-$R^1$".

The term "halo" or "halogen" refers to fluoro, chloro, bromo and iodo.

$C_m$-$C_n$ herein means that it has an integer number of carbon atoms, wherein the integer number is within the range of m-n. For example, "$C_1$-$C_{10}$" means that the group may have 1, 2, 3, 4, 5, 6, 7, 8, 9, or 10 carbon atoms.

The term "alkyl" refers to a hydrocarbon group of the general formula $C_nH_{2n+1}$, which may be linear or branched. The term "$C_1$-$C_{10}$alkyl" is to be understood as denoting a linear or branched, saturated monovalent hydrocarbon group having 1, 2, 3, 4, 5, 6, 7, 8, 9, or 10 carbon atoms. For example, the alkyl is methyl, ethyl, propyl, butyl, pentyl, hexyl, isopropyl, isobutyl, sec-butyl, tert-butyl, isopentyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl; preferably, "$C_1$-$C_{10}$alkyl" may comprise "$C_1$-$C_6$alkyl" or "$C_1$-$C_3$alkyl", "$C_1$-$C_6$alkyl" is to be understood as denoting a linear or branched saturated monovalent hydrocarbon group having 1, 2, 3, 4, 5, or 6 carbon atoms, and "$C_1$-$C_3$alkyl" is to be understood as denoting a linear or branched saturated monovalent hydrocarbon group having 1, 2 or 3 carbon atoms.

The term "$C_1$-$C_{10}$alkoxy" can be understood as "$C_1$-$C_{10}$alkyloxy" or "$C_1$-$C_{10}$alkyl-O—"; preferably, "$C_1$-$C_{10}$alkoxy" may comprise "$C_1$-$C_6$alkoxy" or "$C_1$-$C_3$alkoxy".

The term "$C_3$-$C_{10}$cycloalkyl" is to be understood as denoting a saturated monovalent monocyclic or bicyclic hydrocarbon ring having 3 to 10 carbon atoms, such as cyclopropyl, cyclobutyl, cyclopentyl, cyclohexyl, cycloheptyl, cyclooctyl, cyclononyl or cyclodecyl, or a bicyclic hydrocarbon group such as decalin ring. The term "$C_3$-$C_6$cycloalkyl" is to be understood as denoting a saturated monovalent monocyclic or bicyclic hydrocarbon ring having 3 to 6 carbon atoms.

The term "$C_3$-$C_{10}$cycloalkyloxy" can be understood as "$C_3$-$C_{10}$cycloalkyl-O—"; preferably, "$C_3$-$C_{10}$cycloalkyloxy" may comprise "$C_3$-$C_6$ cycloalkyloxy".

The term "heterocyclyl" refers to a fully saturated or partially saturated (not a heteroaromatic group which is aromatic as a whole) monovalent monocyclic, fused ring, spirocyclic or bridged ring group, the ring atoms therein containing 1-5 heteroatoms or heteroatomic groups (namely, atomic groups containing heteroatoms), wherein the "heteroatoms or heteroatomic groups" include but are not limited to nitrogen atoms (N), oxygen atoms (O), sulfur atoms (S), phosphorus atoms (P), boron atoms (B), ═O, ═S, —O—N═, —C(═O)O—, —C(═O)—, —C(═S)—, —S(═O)$_2$—, —S(═O)—, and optionally substituted —NH—, —S(═O)(═NH)—, —C(═O)NH—, —C(═NH)—, —S(═O)$_2$NH—, S(═O)NH—, —NHC(═O)NH—, and the like. The term "3-10 membered heterocyclyl" means a heterocyclyl group having a number of ring atoms of 3, 4, 5, 6, 7, 8, 9 or 10, wherein the ring atoms contain 1-5 heteroatoms or heteroatom groups which are independently selected from the above-mentioned heteroatoms or heteroatom groups. In particular, examples of 3-membered heterocyclyl include, but are not limited to epoxypropyl or azacyclopropyl; examples of 4-membered heterocyclyl include, but are not limited to azetidinyl, oxetanyl; examples of 5-membered heterocyclyl include, but are not limited to tetrahydrofuranyl, dioxolyl, pyrrolidinyl, imidazolidinyl, pyrazolidinyl, pyrrolinyl, 4,5-dihydrooxazole or 2,5-dihydro-1H-pyrrolyl; examples of 6-membered heterocyclyl include, but are not limited to tetrahydropyranyl, piperidyl, morpholinyl, dithianyl, thiomorpholinyl, piperazinyl, trithianyl, tetrahydropyridyl or 4H-[1,3,4]thiadiazinyl; examples of 7-membered heterocyclyl include, but are not limited to diazepanyl; the heterocyclyl may also be a bicyclic group, specifically, examples of 5,5-membered bicyclic groups include, but are not limited to hexahydrocyclopenta[c]pyrrol-2(1H)-yl, and examples of 5,6-membered bicyclic groups include, but not limited to hexahydropyrrolo[1,2-a]pyrazin-2(1H)-yl, 5,6,7,8-tetrahydro-[1,2,4]triazolo [4,3-a]pyrazinyl or 5,6,7,8-tetrahydroimidazo[1,5-a]pyrazinyl. Optionally, the heterocyclyl may be a benzo-fused ring group of the above-mentioned 4-7 membered heterocyclyl, examples including but not limited to dihydroisoquinolinyl, and the like. Optionally, the 3-10 membered heterocyclyl may be a "3-10 membered heterocycloalkyl"; "3-10 membered heterocycloalkyl" may further include ranges of such as "3-7 membered heterocycloalkyl" or "5-6 membered heterocycloalkyl". Although some bicyclic heterocyclyl groups in the present application partially contain one benzene ring or one heteroaromatic ring, the heterocyclyl groups are still non-aromatic as a whole.

The term "3-10 membered heterocyclyloxy" refers to "3-10 membered heterocyclyl-O—".

The term "treatment" refers to the administration of the compounds or preparations of the present application for preventing, ameliorating or eliminating diseases or one or more symptoms associated with the diseases and comprises:

(i) prophylaxis of occurrence of diseases or conditions in mammals, particularly when the mammals are susceptible to the conditions, but have not been diagnosed with the conditions;

(ii) inhibition of diseases or conditions, i.e., restraining their development;

(iii) relief of diseases or conditions, i.e., resolution of the diseases or conditions.

The term "therapeutically effective amount" means an amount of a compound of the present invention that (i) treats or prevents a particular disease, condition, or disorder, (ii) attenuates, ameliorates, or eliminates one or more symptoms of a particular disease, condition, or disorder, or (iii) prevents or delays the onset of one or more symptoms of a particular disease, condition, or disorder described herein. The amount of a compound of the present invention which constitutes a "therapeutically effective amount" will vary depending on the compound, the conditions and their severity, the manner of administration, and the age of the mammal to be treated, but can be determined routinely by those skilled in the art according to their own knowledge and the present disclosure.

The term "adjuvant" refers to a pharmaceutically acceptable inert ingredient. Examples of types of the term "excipient" include, without limitation, a binder, a disintegrant, a lubricant, a glidant, a stabilizer, a filler, a diluent, and the like. Excipients can improve the operation characteristics of a pharmaceutical preparation, i.e., making the preparation more suitable for direct compression by increasing flowability and/or stickiness. Examples of typical "pharmaceutically acceptable carriers" suitable for use in the above-mentioned preparations are: carbohydrates, starches, cellulose and the derivatives thereof, which are adjuvants commonly used in pharmaceutical preparations.

The term "pharmaceutically acceptable adjuvant" refers to those adjuvants which have no significant irritating effect on the organism and do not impair the bioactivity and properties of the active compound. Suitable adjuvants are well known to those skilled in the art, and are such as a carbohydrate, a wax, a water-soluble and/or water-swellable polymer, a hydrophilic or hydrophobic material, gelatin, an oil, a solvent, water, and the like.

The word "comprise" and its variants such as "comprises" or "comprising" is to be understood as an open, non-exclusive meaning, i.e., "comprising but not limited to".

The compounds of the present invention can be prepared by various synthetic methods well known to those skilled in the art, including the specific embodiments listed below, the embodiments formed by the combination with other chemical synthesis methods, and equivalent alternative embodiments well known to those skilled in the art, wherein the preferred embodiments include but are not limited to the examples of the present invention.

The present application also includes isotopically-labeled compounds of the present application which are identical to those recited herein, but have one or more atoms replaced by an atom having an atomic mass or mass number different from the atomic mass or mass number usually found in nature. Examples of isotopes that can be incorporated into compounds of the present application include isotopes of hydrogen, carbon, nitrogen, oxygen, phosphorus, sulfur, fluorine, iodine, and chlorine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{123}I$, $^{125}I$ and $^{36}Cl$, respectively.

Certain isotopically-labeled compounds of the present application (e.g., those labeled with $^{3}H$ and $^{14}C$) are useful in tissue distribution assays of compounds and/or substrates. Tritiated (i.e., $^{3}H$) and carbon-14 (i.e., $^{14}C$) isotopes are particularly preferred for their ease of preparation and detectability. Positron emitting isotopes such as $^{15}O$, $^{13}N$, $^{11}C$, and $^{18}F$ are useful for positron emission tomography (PET) studies to examine substrate occupancy. The isotopically-labeled compounds of the present application can generally be prepared according to following procedures analogous to those disclosed in the Schemes and/or in the Examples herein below by substituting a non-isotopically-labeled reagent with an isotopically-labeled reagent.

Furthermore, substitution with heavier isotopes (such as deuterium, i.e., $^{2}H$) may afford certain therapeutic advantages resulting from greater metabolic stability, for example, increased in vivo half-life or reduced dosage requirements, and hence may be preferred in some circumstances, wherein the deuterium substitution may be partial or complete, and partial deuterium substitution means that at least one hydrogen is substituted with at least one deuterium.

The pharmaceutical composition of the present application may be prepared by combining the compound of the present application with an appropriate pharmaceutically acceptable adjuvant. For example, the pharmaceutical composition of the present application may be formulated into solid, semi-solid, liquid or gaseous preparations, such as tablets, pills, capsules, powders, granules, ointments, emulsions, suspensions, suppositories, injections, inhalants, gels, microspheres, and aerosols, and the like.

Typical administration routes of the compound or the pharmaceutically acceptable salt thereof, or the pharmaceutical composition thereof according to the present application include, but are not limited to, oral administration, rectal administration, topical administration, administration by inhalation, parenteral administration, sublingual administration, intravaginal administration, intranasal administration, intraocular administration, intraperitoneal administration, intramuscular administration, subcutaneous administration, and intravenous administration.

The pharmaceutical composition of the present application can be manufactured by using well-known methods in the art, such as conventional mixing method, dissolution method, granulation method, dragee manufacture method, grinding method, emulsification method, and freeze-drying method, and the like.

In some embodiments, the pharmaceutical composition is in oral form. For oral administration, the pharmaceutical composition may be formulated by mixing the active compound with a pharmaceutically acceptable adjuvant well-known in the art. Such adjuvants enable the compounds of the present application to be formulated into tablets, pills, lozenges, dragees, capsules, liquids, gels, syrups, suspensions and the like, for oral administration to patients.

A solid oral composition can be prepared by a conventional mixing, filling or tabletting method. For example, it can be obtained by mixing the active compound with a solid adjuvant, optionally grinding the resulting mixture, adding other suitable adjuvants, if necessary, and then processing the mixture into granules to obtain cores of tablets or dragees. Suitable adjuvants include but are not limited to: binders, diluents, disintegrants, lubricants, glidants, sweeteners or flavoring agents, and the like.

The pharmaceutical composition can also be suitable for parenteral administration, such as sterile solutions, suspensions or lyophilized products in a suitable unit dosage form.

The daily administration dose of the compound of general formula I in all the administration manners described herein is from 0.01 mg/kg body weight to 100 mg/kg body weight, preferably from 0.05 mg/kg body weight to 50 mg/kg body weight, and more preferably from 0.1 mg/kg body weight to 30 mg/kg body weight, in the form of a single dose or divided doses.

The chemical reactions described in the specific embodiments of the present invention are completed in a suitable solvent, wherein the solvent must be suitable for the chemical changes of the present invention and the reagents and materials required thereby. In order to obtain the compounds of the present invention, sometimes a person skilled in the art needs to modify or select synthesis steps or reaction schemes based on the existing embodiments.

DETAILED DESCRIPTION OF EMBODIMENTS

Figure 1:
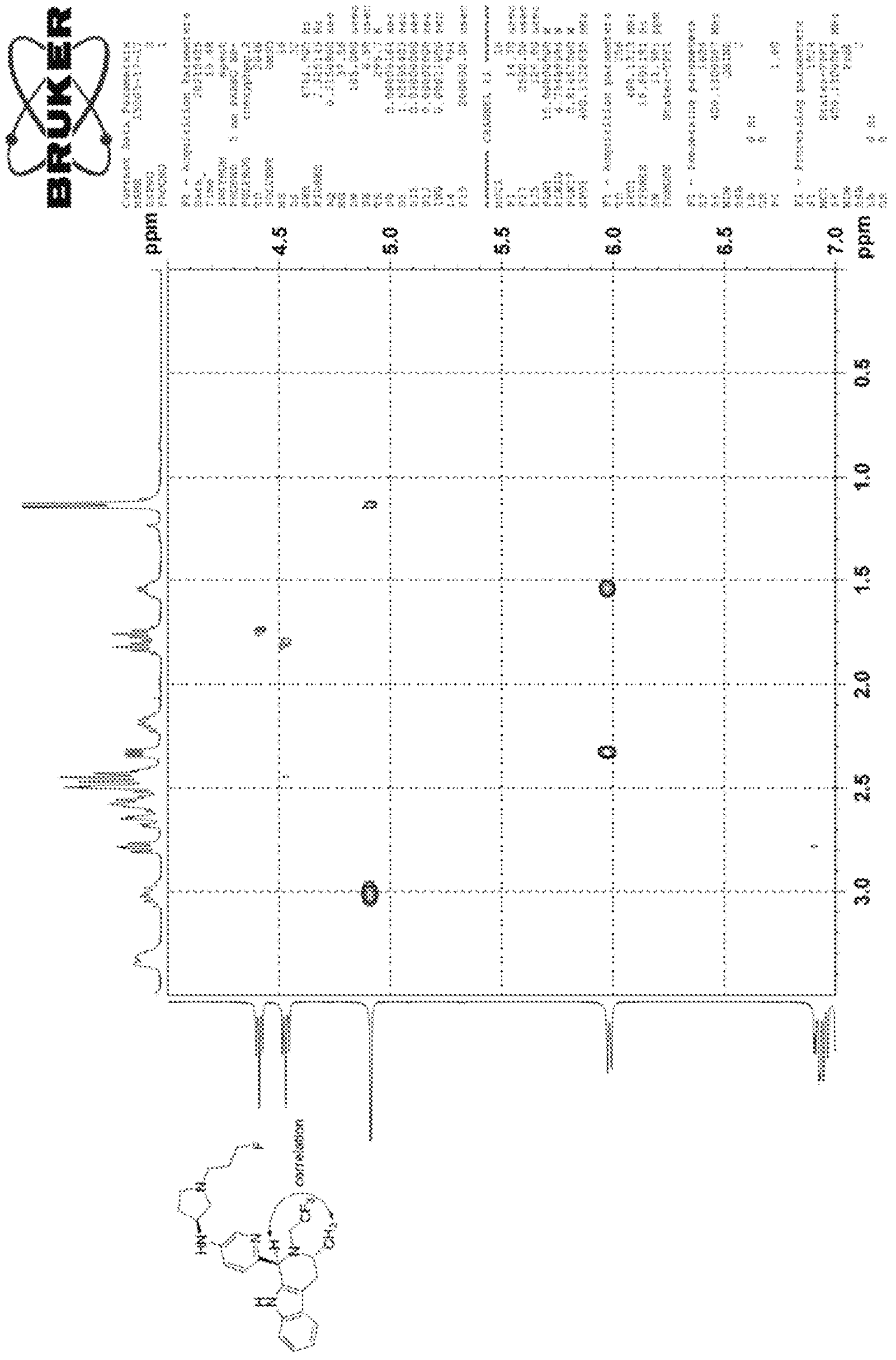
FIG. 1 is a NOESY spectrum of compound 3.

The technical solutions of the present invention will be described in detail by the following examples, but the scope of protection of the present invention includes but is not limited thereto.

The structures of the compounds are determined by nuclear magnetic resonance (NMR) and/or mass spectrometry (MS). The NMR shifts are calculated in $10^{-6}$ (ppm). The solvents for NMR analysis are deuterated dimethyl sulfoxide, deuterated chloroform, deuterated methanol, etc., and the internal standard is tetramethylsilane (TMS); "$IC_{50}$" refers to the half inhibitory concentration, the concentration at which half of the maximal inhibitory effect is achieved.

Example 1: Synthesis of N-(1-(3-fluoropropyl)pyrrolidin-3-yl)-6-((1S,3R)-3-methyl-2-(2,2,2-trifluoroethyl)-2,3,4,9-tetrahydro-1H-pyridino[3,4-b]indol-1-yl)pyridine-3-amine (Compound 1)

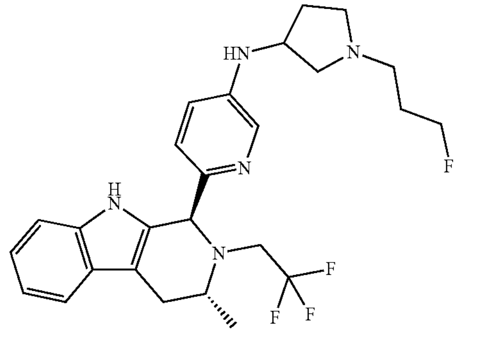 [SMILES: C[C@@H]1Cc2c([nH]c3ccccc23)[C@@H](c2ccc(NC3CCN(CCCF)C3)cn2)N1CC(F)(F)F]

Synthesis Method:

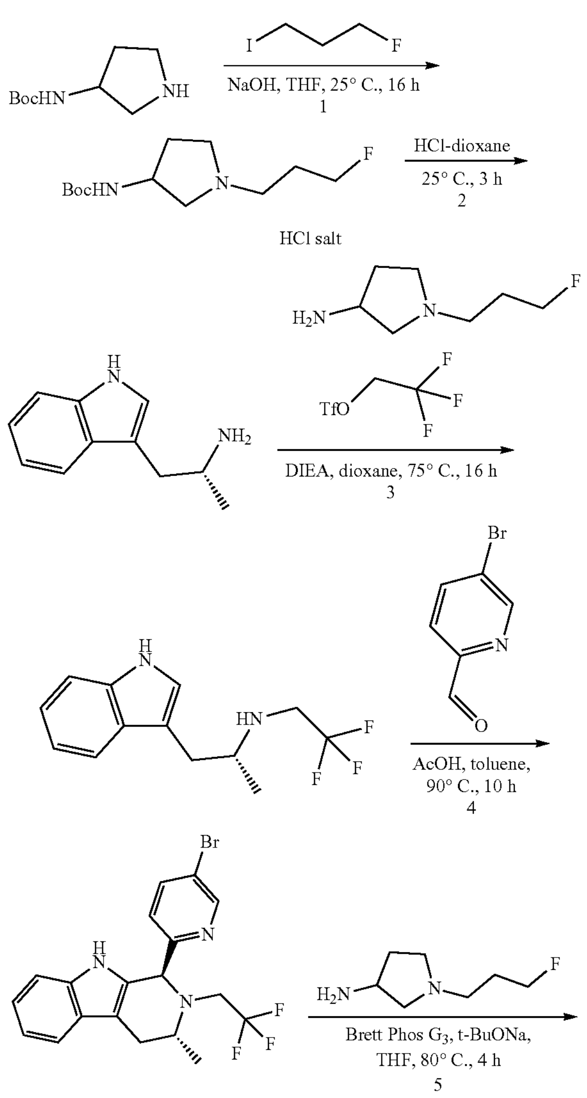

-continued

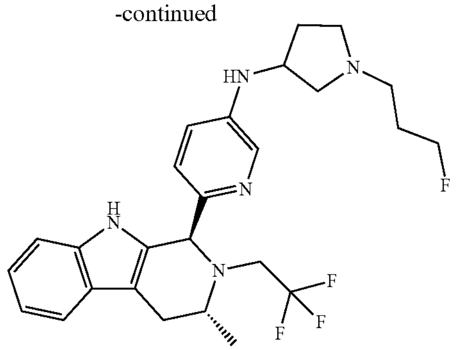

Step 1: Synthesis of tert-butyl (1-(3-fluoropropyl)pyrrolidin-3-yl)carbamate

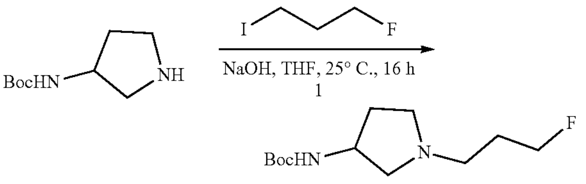

Tert-butyl pyrrolidin-3-ylcarbamate (1.00 g, 5.37 mmol) was dissolved in tetrahydrofuran (10 mL), and sodium hydroxide solution (5 mol·$L^{-1}$, 2.15 mL) and 1-iodo-3-fluoropropane (1.06 g, 5.64 mmol) were added. The reaction solution was stirred at 25° C. for 16 hours. After completion of the reaction of the raw materials detected by TLC, the reaction solution was diluted with ethyl acetate, and then washed with saturated ammonium chloride solution, and the aqueous phase and the organic phase were collected separately. The aqueous phase was extracted with ethyl acetate (50 mL) three times, and then all organic phases were combined and dried over sodium sulfate, and the organic phase was concentrated to dryness under reduced pressure, and then purified by column chromatography (silica, dichloromethane/methanol=100/1) to obtain the product tert-butyl (1-(3-fluoropropyl)pyrrolidin-3-yl)carbamate (0.81 g).

$^{1}$H NMR (400 MHz, METHANOL-$d_4$) δ 4.57 (t, J=5.77 Hz, 1H), 4.45 (t, J=5.77 Hz, 1H), 4.11 (br d, J=7.78 Hz, 1H), 3.05-2.97 (m, 1H), 2.93-2.81 (m, 1H), 2.80-2.69 (m, 3H), 2.66-2.56 (m, 1H), 2.30-2.20 (m, 1H), 2.04-1.87 (m, 2H), 1.78-1.68 (m, 1H), 1.51-1.38 (m, 9H).

Step 2: Synthesis of 1-(3-fluoropropyl)pyrrolidin-3-amine hydrochloride

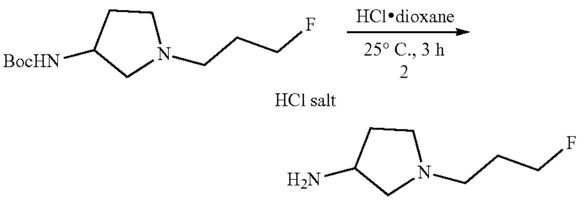

Tert-butyl(1-(3-fluoropropyl)pyrrolidin-3-yl)carbamate (0.81 g, 3.12 mmol) was dissolved in 1,4-dioxane (9 mL), and then hydrochloric acid-1,4-dioxane solution (4 moL·L$^{-1}$, 9 mL) was added, the mixture was reacted to obtain a yellow transparent solution. The reaction solution was stirred at 25° C. for 3 hours. After completion of the reaction of the raw materials detected by TLC, the reaction solution was concentrated under reduced pressure to dryness to obtain a compound 1-(3-fluoropropyl)pyrrolidin-3-amine hydrochloride (0.71 g).

$^1$H NMR (400 MHz, METHANOL-$d_4$) δ 4.68 (t, J=5.52 Hz, 1H), 4.56 (s, 1H), 4.30-3.79 (m, 3H), 3.68 (s, 1H), 3.48 (br s, 2H), 3.31-3.21 (m, 1H), 2.82-2.46 (m, 1H), 2.32-2.14 (m, 3H).

Step 3: Synthesis of (R)-1-(1H-indol-3-yl)-N-(2,2,2-trifluoroethyl)propane-2-amine

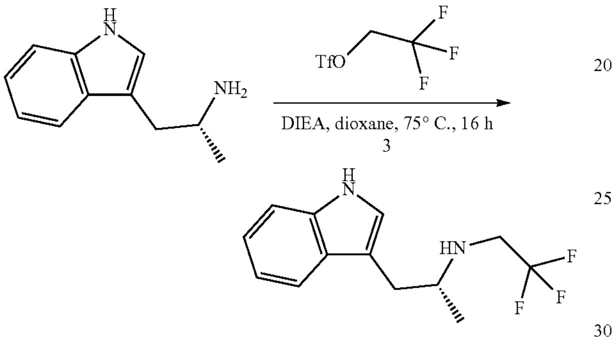

(2R)-1-(1H-indol-3-yl)propane-2-amine (600 mg, 3.44 mmol) and N,N-diisopropylethylamine (445.05 mg, 3.44 mmol) were dissolved in 1,4-dioxane (10 mL), trifluoroethyl trifluoromethanesulfonate (1.20 g, 5.17 mmol) dissolved in 1,4-dioxane (5 mL) was added at 25° C., and the reaction solution was stirred at 75° C. for 16 hours. The reaction solution was concentrated to dryness under reduced pressure. Then the crude product was purified by column chromatography (silica, petroleum ether/ethyl acetate=3/1) to obtain a product (R)-1-(1H-indol-3-yl)-N-(2,2,2-trifluoroethyl)propane-2-amine (0.69 g).

MS m/z (ESI): 257.2 [M+H]$^+$;

$^1$H NMR (400 MHz, METHANOL-$d_4$) δ 7.56-7.54 (d, J=8.0 Hz, 1H), 7.36-7.34 (d, J=8.0 Hz, 1H), 7.12-7.08 (m, 2H), 7.03-7.00 (m, 1H), 3.26-3.23 (m, 2H), 3.12-3.10 (m, 1H), 2.93-2.88 (m, 1H), 2.80-2.78 (m, 1H), 1.11 (d, J=6.0 Hz, 3H).

Step 4: Synthesis of (1S,3R)-1-(5-bromopyridin-2-yl)-3-methyl-2-(2,2,2-trifluoroethyl)-2,3,4,9-tetrahydro-1H-pyridino[3,4-b]indole

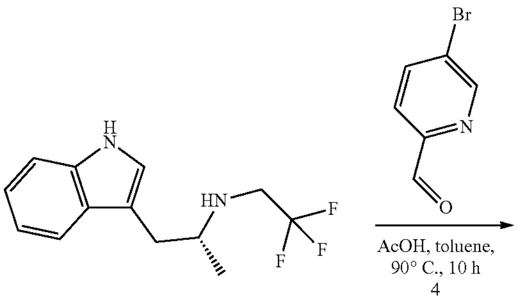

-continued

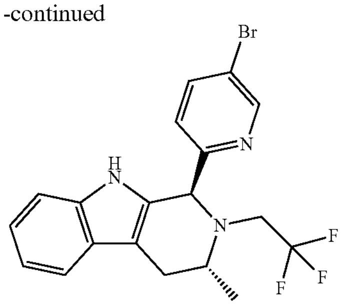

(R)-1-(1H-indol-3-yl)-N-(2,2,2-trifluoroethyl)propane-2-amine (120.00 mg, 468.26 mol) was dissolved in toluene (2 mL), 5-bromo-pyridine-2-formaldehyde (87.10 mg, 468.26 mol) and acetic acid (562.40 mg, 9.37 mmol) were added, and the reaction solution was a yellow transparent solution. The reaction solution was stirred at 90° C. for 10 hours. After the completion of the reaction detected by LCMS, the reaction solution was cooled to room temperature, concentrated to dryness under reduced pressure, and purified by thin layer chromatography (silica, petroleum ether/ethyl acetate=4/1) to obtain (1S,3R)-1-(5-bromopyridin-2-yl)-3-methyl-2-(2,2,2-trifluoroethyl)-2,3,4,9-tetrahydro-1H-pyridino[3,4-b]indole (110.00 mg).

MS m/z (ESI): 424.1, 426.1 [M+H]$^+$.

$^1$H NMR (400 MHz, METHANOL-$d_4$) δ 8.59 (s, 1H), 8.01-7.94 (m, 1H), 7.54 (d, J=8.53 Hz, 1H), 7.46 (d, J=7.78 Hz, 1H), 7.30 (d, J=8.03 Hz, 1H), 7.08 (d, J=7.59 Hz, 1H), 7.03-6.96 (m, 1H), 5.08 (s, 1H), 3.58-3.46 (m, 1H), 3.38-3.34 (m, 1H), 3.13-2.99- (m, 1H), 2.80 (d, J=4.52 Hz, 1H), 2.70-2.61 (m, 1H), 1.26 (d, J=6.78 Hz, 3H).

Step 5: Synthesis of N-(1-(3-fluoropropyl)pyrrolidin-3-yl)-6-((1S,3R)-3-methyl-2-(2,2,2-trifluoroethyl)-2,3,4,9-tetrahydro-1H-pyridino[3,4-b]indol-1-yl)pyridine-3-amine

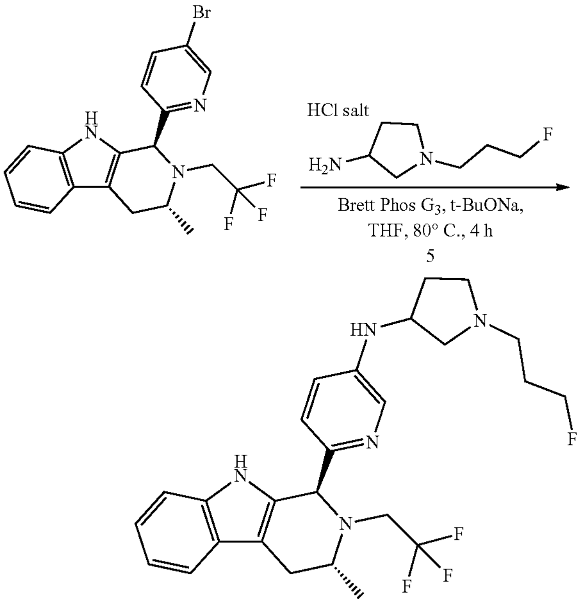

(1S,3R)-1-(5-bromopyridin-2-yl)-3-methyl-2-(2,2,2-trifluoroethyl)-2,3,4,9-tetrahydro-1H-pyridino[3,4-b]indole (110.00 mg, 259.28 μmol) was dissolved in tetrahydrofuran (2 mL), 1-(3-fluoropropyl)pyrrolidin-3-amine hydrochloride (68.18 mg, 311.13 μmol), sodium tert-butoxide (149.50 mg, 1.56 mmol) and methanesulfonic acid(2-dicyclohexylphosphino)-3,6-dimethoxyl-2,4,6-triisopropyl-1,1-biphenyl)(2-amino-1,1-biphenyl-2-yl)palladium(II) (23.50 mg, 25.93 μmol) were added, and the reaction solution was a brown turbid solution under nitrogen atmosphere. The reaction solution was stirred at 80° C. for 4 hours. After the completion of the reaction detected by LCMS, the reaction solution was cooled to room temperature, and filtered, and the filtrate was concentrated under reduced pressure and purified by preparative liquid chromatography (Phenomenex Gemini C18 column, 3 μm silica, 30 mm in diameter, 75 mm in length); (using a decreasingly polar mixture of water (containing 0.225% formic acid) and acetonitrile as the eluent) to obtain the compound N-(1-(3-fluoropropyl)pyrrolidin-3-yl)-6-((1S,3R)-3-methyl-2-(2,2,2-trifluoroethyl)-2,3,4,9-tetrahydro-1H-pyridino[3,4-b]indol-1-yl)pyridine-3-amine (22.23 mg).

MS m/z (ESI): 490.2 $[M+H]^+$.

$^1$H NMR (400 MHz, METHANOL-$d_4$) δ 7.88 (d, J=2.76 Hz, 1H), 7.46 (d, J=7.78 Hz, 1H), 7.25 (dd, J=7.91, 3.89 Hz, 2H), 7.09-6.96 (m, 3H), 4.97 (s, 1H), 4.60 (t, J=5.65 Hz, 1H), 4.48 (t, J=5.65 Hz, 1H), 4.15 (br s, 1H), 3.52-3.36 (m, 3H), 3.25-3.14 (m, 1H), 3.09-2.88 (m, 6H), 2.68 (s, 1H), 2.51-2.39 (m, 1H), 2.11-1.85 (m, 3H), 1.20 (d, J=6.53 Hz, 3H).

Example 2: Synthesis of N—((R)(1-(3-fluoropropyl)pyrrolidin-3-yl)-6-((1S,3R)-3-methyl-2-(2,2,2-trifluoroethyl)-2,3,4,9-tetrahydro-1H-pyridino[3,4-b] indol-1-yl)pyridine-3-amine (Compound 2) and example 3: Synthesis of N—((S)(1-(3-fluoropropyl) pyrrolidin-3-yl)-6-((1S,3R)-3-methyl-2-(2,2,2-trifluoroethyl)-2,3,4,9-tetrahydro-1H-pyridino[3,4-b] indol-1-yl)pyridine-3-amine (Compound 3)

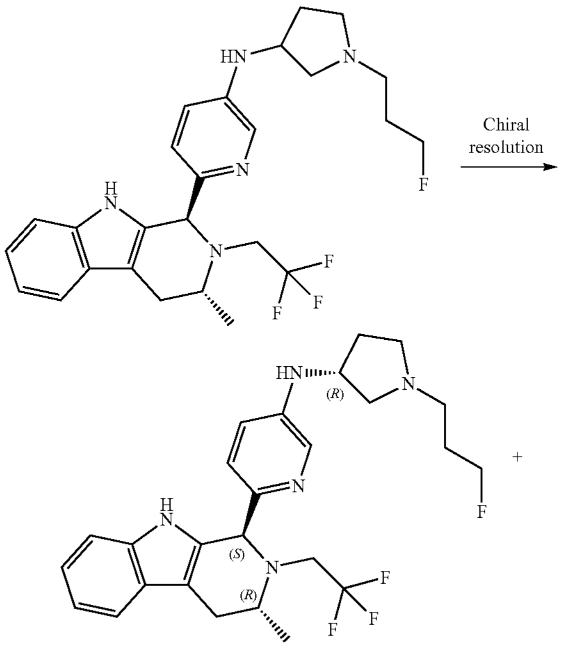

-continued

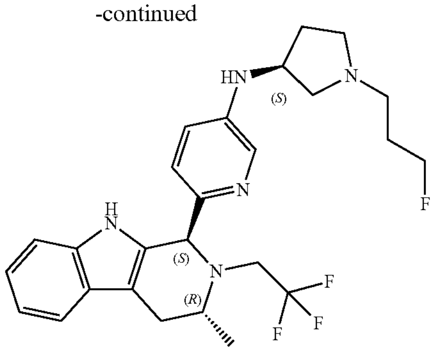

The racemate N-(1-(3-fluoropropyl)pyrrolidin-3-yl)-6-((1S,3R)-3-methyl-2-(2,2,2-trifluoroethyl)-2,3,4,9-tetrahydro-1H-pyridino[3,4-b]indol-1-yl)pyridine-3-amine (80.00 mg, 153.61 μmol) was subjected to chiral separation (DAICEL CHIRALPAK AY-H column, 5 m silica, 30 mm in diameter, 250 mm in length, using a decreasingly polar mixture of isopropanol (containing 0.1% ammonia water) and water as the eluent) and purified by preparative liquid chromatography (Phenomenex Gemini C18 Column, 3 m silica, 30 mm in diameter, 75 mm in length, using a decreasingly polar mixture of water (containing 0.05% ammonia water) and acetonitrile as the eluent) to obtain N—((R)(1-(3-fluoropropyl)pyrrolidin-3-yl)-6-((1S,3R)-3-methyl-2-(2,2,2-trifluoroethyl)-2,3,4,9-tetrahydro-1H-pyridino[3,4-b]indol-1-yl)pyridine-3-amine (8.22 mg, retention time of 2.627 min) and N—((S)(1-(3-fluoropropyl)pyrrolidin-3-yl)-6-((1S,3R)-3-methyl-2-(2,2,2-trifluoroethyl)-2,3,4,9-tetrahydro-1H-pyridino[3,4-b]indol-1-yl)pyridine-3-amine (10.85 mg, retention time of 2.817 min).

N—((R)(1-(3-fluoropropyl)pyrrolidin-3-yl)-6-((1S, 3R)-3-methyl-2-(2,2,2-trifluoroethyl)-2,3,4,9-tetrahydro-1H-pyridino[3,4-b]indol-1-yl)pyridine-3-amine (Compound 2)

MS m/z (ESI): 490.1 $[M+H]^+$ $^1$H NMR (400 MHz, METHANOL-$d_4$) δ 7.89 (d, J=2.76 Hz, 1H), 7.48-7.44 (m, 1H), 7.29-7.24 (m, 2H), 7.09-7.04 (m, 2H), 7.00 (s, 1H), 4.98 (s, 1H), 4.64-4.60 (m, 1H), 4.52-4.48 (m, 1H), 4.25-4.16 (m, 1H), 3.54-3.36 (m, 4H), 3.25-3.09 (m, 4H), 3.05 (s, 1H), 2.89 (d, J=4.52 Hz, 1H), 2.70-2.60 (m, 1H), 2.55-2.42 (m, 1H), 2.16-1.94 (m, 3H), 1.20 (d, J=6.78 Hz, 3H).

N—((S)(1-(3-fluoropropyl)pyrrolidin-3-yl)-6-((1S, 3R)-3-methyl-2-(2,2,2-trifluoroethyl)-2,3,4,9-tetrahydro-1H-pyridino[3,4-b]indol-1-yl)pyridine-3-amine (Compound 3)

MS m/z (ESI): 489.25, 490.1 $[M+H]^+$ $^1$H NMR (400 MHz, METHANOL-$d_4$) δ 7.90-7.88 (m, 1H), 7.48-7.43 (m, 1H), 7.29-7.23 (m, 2H), 7.09-7.03 (m, 2H), 7.03-6.97 (m, 1H), 4.99-4.97 (m, 1H), 4.63-4.59 (m, 1H), 4.52-4.47- (m, 1H), 4.24-4.16 (m, 1H), 3.52-3.36 (m, 4H), 3.15 (br s, 4H), 3.05-2.99 (m, 1H), 2.96-2.88 (m, 1H), 2.68 (s, 1H), 2.57-2.43 (m, 1H), 2.12-1.94 (m, 3H), 1.20 (d, J=6.53 Hz, 3H).

N—((S)-1-(3-fluoropropyl)pyrrolidin-3-yl)-6-((1S,3R)-3-methyl-2-(2,2,2-trifluoroethyl)-2,3,4,9-tetrahydro-1H-pyridino[3,4-b]indol-1-yl)pyridine-3-amine (compound 3) can also be obtained by the following synthetic method:

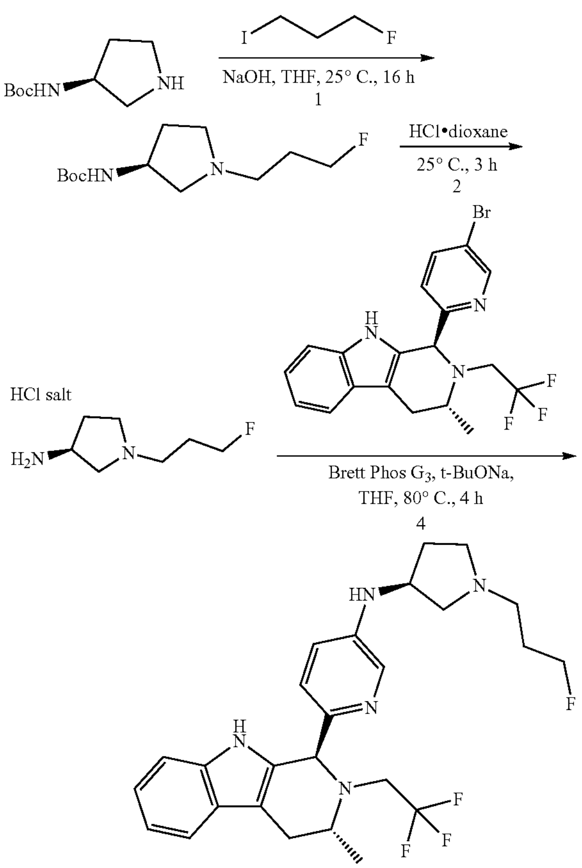

Step 1: Synthesis of (S)-tert-butyl(1-(3-fluoropropyl)pyrrolidin-3-yl)carbamate

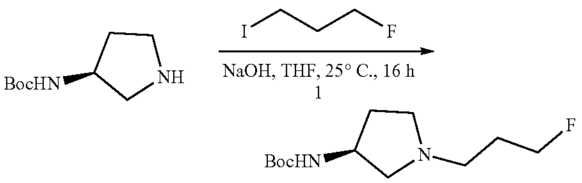

(S)-tert-butyl pyrrolidin-3-ylcarbamate (500.00 mg, 2.68 mmol) was dissolved in tetrahydrofuran (10 mL), and sodium hydroxide solution (5 mol·$L^{-1}$, 1.07 mL) and 1-iodo-3-fluoropropane (529.88 mg, 2.82 mmol) were added. The reaction solution was stirred at 25° C. for 16 hours. After completion of the reaction of the raw materials detected by TLC, the reaction solution was diluted with ethyl acetate (50 mL), and then washed with saturated ammonium chloride solution (10 mL), and the aqueous phase and the organic phase were collected separately. The aqueous phase was extracted with ethyl acetate (20 mL) three times, and then all organic phases were combined and dried over sodium sulfate, and the organic phase was concentrated to dryness under reduced pressure, and then purified by column chromatography (silica, dichloromethane/methanol=100/1) to obtain the product (S)-tert-butyl(1-(3-fluoropropyl)pyrrolidin-3-yl)carbamate (480.00 mg).

$^1$H NMR (400 MHz, METHANOL-$d_4$) δ 4.58-4.53 (m, 1H), 4.46-4.40 (m, 1H), 4.14-4.04 (m, 1H), 2.93-2.85 (m, 1H), 2.77-2.67 (m, 1H), 2.61 (dd, J=7.78, 5.52 Hz, 3H), 2.47-2.40 (m, 1H), 2.29-2.17 (m, 1H), 1.99-1.82 (m, 2H), 1.71-1.61 (m, 1H), 1.45 (s, 9H).

Step 2: Synthesis of (S)-1-(3-fluoropropyl)pyrrolidin-3-amine hydrochloride

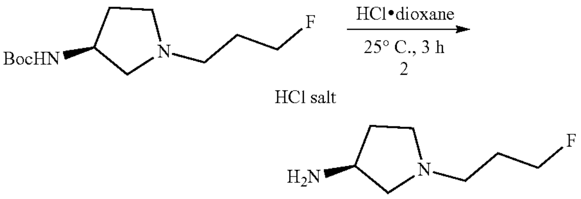

(S)-tert-butyl(1-(3-fluoropropyl)pyrrolidin-3-yl)carbamate (480.00 mg, 1.93 mmol) was dissolved in 1,4-dioxane (3 mL), and then hydrochloric acid-1,4-dioxane solution (4 moL·$L^{-1}$, 4.94 mL) was added, and the reaction solution was a yellow transparent solution. The reaction solution was stirred at 25° C. for 3 hours. After completion of the reaction of the raw materials detected by TLC, the reaction solution was concentrated under reduced pressure to obtain a compound (S)-1-(3-fluoropropyl)pyrrolidin-3-amine hydrochloride (450.00 mg).

$^1$H NMR (400 MHz, DMSO-$d_6$) δ 8.80-8.42 (m, 3H), 4.62 (s, 1H), 4.51 (s, 1H), 4.12-3.45 (m, 3H), 3.17 (br s, 3H), 2.35-1.99 (m, 4H).

Step 3: Synthesis of N—((S)-1-(3-fluoropropyl)pyrrolidin-3-yl)-6-((1S,3R)-3-methyl-2-(2,2,2-trifluoroethyl)-2,3,4,9-tetrahydro-1H-pyridino[3,4-b]indol-1-yl)pyridine-3-amine

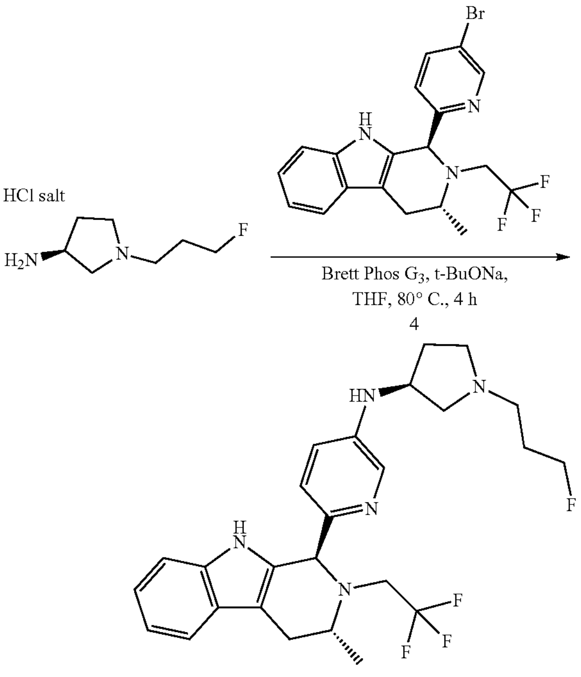

(1S,3R)-1-(5-bromopyridin-2-yl)-3-methyl-2-(2,2,2-trifluoroethyl)-2,3,4,9-tetrahydro-1H-pyridino[3,4-b]indole (140.00 mg, 263.99 μmol) was dissolved in tetrahydrofuran (3 mL), and (S)-1-(3-fluoropropyl)pyrrolidin-3-amine hydrochloride (86.77 mg, 316.79 μmol), sodium tert-butoxide (152.22 mg, 1.58 mmol) and methanesulfonic acid(2-dicyclohexylphosphino)-3, 6-dimethoxyl-2,4,6-triisopropyl-1,1-biphenyl)(2-amino-1,1-biphenyl-2-yl)palladium(II) (23.93 mg, 26.40 μmol) were added, and the reaction solution was stirred at 80° C. under nitrogen atmosphere for 4 hours. After the completion of the reaction detected by LCMS, the reaction solution was cooled to room temperature, and filtered, and the filtrate was concentrated under reduced pressure and purified by preparative liquid chromatography (Phenomenex Gemini C18 column, 3 μm silica, 30 mm in diameter, 75 mm in length); (using a decreasingly polar mixture of water (containing 0.225% formic acid) and acetonitrile as the eluent) to obtain the compound N—((S)-1-(3-fluoropropyl)pyrrolidin-3-yl)-6-((1S,3R)-3-methyl-2-(2,2,2-trifluoroethyl)-2,3,4,9-tetrahydro-1H-pyridino[3,4-b]indol-1-yl)pyridine-3-amine (37.79 mg).

MS m/z (ESI): 365.1 $[M+H]^+$ $^1H$ NMR (400 MHz, METHANOL-$d_4$) δ 7.89 (d, J=2.76 Hz, 1H), 7.46 (d, J=7.78 Hz, 1H), 7.25 (d, J=8.53 Hz, 2H), 7.09-7.03 (m, 2H), 7.02-6.97 (m, 1H), 4.98 (s, 1H), 4.60 (t, J=5.65 Hz, 1H), 4.49 (t, J=5.65 Hz, 1H), 4.18 (br s, 1H), 3.51-3.35 (m, 4H), 3.14-2.99 (m, 5H), 2.92 (dd, J=15.18, 4.89 Hz, 1H), 2.65 (dd, J=16.06, 6.78 Hz, 1H), 2.53-2.42 (m, 1H), 2.12-1.92 (m, 3H), 1.20 (d, J=6.78 Hz, 3H).

Identification of Absolute Configuration of Compound 3

Identification by 2D NMR:

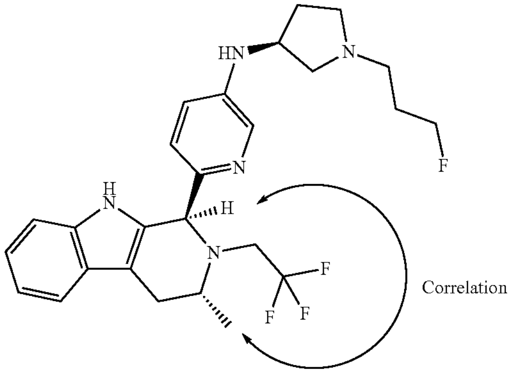 [SMILES: C[C@@H]1Cc2c([nH]c3ccccc23)[C@@H](c2ccc(N[C@H]3CCN(CCCF)C3)cn2)N1CC(F)(F)F]

The NOESY spectrum (FIG. 1) shows that the methyl hydrogen at the position 3 of compound 3 has an obvious NOE effect with the hydrogen at the position 1, which proves that the two are on the same side, and the relative configuration of the pyridyl at the position 1 and the methyl at the position 3 on the 6-membered piperidine ring is trans, and the absolute configuration of the carbon atom at the position 3 is known to be of R, and therefore the absolute configuration of the carbon atom at the position 1 is of S.

Example 4: Synthesis of (S)—N-(3,5-difluoro-4-((1S,3R)-3-methyl-2-(2,2,2-trifluoroethyl)-2,3,4,9-tetrahydro-1H-pyridino[3,4-b]indol-1-yl)phenyl)-1-(3-fluoropropyl)pyrrolidin-3-amine (Compound 4)

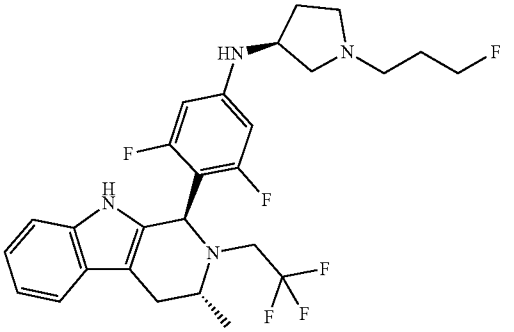 [SMILES: C[C@@H]1Cc2c([nH]c3ccccc23)[C@@H](c2c(F)cc(N[C@H]3CCN(CCCF)C3)cc2F)N1CC(F)(F)F]

Synthesis Method:

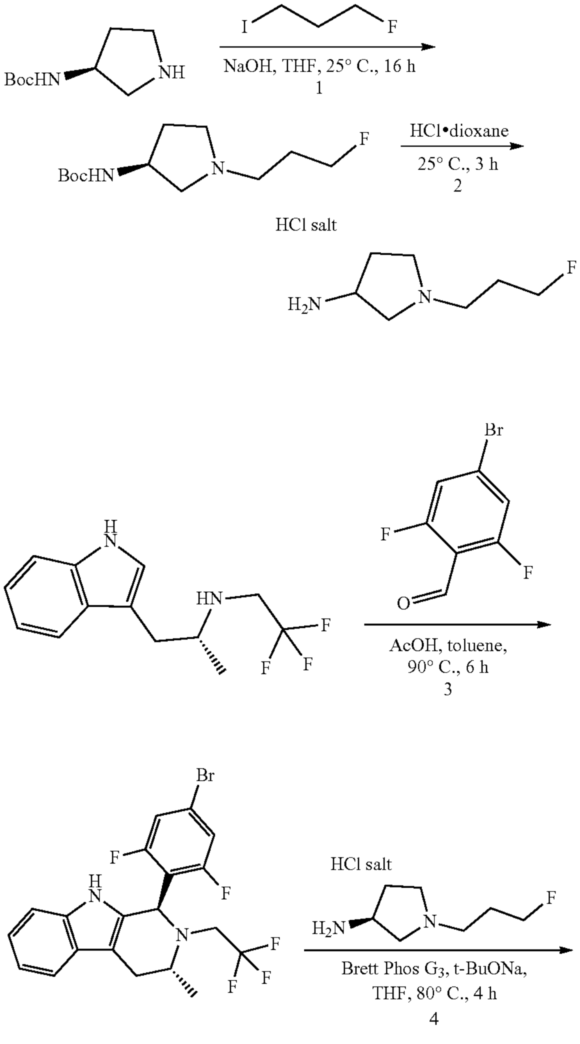

-continued

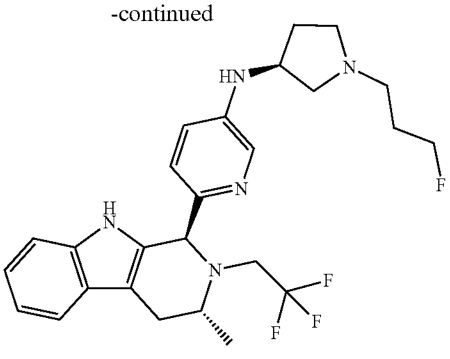

Step 1: Synthesis of (S)-tert-butyl(1-(3-fluoropropyl)pyrrolidin-3-yl)carbamate

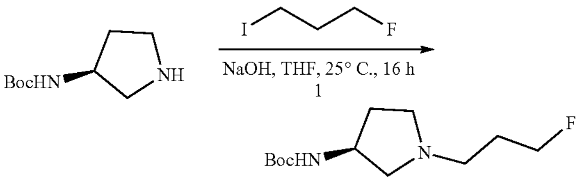

(S)-tert-butyl pyrrolidin-3-ylcarbamate (500.00 mg, 2.68 mmol) was dissolved in tetrahydrofuran (10 mL), and sodium hydroxide solution (5 mol·L$^{-1}$, 1.07 mL) and 1-iodo-3-fluoropropane (529.88 mg, 2.82 mmol) were added. The reaction solution was stirred at 25° C. for 16 hours. After completion of the reaction of the raw materials detected by TLC, the reaction solution was diluted with ethyl acetate (50 mL), and then washed with saturated ammonium chloride solution (10 mL), and the aqueous phase and the organic phase were collected separately. The aqueous phase was extracted with ethyl acetate (20 mL) three times, and then all organic phases were combined and dried over sodium sulfate, and the organic phase was concentrated to dryness under reduced pressure, and then purified by column chromatography (silica, dichloromethane/methanol=100/1) to obtain the product (S)-tert-butyl(1-(3-fluoropropyl)pyrrolidin-3-yl)carbamate (480.00 mg).

$^{1}$H NMR (400 MHz, METHANOL-d$_4$) δ 4.58-4.53 (m, 1H), 4.46-4.40 (m, 1H), 4.14-4.04 (m, 1H), 2.93-2.85 (m, 1H), 2.77-2.67 (m, 1H), 2.61 (dd, J=7.78, 5.52 Hz, 3H), 2.47-2.40 (m, 1H), 2.29-2.17 (m, 1H), 1.99-1.82 (m, 2H), 1.71-1.61 (m, 1H), 1.45 (s, 9H).

Step 2: Synthesis of (S)-1-(3-fluoropropyl)pyrrolidin-3-amine hydrochloride

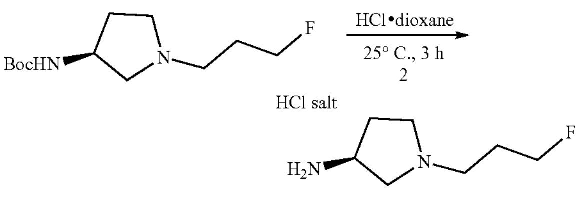

(S)-tert-butyl(1-(3-fluoropropyl)pyrrolidin-3-yl)carbamate (480.00 mg, 1.93 mmol) was dissolved in 1,4-dioxane (3 mL), and then hydrochloric acid-1,4-dioxane solution (4 moL·L$^{-1}$, 4.94 mL) was added, and the reaction solution was a yellow transparent solution. The reaction solution was stirred at 25° C. for 3 hours. After completion of the reaction of the raw materials detected by TLC, the reaction solution was concentrated under reduced pressure to obtain a compound (S)-1-(3-fluoropropyl)pyrrolidin-3-amine hydrochloride (450.00 mg).

$^{1}$H NMR (400 MHz, DMSO-d$_6$) δ 8.80-8.42 (m, 3H), 4.62 (s, 1H), 4.51 (s, 1H), 4.12-3.45 (m, 3H), 3.17 (br s, 3H), 2.35-1.99 (m, 4H).

Step 3: Synthesis of (1S,3R)-1-(4-bromo-2,6-difluorophenyl)-3-methyl-2-(2,2,2-trifluoroethyl)-2,3,4,9-tetrahydro-1H-pyridino[3,4-b]indole

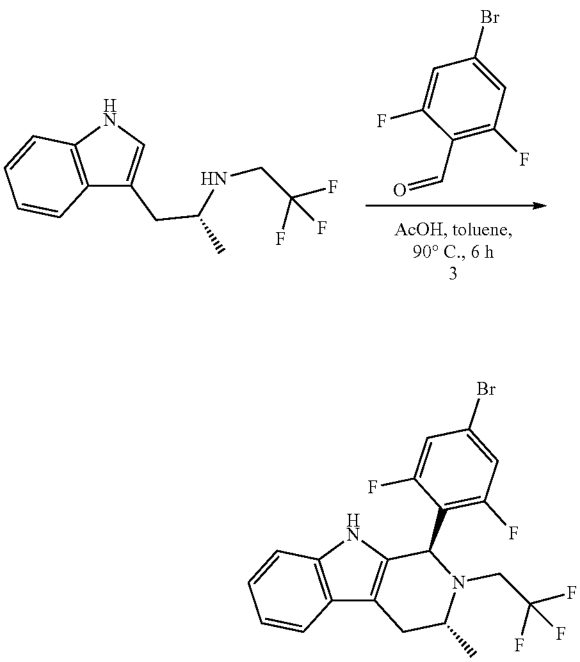

(R)-1-(1H-indol-3-yl)-N-(2,2,2-trifluoroethyl)propane-2-amine (890 mg, 3.47 mmol) and 4-bromo-2,6-difluorobenzaldehyde (844.27 mg, 3.82 mmol) were dissolved in toluene (10 mL) and acetic acid (2 mL), and the reaction solution was stirred at 90° C. for 6 hours. The reaction solution was concentrated to dryness under reduced pressure. Then, the reaction solution was purified by column chromatography (silica, petroleum ether/ethyl acetate=20/1) to obtain the product (1S,3R)-1-(4-bromo-2,6-difluorophenyl)-3-methyl-2-(2,2,2-trifluoroethyl)-2,3,4,9-tetrahydro-1H-pyridino[3,4-b]indole (850 mg).

$^{1}$H NMR (400 MHz, METHANOL-d$_4$) δ 7.45-7.43 (d, J=7.60 Hz, 1H), 7.24-7.20 (m, 3H), 7.05-6.99 (m, 2H), 5.36 (s, 1H), 3.57-3.54 (m, 1H), 3.46-3.40 (m, 1H), 3.01-2.95 (m, 2H), 2.70-2.65 (m, 1H), 1.20 (d, J=6.4 Hz, 3H).

Step 4: Synthesis of (S)—N-(3,5-difluoro-4-((1S, 3R)-3-methyl-2-(2,2,2-trifluoroethyl)-2,3,4,9-tetrahydro-1H-pyridino[3,4-b]indol-1-yl)phenyl)-1-(3-fluoropropyl)pyrrolidin-3-amine

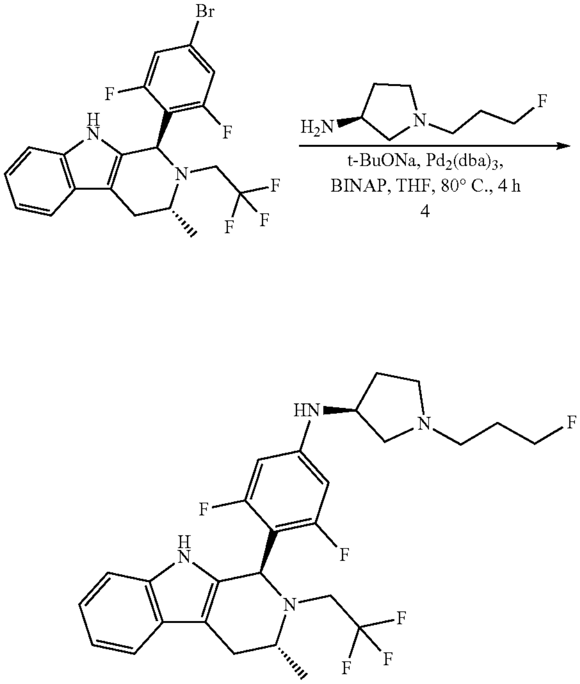

(1S,3R)-1-(4-bromo-2,6-difluorophenyl)-3-methyl-2-(2,2,2-trifluoroethyl)-2,3,4,9-tetrahydro-1H-pyridyl[3,4-b]indole (80.00 mg, 174.20 μmol) was dissolved in tetrahydrofuran (2 mL), and (S)-1-(3-fluoropropyl)pyrrolidin-3-amine hydrochloride (38.20 mg, 209.04 μmol) and sodium tert-butoxide (100.45 mg, 1.05 mmol) were added, the mixture was stirred uniformly, and then tris(dibenzalacetone)dipalladium (31.90 mg, 34.84 μmol) and (±)-2,2-dis(diphenylphosphino)-11-binaphthyl (54.23 mg, 87.10 μmol) were added under nitrogen atmosphere. The reaction solution was stirred and reacted at 80° C. for 4 hours. After completion of the reaction of the raw materials detected by LCMS, the reaction solution was filtered, and then the filter cake was rinsed with tetrahydrofuran, and the filtrate was concentrated to dryness under reduced pressure, and purified by preparative liquid chromatography (Phenomenex Gemini C18 column, 7 m silica, 50 mm in diameter, 250 mm in length, using a decreasingly polar mixture of water (containing 0.225% formic acid) and acetonitrile as the eluent) to obtain the compound (S)—N-(3,5-difluoro-4-((1S,3R)-3-methyl-2-(2,2,2-trifluoroethyl)-2,3,4,9-tetrahydro-1H-pyridino[3,4-b]indol-1-yl)phenyl)-1-(3-fluoropropyl)pyrrolidin-3-amine (4.69 mg).

MS m/z (ESI): 525.2 $[M+H]^+$ $^1H$ NMR (400 MHz, METHANOL-$d_4$) δ 8.49 (s, 1H), 7.42 (d, J=7.3 Hz, 1H), 7.21 (d, J=7.8 Hz, 1H), 7.08-6.94 (m, 2H), 6.19 (d, J=11.5 Hz, 2H), 5.24 (s, 1H), 4.60 (t, J=5.6 Hz, 1H), 4.48 (t, J=5.6 Hz, 1H), 4.11 (br s, 1H), 3.62-3.53 (m, 1H), 3.21 (br s, 1H), 3.09-2.94 (m, 6H), 2.63 (dd, J=15.3, 4.3 Hz, 1H), 2.51-2.38 (m, 1H), 2.12-1.99 (m, 2H), 1.96-1.85 (m, 1H), 1.39-1.29 (m, 2H), 1.19 (d, J=6.5 Hz, 3H).

Example 5: Synthesis of trans-N-(3,5-difluoro-4-((1S,3R)-3-methyl-2-(2,2,2-trifluoroethyl)-2,3,4,9-tetrahydro-1H-pyridino[3,4-b]indol-1-yl)phenyl)-4-fluoro-1-(3-fluoropropyl)pyrrolidin-3-amine (compound 5)

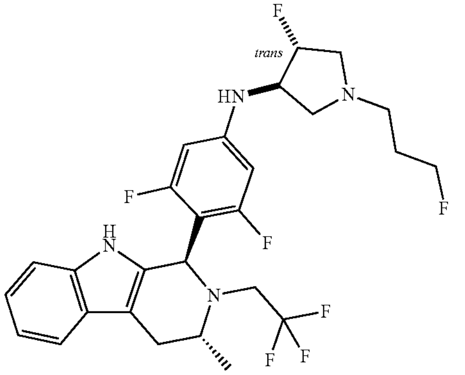 [SMILES: C[C@@H]1Cc2c([nH]c3ccccc23)[C@@H](c2c(F)cc(N[C@@H]3CN(CCCF)C[C@H]3F)cc2F)N1CC(F)(F)F]

Synthesis Method:

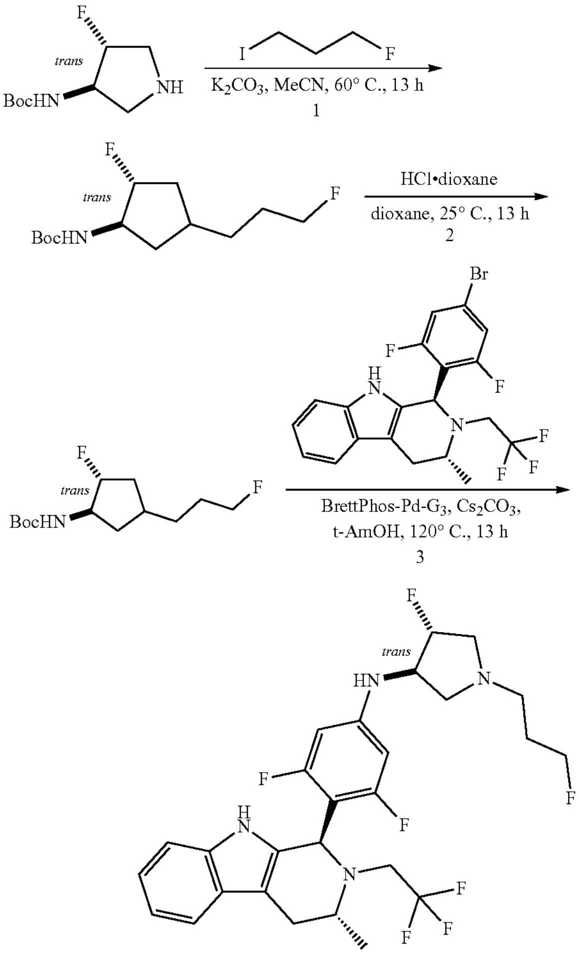

Step 1: Synthesis of tert-butyl(trans-4-fluoro-1-(3-fluoropropyl)pyrrolidin-3-yl)carbamate

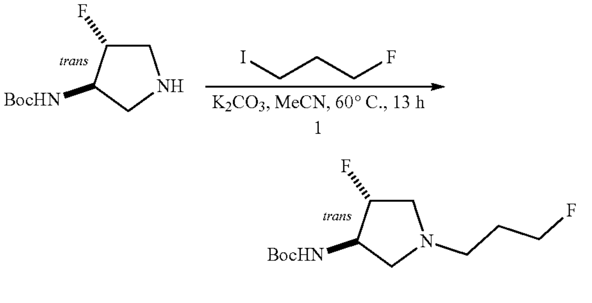

1-Fluoro-3-iodopropane (151.86 mg, 807.87 μmol) and tert-butyl(trans-4-fluoropyrrolidin-3-yl)carbamate (150 mg, 734.43 μmol) were dissolved in acetonitrile (4 mL), potassium carbonate (203.00 mg, 1.47 mmol) was added at 25° C., and the reaction solution was stirred at 60° C. for 13 hours. The reaction solution was cooled to 25° C., filtered, and concentrated to dryness under reduced pressure. Then, the crude product was purified by column chromatography (silica, ethyl acetate/methanol=10/1) to obtain the product tert-butyl(trans-4-fluoro-1-(3-fluoropropyl)pyrrolidin-3-yl) carbamate (0.15 g).

MS m/z (ESI): 265.0 $[M+H]^+$;

$^1$H NMR (400 MHz, CHLOROFORM-d) δ 4.87 (br s, 1H), 4.59 (t, J=5.9 Hz, 1H), 4.48 (t, J=5.9 Hz, 1H), 4.16 (br s, 1H), 3.29-3.05 (m, 1H), 3.01-2.87 (m, 1H), 2.78-2.41 (m, 4H), 2.02-1.81 (m, 2H), 1.48 (s, 9H).

Step 2: Synthesis of trans-4-fluoro-1-(3-fluoropropyl)pyrrolidin-3-amine hydrochloride

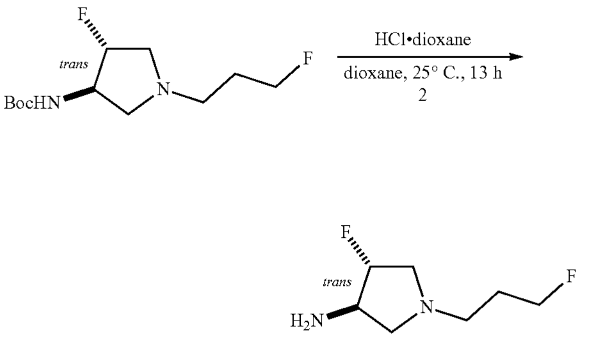

Tert-butyl((trans-4-fluoro-1-(3-fluoropropyl)pyrrolidin-3-yl)carbamate (150 mg, 567.51 μmol) was dissolved in 1,4-dioxane (2 mL), 4M dioxane hydrochloride (2.13 mL) was added, and the reaction solution was stirred and reacted at 25° C. for 13 hours. The reaction solution was concentrated to obtain the product trans-4-fluoro-1-(3-fluoropropyl)pyrrolidin-3-amine hydrochloride (0.12 g).

MS m/z (ESI): 165.2$[M+H]^+$.

Step 3: Synthesis of trans-N-(3,5-difluoro-4-((1S,3R)-3-methyl-2-(2,2,2-trifluoroethyl)-2,3,4,9-tetrahydro-1H-pyridino[3,4-b]indol-1-yl)phenyl)-4-fluoro-1-(3-fluoropropyl)pyrrolidin-3-amine

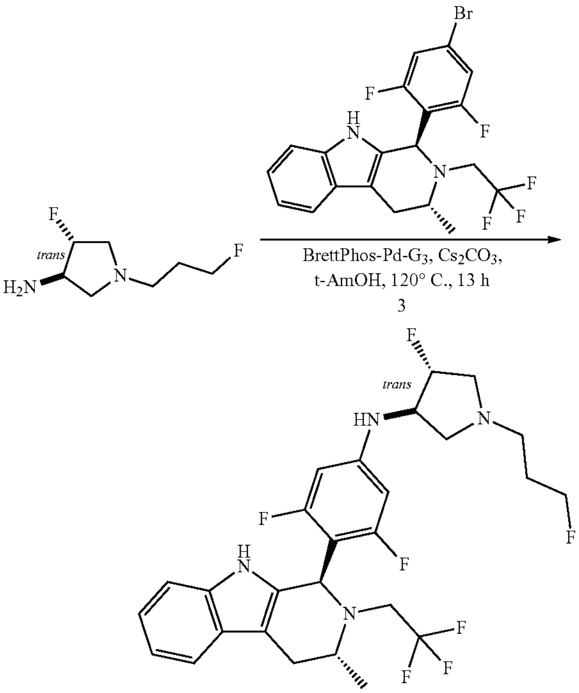

(1S,3R)-1-(4-bromo-2,6-difluorophenyl)-3-methyl-2-(2,2,2-trifluoroethyl)-2,3,4,9-tetrahydro-1H-pyridino[3,4-b]indole (140 mg, 304.84 μmol) and trans-4-fluoro-1-(3-fluoropropyl)pyrrolidin-3-amine hydrochloride (86.74 mg, 365.81 μmol) were dissolved in tertiary pentanol (5 mL), and methanesulfonic acid(2-dicyclohexylphosphino-3,6-dimethoxyl-2,4,6-triisopropyl-1,1-biphenyl)(2-amino-1,1-biphenyl-2-yl)palladium(II) (25.50 mg, 30.48 mol) and cesium carbonate (595.95 mg, 1.83 mmol) were added. After being replaced with nitrogen three times, the reaction solution was stirred at 120° C. for 13 hours. The reaction solution was cooled to room temperature and poured into water (10 mL), the solution was stirred for 10 minutes and extracted twice with ethyl acetate (20 mL), and the organic phase was dried over anhydrous sodium sulfate, filtered, and concentrated to dryness under reduced pressure. Then, the crude product was purified by column chromatography (silica, petroleum ether/ethyl acetate=2/1) and preparative liquid chromatography (PhenomenexGemini-NX column, 3 m silica, 30 mm in diameter, 75 mm in length, using a decreasingly polar mixture of water (containing 0.05% ammonia water) and acetonitrile as the eluent) to obtain the product trans-N-(3,5-difluoro-4-((1S,3R)-3-methyl-2-(2,2,2-trifluoroethyl)-2,3,4,9-tetrahydro-1H-pyridino[3,4-b]indol-1-yl)phenyl)-4-fluoro-1-(3-fluoropropyl)pyrrolidin-3-amine (27.5 mg).

MS m/z (ESI): 543.1 $[M+H]^+$;

$^1$H NMR (400 MHz, METHANOL-d$_4$) δ 7.42 (d, J=7.5 Hz, 1H), 7.22 (d, J=7.5 Hz, 1H), 7.09-6.93 (m, 2H), 6.30-6.16 (m, 2H), 5.25 (s, 1H), 4.58 (t, J=5.8 Hz, 1H), 4.46 (t, J=5.8 Hz, 1H), 4.11-3.87 (m, 1H), 3.67-3.53 (m, 1H), 3.43-3.34 (m, 3H), 3.19-2.92 (m, 3H), 2.81-2.55 (m, 4H), 2.29 (dd, J=6.9, 9.7 Hz, 1H), 2.02-1.83 (m, 2H), 1.19 (d, J=6.4 Hz, 3H).

Example 6: Synthesis of trans-N-[3,5-difluoro-4-[(1S,3R)-3-methyl-2-(2,2,2-trifluoroethyl)-1,3,4,9-tetrahydropyridino[3,4-b]indol-1-yl]phenyl]-1-(3-fluoropropyl)-4-methyl-pyrrolidin-3-amine (compound 6)

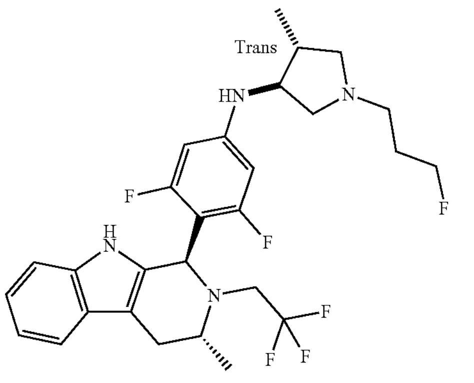 [SMILES: C[C@@H]1CN(CCCF)C[C@H]1Nc1cc(F)c([C@@H]2c3[nH]c4ccccc4c3C[C@@H](C)N2CC(F)(F)F)c(F)c1]

Synthesis Method:

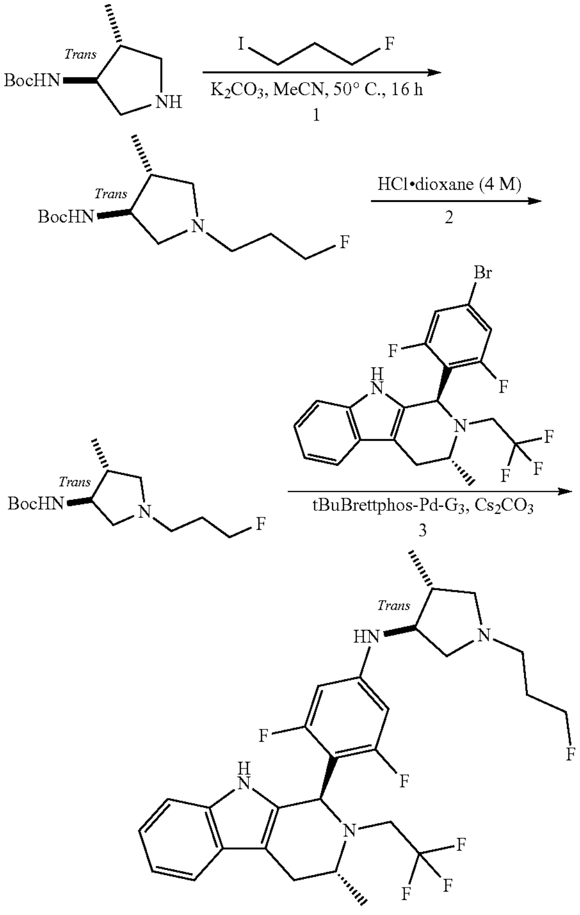

Step 1: Synthesis of tert-butyl N-[trans-1-(3-fluoropropyl)-4-methyl-pyrrolidin-3-yl]carbamate

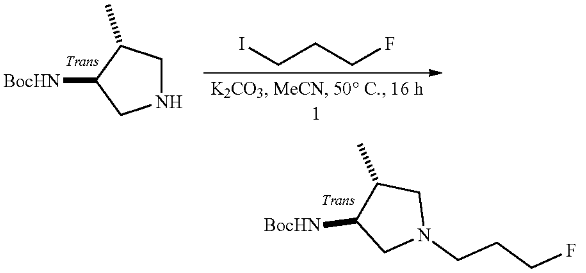

Tert-butyl N-[trans-4-methylpyrrolidin-3-yl]carbamate (80 mg, 399.45 μmol) and potassium carbonate (110.41 mg, 798.89 μmol) were dissolved in acetonitrile (8 mL), and then 1-fluoro-3-iodo-propane (90.11 mg, 479.34 μmol) was added, and the reaction solution was heated to 50° C. and stirred for 16 h. The completion of the reaction was monitored by LCMS. The reaction solution was filtered, and the filtrate was concentrated to dryness and purified by column chromatography (silica, ethyl acetate/methanol=5/1) to obtain the compound tert-butyl N-[trans-1-(3-fluoropropyl)-4-methyl-pyrrolidin-3-yl]carbamate (85 mg).

MS m/z (ESI): 261.1[M+H]$^+$ $^1$H NMR (400 MHz, METHANOL-$d_4$) δ 4.66 (br d, J=2.4 Hz, 1H), 4.61-4.42 (m, 2H), 4.05-3.93 (m, 1H), 3.71-3.56 (m, 2H), 3.17 (br d, J=9.4 Hz, 1H), 2.90 (br s, 2H), 2.54 (br s, 1H), 2.19 (br d, J=5.2 Hz, 2H), 2.07-1.89 (m, 1H), 1.47 (s, 9H), 1.24-1.11 (m, 3H).

Step 2: Synthesis of trans-1-(3-fluoropropyl)-4-methyl-pyrrolidin-3-amine hydrochloride

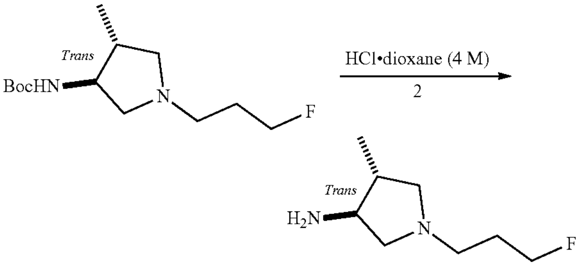

Tert-butyl N-[trans-1-(3-fluoropropyl)-4-methyl-pyrrolidin-3-yl]carbamate (80 mg, 307.28 μmol) was dissolved in dioxane (2 mL), and then 4M dioxane hydrochloride (1.54 mL) was added, and the reaction solution was stirred at room temperature overnight. The reaction solution was concentrated to dryness to obtain the compound trans-1-(3-fluoropropyl)-4-methyl-pyrrolidin-3-amine hydrochloride (70 mg).

$^1$H NMR (400 MHz, METHANOL-$d_4$) δ 4.73-4.64 (m, 1H), 4.61-4.50 (m, 1H), 4.23-4.06 (m, 1H), 4.02-3.63 (m, 5H), 3.54-3.42 (m, 1H), 3.01-2.58 (m, 1H), 2.32-2.12 (m, 2H), 1.37-1.27 (m, 3H).

Step 3: Synthesis of trans-N-[3,5-difluoro-4-[(1S, 3R)-3-methyl-2-(2,2,2-trifluoroethyl)-1,3,4,9-tetrahydropyridino[3,4-b]indol-1-yl]phenyl]-1-(3-fluoropropyl)-4-methyl-pyrrolidin-3-amine

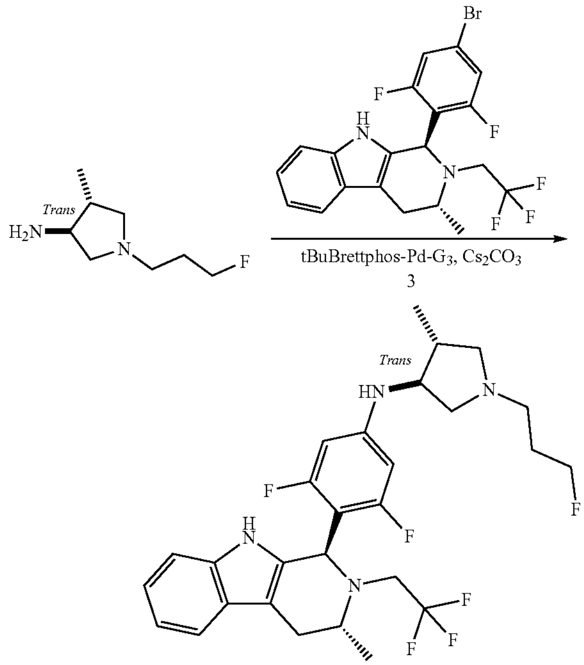

Trans-1-(3-fluoropropyl)-4-methyl-pyrrolidin-3-amine hydrochloride (30 mg, 128.67 μmol), (1S,3R)-1-(4-bromo-2,6-difluoro-phenyl)-3-methyl-2-(2,2,2-trifluoroethyl)-1,3,4,9-tetrahydropyridino[3,4-b]indole (76.82 mg, 167.27 μmol) and cesium carbonate (167.69 mg, 514.68 μmol) were dissolved in dioxane (8 mL), and then tBuBrettphos-Pd-G3 (5.50 mg, 6.43 μmol) was added. The reaction solution was replaced with nitrogen three times, then heated to 120° C. and stirred overnight. The completion of the reaction was monitored by LCMS. Methanol (15 mL) was added to the reaction solution, the mixture was filtered, and the filtrate was concentrated and purified by column chromatography (silica, petroleum ether/ethyl acetate=2/1) and preparative liquid chromatography (Phenomenex Synergi C18 column, 4 m silica, 30 mm in diameter, 150 mm in length, using a decreasingly polar mixture of water (containing 0.225% formic acid) and acetonitrile as the eluent) to obtain the compound trans-N-[3,5-difluoro-4-[(1S,3R)-3-methyl-2-(2,2,2-trifluoroethyl)-1,3,4,9-tetrahydropyridino[3,4-b]indol-1-yl]phenyl]-1-(3-fluoropropyl)-4-methyl-pyrrolidin-3-amine (1.35 mg).

MS m/z (ESI): 539.3 $[M+H]^+$;

$^1H$ NMR (400 MHz, METHANOL-$d_4$) δ 7.42 (d, J=7.6 Hz, 1H), 7.21 (d, J=8.8 Hz, 1H), 7.08-6.86 (m, 2H), 6.21 (d, J=11.6 Hz, 2H), 5.24 (s, 1H), 4.62-4.58 (m, 1H), 4.52-4.45 (m, 1H), 3.73-3.65 (m, 1H), 3.62-3.47 (m, 3H), 3.23-3.15 (m, 2H), 3.08-2.95 (m, 2H), 2.86-2.54 (m, 2H), 2.41-2.00 (m, 3H), 1.42-1.25 (m 2H), 1.23 (dd, J=3.2, Hz, 6.8 Hz, 3H), 1.19 (d, J=6.4 Hz, 3H).

Example 7: Synthesis of 3-((1S,3R)-1-(2,6-difluoro-4-(((S)-1-(3-fluoropropyl)pyrrolidin-3-yl)amino)phenyl)-3-methyl-3,4-dihydro-1H-pyridino[3,4-b]indole-2(9H)-yl)-2,2-difluoropropane-1-ol

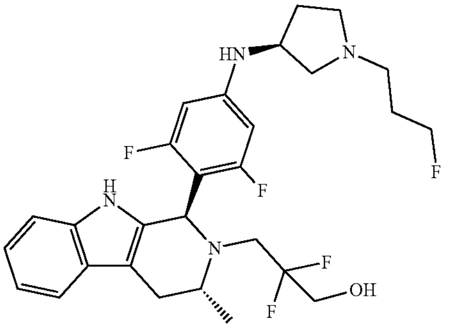 [SMILES: C[C@@H]1Cc2c([nH]c3ccccc23)[C@@H](c2c(F)cc(N[C@H]3CCN(CCCF)C3)cc2F)N1CC(F)(F)CO]

Synthesis Method

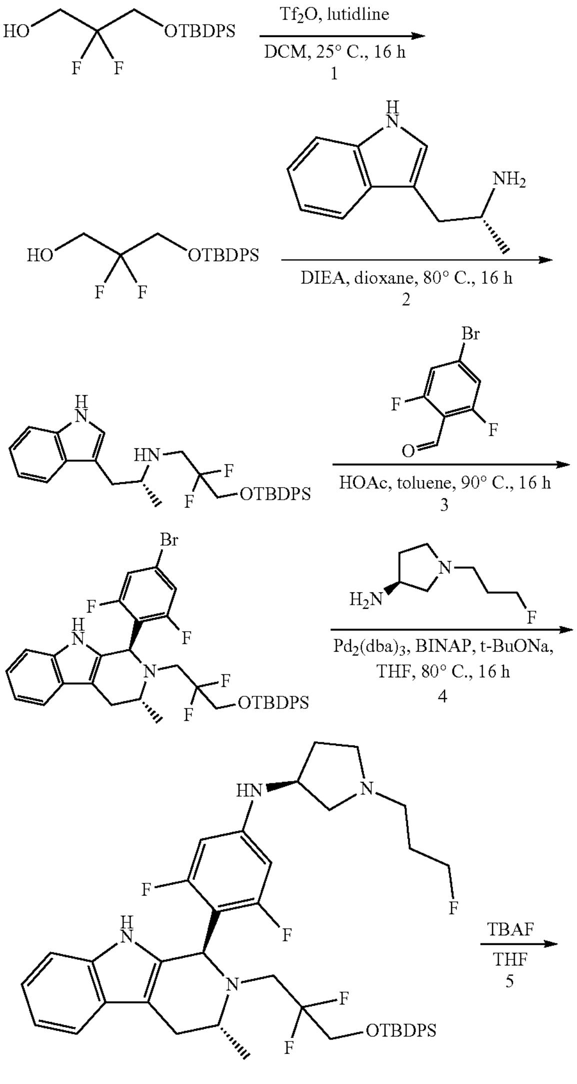

-continued

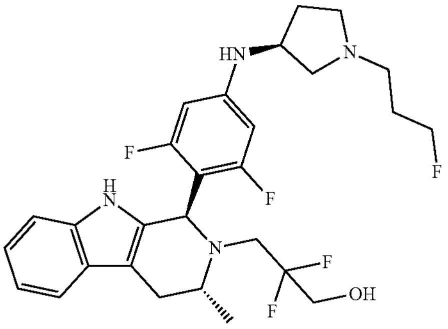

Step 1: Synthesis of 3-((tert-butyldiphenylsilyl)oxy)-2,2-difluoropropyl trifluoromethanesulfonate

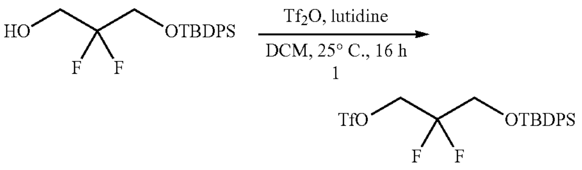

3-((tert-butyldiphenylsilyl)oxy)-2,2-difluoropropane-1-ol (1 g, 2.85 mmol) and 2,6-dimethylpyridine (366.88 mg, 3.42 mmol) were dissolved in anhydrous dichloromethane (15 mL), and trifluoromethanesulfonic anhydride (885.52 mg, 3.14 mmol) was added dropwise in an ice-water bath. The reaction solution was stirred at 25° C. for 16 hours. After the completion of the reaction monitored by TLC (silica, petroleum ether:ethyl acetate=10:1), the reaction solution was washed successively with water (10 mL), hydrochloric acid (1 mol/L, 10 mL) and saturated sodium carbonate solution (10 mL). After the collected organic phase was dried with sodium sulfate, the organic phase was concentrated to dryness under reduced pressure, and then purified by column chromatography (silica, petroleum ether/ethyl acetate=100/15) to obtain the product 3-((tert-butyldiphenylsilyl)oxy)-2,2-difluoropropyl trifluoromethanesulfonate (880.00 mg).

$^1$H NMR (400 MHz, METHANOL-$d_4$) δ 7.66 (d, J=7.0 Hz, 4H), 7.50-7.36 (m, 6H), 4.96 (t, J=12.2 Hz, 2H), 3.90 (t, J=12.0 Hz, 2H), 1.06 (s, 9H).

Step 2: Synthesis of (R)—N-(1-(1H-indol-3-yl)prop-2-yl)-3-((tert-butyldiphenylsilyl)oxy)-2,2-difluoroprop-1-amine

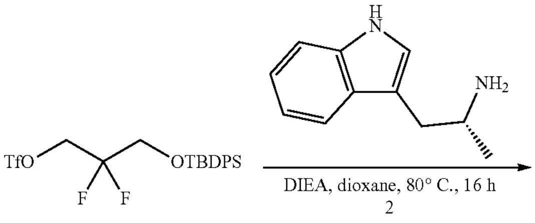

-continued

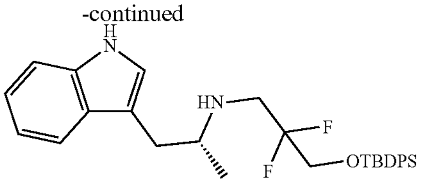

3-((tert-butyldiphenylsilyl)oxy)-2,2-difluoropropyl trifluoromethanesulfonate (822.49 mg, 1.70 mmol) and (R)-1-(1H-indol-3-yl)propane-2-amine (270 mg, 1.55 mmol) were dissolved in 1,4-dioxane (10 mL), and then N-ethyl-N-isopropyl propane-2-amine (600.81 mg, 4.65 mmol) was added. The reaction solution was stirred and reacted at 80° C. for 16 hours. The completion of the reaction was monitored by LCMS, and the reaction solution was concentrated and purified by column chromatography (silica, petroleum ether/ethyl acetate=100/17) to obtain the product (R)—N-(1-(1H-indol-3-yl)prop-2-yl)-3-((tert-butyldiphenylsilyl)oxy)-2,2-difluoroprop-1-amine (662.00 mg).

MS m/z (ESI): 507.2 $[M+H]^+$;

$^1$H NMR (400 MHz, CHLOROFORM-d) δ 7.72-7.63 (m, 4H), 7.61 (d, J=7.9 Hz, 1H), 7.49-7.33 (m, 7H), 7.20 (dt, J=1.1, 7.6 Hz, 1H), 7.14-7.09 (m, 1H), 7.01 (d, J=2.3 Hz, 1H), 3.89-3.76 (m, 2H), 3.27-3.05 (m, 3H), 2.94-2.77 (m, 2H), 1.13 (d, J=6.3 Hz, 3H), 1.06 (s, 9H).

Step 3: Synthesis of (1S,3R)-1-(4-bromo-2,6-difluorophenyl)-2-(3-((tert-butyldiphenylsilyl)oxy)-2,2-difluoropropyl)-3-methyl-2,3,4,9-tetrahydro-1H-pyridino[3,4-b]indole

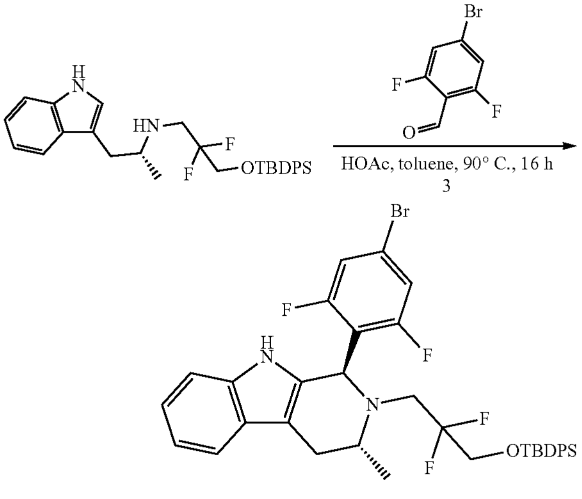

(R)—N-(1-(1H-indol-3-yl)prop-2-yl)-3-((tert-butyldiphenylsilyl)oxy)-2,2-difluoroprop-1-amine (300 mg, 592.07 μmol) and 4-bromo-2,6-difluorobenzaldehyde (143.93 mg, 651.27 μmol) were dissolved in toluene (5 mL), and then acetic acid (355.55 mg, 5.92 mmol, 338.62 uL) was added. The reaction solution was stirred and reacted at 90° C. for 16 hours. The completion of the reaction was monitored by LCMS and TLC (petroleum ether:ethyl acetate=10:1), and the reaction solution was concentrated to dryness under reduced pressure. The reaction concentrate was diluted with ethyl acetate (5 mL) and then washed three times with brine (5 mL), the collected aqueous phase was extracted with ethyl acetate (10 mL) three times, and the organic phase was dried over sodium sulfate, concentrated to dryness under reduced pressure, and then purified by thin layer chromatography (silica, petroleum ether/ethyl acetate=10/1) to obtain (1S, 3R)-1-(4-bromo-2,6-difluorophenyl)-2-(3-((tert-butyldiphenylsilyl)oxy)-2,2-difluoropropyl)-3-methyl-2,3,4,9-tetrahydro-1H-pyridino[3,4-b]indole (350.00 mg).

MS m/z (ESI): 708.9 $[M+H]^+$;

$^1$H NMR (400 MHz, CHLOROFORM-d) δ 7.65-7.59 (m, 4H), 7.52 (br d, J=6.5 Hz, 1H), 7.44-7.37 (m, 6H), 7.25-7.20 (m, 1H), 7.12 (m, J=5.6, 7.2 Hz, 2H), 6.95 (d, J=8.3 Hz, 2H), 5.28 (s, 1H), 4.01-3.88 (m, 1H), 3.69-3.54 (m, 2H), 3.35-3.20 (m, 1H), 2.98 (dd, J=4.6, 14.7 Hz, 1H), 2.83-2.69 (m, 1H), 2.60 (dd, J=3.8, 15.6 Hz, 1H), 1.15 (d, J=6.5 Hz, 3H), 1.04 (s, 9H).

Step 4: Synthesis of (S)—N-(4-((1S,3R)-2-(3-((tert-butyldiphenylsilyl)oxy)-2,2-difluoropropyl)-3-methyl-2,3,4,9-tetrahydro-1H-pyridino[3,4-b]indol-1-yl)-3, 5-difluorophenyl)-1-(3-fluoropropyl) pyrrolidin-3-amine

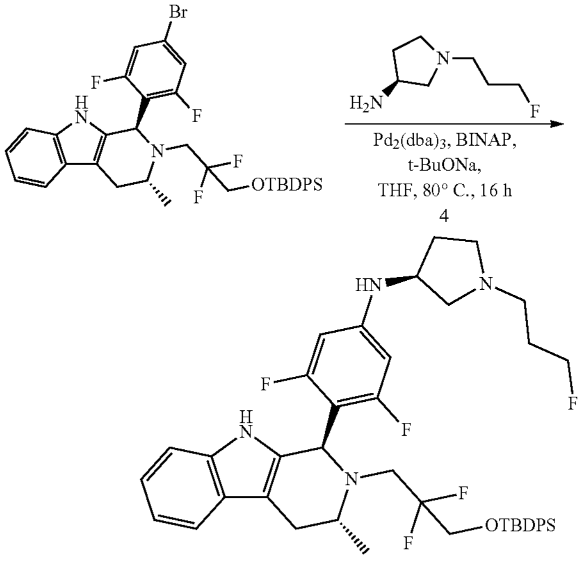

(1S,3R)-1-(4-bromo-2,6-difluorophenyl)-2-(3-((tert-butyldiphenylsilyl)oxy)-2,2-difluoropropyl)-3-methyl-2,3,4,9-tetrahydro-1H-pyridino[3,4-b]indole (300.00 mg, 422.72 μmol) and (S)-1-(3-fluoropropyl)pyrrolidin-3-amine hydrochloride (129 mg, 507.27 μmol) were dissolved in tetrahydrofuran (10 mL), and then sodium tert-butoxide (243.75 mg, 2.54 μmol) and 2,2-dis(diphenylphosphino)-1,1-binaphthyl (131.61 mg, 211.36 μmol) were added, and tris(dibenzylideneacetone)dipalladium (77.42 mg, 84.54 μmol) was added to the reaction system under nitrogen atmosphere. The reaction solution was stirred and reacted at 80° C. for 16 hours. After the completion of the reaction monitored by LCMS, the reaction solution was concentrated to dryness under reduced pressure. The reaction concentrate was diluted with ethyl acetate (10 mL) and then washed with water (10 mL) three times, the collected aqueous phase was extracted with ethyl acetate (20 mL) three times, and the organic phase was dried over sodium sulfate, concentrated to dryness under reduced pressure, and then purified by thin layer chromatography (silica, petroleum ether/tetrahydrofuran=1/1, 1% ammonia water) to obtain (S)—N-(4-((1S,3R)-2-(3-((tert-butyldiphenylsilyl)oxy)-2,2-difluoropropyl)-3-methyl-2,3,4,9-tetrahydro-1H-pyridino[3,4-b]indol-1-yl)-3,5-difluorophenyl)-1-(3-fluoropropyl)pyrrolidin-3-amine (54.00 mg).

MS m/z (ESI): 400.5 $[M+H]^+$

Step 5: Synthesis of 3-((1S,3R)-1-(2,6-difluoro-4-(((S)-1-(3-fluoropropyl)pyrrolidin-3-yl)amino)phenyl)-3-methyl-3,4-dihydro-1H-pyridino[3,4-b]indole-2(9H)-yl)-2,2-difluoropropane-1-ol

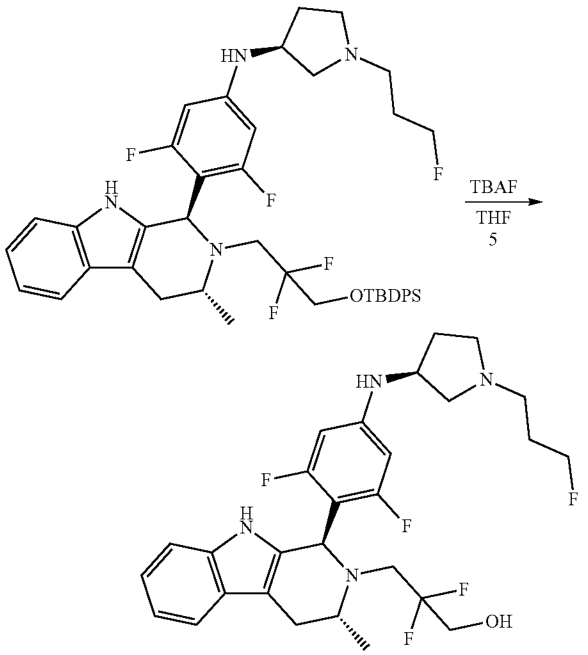

(S)—N-(4-((1S,3R)-2-(3-((tert-butyldiphenylsilyl)oxy)-2,2-difluoropropyl)-3-methyl-2,3,4,9-tetrahydro-1H-pyridino[3,4-b]indol-1-yl)-3, 5-difluorophenyl)-1-(3-fluoropropyl)pyrrolidin-3-amine (50.00 mg, 64.52 μmol) was dissolved in tetrahydrofuran (2 mL), and tetrabutylammonium fluoride tetrahydrofuran solution (1 mol/L, 129.04 uL) was added. The reaction solution was stirred and reacted at 25° C. for 5 hours. The completion of the reaction was monitored by TLC (silica, dichloromethane:methanol=10:1), and then 5 mL of water was added to the reaction solution, and the solution was stirred at room temperature for 10 minutes. The organic phase was washed with brine (5 mL) three times, the collected aqueous phase was extracted with ethyl acetate (10 mL) three times, and the organic phase was dried over sodium sulfate, concentrated to dryness under reduced pressure, and then purified by thin layer chromatography (silica, dichloromethane:methanol=10:1) to obtain the compound 3-((1S,3R)-1-(2,6-difluoro-4-(((S)-1-(3-fluoropropyl)pyrrolidin-3-yl)amino)phenyl)-3-methyl-3,4-dihydro-1H-pyridino [3,4-b]indole-2(9H)-yl)-2,2-difluoropropane-1-ol (32.00 mg).

MS m/z (ESI): 559.1 $[M+Na]^+$ $^1$H NMR (400 MHz, METHANOL-$d_4$) δ 7.38 (d, J=7.3 Hz, 1H), 7.18 (d, J=7.5 Hz, 1H), 7.02-6.91 (m, 2H), 6.14 (d, J=11.8 Hz, 2H), 5.15 (s, 1H), 4.53 (t, J=5.8 Hz, 1H), 4.42 (t, J=5.6 Hz, 1H), 3.99-3.91 (m, 1H), 3.86-3.72 (m, 1H), 3.66-3.57 (m, 1H), 3.52-3.39 (m, 1H), 3.20-3.08 (m, 1H), 3.00-2.91 (m, 2H), 2.84-2.73 (m, 2H), 2.70-2.51 (m, 5H), 2.37-2.26 (m, 1H), 1.98-1.83 (m, 2H), 1.76-1.65 (m, 1H), 1.14 (d, J=6.5 Hz, 3H).

Test of Biological Activity and Related Properties

Test Example 1: Detection of the Degradation Effect of the Compounds of the Present Invention on Estrogen Receptors in MCF7 Cells

1. Experiment Purpose

The purpose of the experiment is to determine the degradation activity of the compounds of the present invention on endogenously expressed estrogen receptors in MCF7 cells, and to evaluate the activity of the compounds according to $DC_{50}$ and maximum degradation efficiency.

2. Experimental Method

MCF7 cells (ATCC, HTB-22) were cultured in DMEM (Gibco, 11995-065) complete medium containing 10% fetal bovine serum. On the first day of the experiment, MCF7 cells were inoculated in a 384-well plate at a density of 3000 cells/well using the complete medium, and cultured in a 37° C., 5% $CO_2$ cell incubator. The compounds to be tested were dissolved in DMSO with a stock concentration of 10 mM, the solution was diluted with Echo 550 (Labcyte Inc.) and added to the cell culture plate. Each compound with the starting concentration for treatment of 100 nM was subjected to 3-fold gradient dilution with 9 concentration points. A blank control containing 0.5% DMSO was set, and double replicate wells as controls were set at each concentration point. The culture was cultured in a 37° C., 5% $CO_2$ cell incubator for 24 hours. Paraformaldehyde was added to the cell culture medium in each cell culture well, and the final concentration of paraformaldehyde was about 3.7% to fix the cells. After the mixture was reacted for 30 minutes, the supernatant was discarded, and 50 μL of PBS was added to each well for washing once. The cells were treated with PBS containing 0.5% v/v Tween-20 for 30 minutes, and washed with PBS once. A blocking solution (PBS containing 5% BSA, 0.05% Tween-20) was added, and the mixture was incubated at room temperature for 1 hour. The blocking solution was removed, a mixture solution of primary antibodies (anti-ER mAb, Estrogen Receptor α (D8H8) Rabbit mAb, GST, #8644S, 1:1000 dilution; anti-GAPDH mAb, GAPDH($D4C_6R$) Mouse mAb, GST, #97166S, 1:2000 dilution) was added, and the mixture was incubated at room temperature for 3 hours. The culture was washed with PBST (PBS containing 0.05% Tween-20) 3 times. Secondary antibodies for detection (800CW-goat anti-rabbit IgG, LI-COR, P/N: 926-32211, 1:1000 dilution; 680RD-goat anti-mouse IgG, LI-COR, #925-68070, 1:1000 dilution) were added, and the mixture was incubated at room temperature and in the dark for 45 minutes. After washing with PBST 3 times, the fluorescence signal of each well was read using Odyssey CLx, and the value of Chanel 800 (ER)/Chanel 680 (GAPDH) was calculated. The wells treated with 0.1 μM fulvestrant were used as the 100% degradation control, and the degradation rate at each concentration point was calculated. The data were analyzed and processed by XlLfit, and the degradation activity $DC_{50}$ and the maximum degradation rate Imax of each compound were calculated. See Table 1 for data analysis

TABLE 1

Degradation activity of the compounds of the present invention against estrogen receptors in MCF7 cells

| Compound number | ER level $DC_{50}$ (nM) | Maximum degradation rate |
|---|---|---|
| Example 1 | 0.41 | 106% |
| Example 2 | 8.5 | 92% |
| Example 3 | 0.15 | 104% |
| Example 4 | 0.04 | 99% |
| Example 5 | 0.58 | 80% |
| Example 6 | 0.50 | 90% |
| Example 7 | 0.06 | 99% |

Test Example 2: Detection of the Inhibitory Effect of the Compounds of the Present Invention on the Proliferation of MCF7 Cells

1. Experiment Purpose

The purpose of the experiment is to determine the inhibitory effect of the compounds of the present invention on the proliferation of MCF7 cells in vitro, and to evaluate the activity of the compounds according to and maximum inhibitory efficiency.

2. Experimental Method

MCF7 cells (ATCC, HTB-22) were cultured in DMEM (Gibco, 11995-065) complete medium containing 10% fetal bovine serum. On the first day of the experiment, MCF7 cells were inoculated in a 384-well plate at a density of 500 cells/well using the complete medium, and cultured in a 37° C., 5% $CO_2$ cell incubator overnight. The next day, the compounds to be tested were added for drug treatment, and the compound solution with a stock concentration of 10 mM was diluted with Echo550 (Labcyte Inc.) and transferred to each cell culture well. Each compound with the starting concentration for treatment of 100 nM in cells was subjected to 3-fold gradient dilution with 9 concentration points. A blank control containing 0.3% DMSO was set, and double replicate wells as controls were set at each concentration point. The culture was cultured in a 37° C., 5% $CO_2$ cell incubator for 7 days, and the cell culture plate was taken out on day 8. CellTiter-Glo® Luminescent Cell Viability Assay (Promega, G7573) was added, and after standing at room temperature for 10 minutes, the luminescence signal value was read using a multi-label microplate reader EnVision (PerkinElmer), and the inhibitory activity $IC_{50}$ of each compound was calculated according to the compound concentration and luminescence signal value using XLfit.

3. See Table 2 for Data Analysis

TABLE 2

Inhibitory activity of the compounds of the present invention to the proliferation of MCF7 cells

| Compound number | MCF-7 cell proliferation inhibition $IC_{50}$ (nM) |
|---|---|
| Example 1 | 0.58 |
| Example 2 | 15 |
| Example 3 | 0.27 |
| Example 4 | 0.23 |

TABLE 2-continued

| Inhibitory activity of the compounds of the present invention to the proliferation of MCF7 cells | |
|---|---|
| Compound number | MCF-7 cell proliferation inhibition $IC_{50}$ (nM) |
| Example 5 | 2.57 |
| Example 6 | 2.39 |
| Example 7 | 0.12 |

Test Example 3: Inhibitory Effect of the Compounds of the Present Invention on CYP2C9 and CYP2D6 Enzymatic Activities The inhibition of CYP2C9 and CYP2D6 enzymatic activities by the compounds of the present invention was determined by the following test method.

I. Test Materials and Instruments

1. Human liver microsomes (Corning 452117)
2. NADPH (Solarbio 705Y021)
3. Positive substrates diclofenac (Sigma SLBV3438), dextromethorphan (TRC 3-EDO-175-1) and midazolam (Cerilliant FE0161704)
4. Positive inhibitors sulfaphenazole (D. Ehrenstorfer GmbH 109012), quinidine (TCI WEODL-RE) and ketoconazole (Sigma 100M1091V)
5. AB Sciex Triple Quad 5500 liquid chromatography-mass spectrometry

II. Test Steps

1. Preparation of 100 mM phosphate buffered saline (PBS): 7.098 g of $Na_2HPO_4$ was weighed, 500 mL of pure water was added and subjected to ultrasonic dissolution to obtain solution A. 3.400 g of $KH_2PO_4$ was weighed, 250 mL of pure water was added and subjected to ultrasonic dissolution to obtain solution B. Solution A was placed on a stirrer and solution B was slowly added until pH reaches 7.4 to prepare 100 mM PBS buffer.
2. Preparation of 10 mM NADPH solution with 100 mM PBS buffer. 10 mM stock solution of compounds of the invention was diluted with DMSO to obtain a 200× concentration of compound working solution (6000, 2000, 600, 200, 60, 20, 0 μM). The stock solution of positive inhibitors was diluted with DMSO to obtain a 200× concentration of positive inhibitor working solution (sulfaphenazole, 1000, 300, 100, 30, 10, 3, 0 μM; quinidine/ketoconazole, 100, 30, 10, 3, 1, 0.3, 0 μM). A 200× concentration of substrate working solution (120 μM of diclofenac, 400 μM of dextromethorphan, and 200 μM of midazolam) was prepared in water, acetonitrile, or acetonitrile/methanol.
3. 2 μl of 20 mg/ml liver microsome solution, 1 μl of substrate working solution, 1 μl of compound working solution and 176 μl of PBS buffer were taken, mixed uniformly, and pre-incubated in a 37° C. water bath for 15 minutes. To the positive control group was added 1 μl of diclofenac, dextromethorphan or midazolam working solution to replace the compound working solution. Simultaneously, 10 mM of NADPH solution was pre-incubated together in a 37° C. water bath for 15 minutes. After 15 minutes, 20 μl of NADPH was added to each well to initiate the reaction, and the reaction was incubated at 37° C. for 5 minutes (CYP2C9) or 20 minutes (CYP2D6). Double samples were set for all incubation samples. After incubation for corresponding time, the reaction was terminated by adding 400 ul of ice methanol containing an internal standard to all samples. The mixture was mixed uniformly by vortex and centrifuged at 3220 g at 4° C. for 40 minutes. After centrifugation, 100 μL of the supernatant was transferred to a loading plate, and 100 μL of ultrapure water was added and mixed uniformly for LC-MS/MS analysis.

The $IC_{50}$ values of the compounds of the present invention against CYP2C9 and CYP2D6 were calculated by Excel XLfit 5.3.1.3.

TABLE 3

| $IC_{50}$ values of the compounds of the present invention against CYP2C9 and CYP2D6 | | |
|---|---|---|
| Example number | CYP2C9 (μM) | CYP2D6 (μM) |
| Example 3 | >30 | >30 |
| Example 4 | 20 | 27 |
| Example 7 | 8 | 23 |

Test Example 4: Determination of Plasma Protein Binding Rate of the Compounds of the Present Invention Human plasma protein binding is a key factor in controlling the amount of free (unbound) drug available for binding to the target and plays an important role in the observed in vivo efficacy of the drug. Therefore, among compounds with similar potency and exposure levels, the compounds with high free fractions (low levels of plasma protein binding) may exhibit enhanced efficacy.

The protein binding rate of the compounds of the present invention in the plasma of five species (human, monkey, dog, rat and mouse) was determined by the following test method.

I. Test Materials and Instruments

1. Human plasma (BioIVT), beagle dog plasma (BioIVT), SD rat plasma (BioIVT), CD-1 mouse plasma (BioIVT);
2. 96-well equilibrium dialysis plate (HTDialysis LLC, Gales Ferry, CT, HTD96B), equilibrium dialysis membrane (MWCO 12-14K, #1101);
3. Positive control compound warfarin;
4. ABI QTrap 5500 liquid chromatography-mass spectrometry.

II. Test Steps

1. Preparation of a buffer with a concentration of 100 mM sodium phosphate and 150 mM NaCl: an alkaline solution with a concentration of 14.2 g/L $Na_2HPO_4$ and 8.77 g/L NaCl was prepared with ultrapure water, and an acidic solution with a concentration of 12.0 g/L $NaH_2PO_4$ and 8.77 g/L NaCl was prepared with ultrapure water. The alkaline solution was titrated with the acidic solution to pH 7.4 to prepare a buffer with a concentration of 100 mM sodium phosphate and 150 mM NaCl.

2. Preparation of dialysis membrane: the dialysis membrane was soaked in ultrapure water for 60 minutes to separate the membrane into two pieces, then soaked in 20% ethanol for 20 minutes, and finally soaked in the buffer used for dialysis for 20 minutes.
3. Preparation of plasma: the frozen plasma was quickly thawed at room temperature, then the plasma was centrifuged at 3,220 g at 4° C. for 10 min to remove clots, and the supernatant was collected into a new centrifuge tube. The pH of the plasma was measured and recorded, and the plasma with pH of 7-8 was used.
3. Preparation of compound-containing plasma samples: 10 mM stock solution of compounds of the present invention or positive control compounds were diluted with DMSO to obtain 200 μM working solution. To 597 μl of human, monkey, dog, rat, or mouse plasma was added 3 μl of 200 μM compound working solution to obtain a plasma sample with a final concentration of 1 μM.
4. Equilibrium dialysis steps: the dialysis devices were assembled according to the operating instructions. 120 μL of plasma sample containing 1 μM compound was added to one side of the dialysis membrane, and an equal volume of dialysate (phosphate buffer) was added to the other side thereof. Double samples were set for the experiment. The dialysis plate was sealed, put into the incubation device, and incubated at 37° C., 5% $CO_2$ and about 100 rpm for 6 hours. After the completion of the incubation, the sealing film was removed and 50 μl was pipetted from the buffer and plasma sides in each well, respectively, into separate wells of a new plate. 50 μl of blank plasma was added to the phosphate buffer sample, an equal volume of blank phosphate buffer was added to the plasma sample, and then 300 μl of acetonitrile containing the internal standard was added to precipitate the protein. The mixture was vortexed for 5 minutes and centrifuged at 3,220 g at 4° C. for 30 minutes. 100 μL of the supernatant was taken into a loading plate, and 100 μL of ultrapure water was added and mixed uniformly for LC-MS/MS analysis.

The peak areas of the compounds on the buffer side and the plasma side were determined. The formula for calculating the plasma protein binding rate of the compound is as follows:

$$\text{free rate } \% = (\text{ratio of compound peak area to internal standard peak area}_{buffer\ side}/\text{ratio of compound peak area to internal standard peak area}_{plasma\ side}) \times 100$$

$$\text{Binding rate } \% = 100 - \text{free rate } \%$$

All the data was calculated by the Microsoft Excel software. The plasma protein binding rate values of the compounds of the present invention were calculated.

TABLE 4

Protein binding rate values of the compounds of the present invention in human, dog, rat and mouse plasma

| Example number | Species | Protein binding rate (%) |
|---|---|---|
| Example 3 | Human | 98.8 |
| | Cynomolgus monkey | 97.8 |
| | Beagle dog | 98.7 |
| | SD rat | 97.1 |
| | CD-1 mouse | 98.1 |

TABLE 4-continued

Protein binding rate values of the compounds of the present invention in human, dog, rat and mouse plasma

| Example number | Species | Protein binding rate (%) |
|---|---|---|
| Example 4 | Human | 99.8 |
| | Cynomolgus monkey | 99.8 |
| | Beagle dog | 99.8 |
| | SD rat | 99.8 |
| | CD-1 mouse | 99.8 |
| Example 7 | Human | 99.5 |
| | Cynomolgus monkey | 97.7 |
| | Beagle dog | 98.8 |
| | SD rat | 98.5 |
| | CD-1 mouse | 98.8 |

Test Example 5: Apparent Solubility of the Compounds of the Present Invention in Phosphate Buffer at DH 7.4

For the purpose that orally administered compounds can reach the site of action, and can be effectively absorbed by the gut, the compounds are expected to be in solution form, and therefore, the compounds with a high intrinsic solubility may be more suitable for pharmaceutical use.

I. Materials and Reagents

The compounds to be tested were prepared according to the method described. The control drug progesterone was purchased from Sigma. Phosphate buffer with pH 7.4 was prepared in our laboratory. Acetonitrile and methanol were purchased from Fisher. Other reagents were purchased from the market.

1.5 ml flat bottom glass vial (BioTech Solutions); polytetrafluoroethylene/silicone stoppers (BioTech Solutions); polytetrafluoroethylene-coated stirring rod; MultiScreenHTS HV (0.45 μm) 96 well plate filter plate (Millipore, MSHVN4510 or MSHVN4550); Eppendorf Thermomixer Comfort; Vacuum Manifold ORVMN96 (Orochem).

II. Experimental Steps

1) Preparation of Stock Solution 10 mM stock solution of substance to be tested and control drug progesterone was prepared with DMSO.

2) Steps of Apparent Solubility Determination

30 μL of 10 mM stock solution of substance to be tested was taken, and added to the corresponding position of the corresponding 96-well plate in the specified order. 970 μL of phosphate buffer (pH 7.4) was added to the corresponding vial in the sample plate. The experiment was performed in parallel duplicate. A stirring rod was added to each vial and a polytetrafluoroethylene/silicone stopper was covered thereon. The sample tray was then placed in an Eppendorf Thermomixer Comfort and shaken at 1100 rpm for 2 hours at 25° C. After 2 hours, the stopper was removed, and the stirring rod was sucked away by a large magnet, then the sample was transferred from the sample plate to the filter plate. A vacuum pump was used to generate negative pressure and the sample was filtered. 5 μL of the filtrate was transferred to a new sample plate, and then 5 μL of DMSO and 490 μL of 50% ACN(IS)·$H_2O$ (internal standard acetonitrile:water=1:1) were added. Depending on the peak shape, it may be possible to dilute the sample diluent with a certain proportion of 50% ACN(IS)·$H_2O$ for better peak shape. The dilution fold may be adjusted according to the solubility of the substance to be tested or the signal strength of its response to liquid chromatography-mass spectrometry.

3) Steps of Sample Analysis

The loading plate was placed in the loading tray of the autosampler, and the sample was evaluated by liquid chromatography-mass spectrometry analysis.

III. Experimental Steps

All calculations are performed via Microsoft Excel. Analysis and quantification of the sample filtrate was accomplished by using the liquid chromatography-mass spectrometry to characterize and quantify the peaks of the standards with known concentrations. The apparent solubility of the compounds of the present invention in phosphate buffer (PH 7.4) was calculated.

TABLE 5

Apparent solubility values of the compounds of the present invention in phosphate buffer (pH 7.4)

| Example number | Apparent Solubility (μM) at pH = 7.4 |
|---|---|
| Example 3 | 92 |
| Example 4 | <0.3 |
| Example 7 | 4 |

Test Example 6: Whether the Compounds of the Present Invention has Potential Inhibitory Effect on the Voltage-Gated Potassium Ion Channel hERG The hERG potassium channel is crucial for normal electrical activity in the heart. Arrhythmias can be induced by blocking hERG channels with a variety of drugs. Such side effect is a common cause of drug failure in preclinical safety trials, and therefore, minimization of hERG channel blocking activity may be a desirable property for drug candidates.

I. Materials and Reagents

1. Experimental Materials and Instruments

| Experimental materials | Supplier (Cat. No.) |
|---|---|
| 6/3.5 cm cell culture dish | Shanghai Yes Service Biotechnology Co., Ltd. (150288/153066) |
| Dialysis fetal bovine serum | Shanghai BioSun Sci&Tech Co., Ltd. (BS-0005-500) |
| DMEM medium | Thermo Fisher Scientific (China) Co., Ltd. (10569) |
| HEPES | Thermo Fisher Scientific (China) Co., Ltd. (15630080) |
| Trypsin | Thermo Fisher Scientific (China) Co., Ltd. (2192509) |
| Penicillin-streptomycin solution | Thermo Fisher Scientific (China) Co., Ltd. (15140-122) |
| MEM non-essential amino acid solution | Thermo Fisher Scientific (China) Co., Ltd. (11140) |
| Geneticin (G418) (11811031) | Thermo Fisher Scientific (China) Co., Ltd. |
| Blasticidin | Thermo Fisher Scientific (China) Co., Ltd. (R21001) |
| Polylysine | Thermo Fisher Scientific (China) Co., Ltd. (P4832) |
| Dofetilide | Beijing Express Technology Co., Ltd. (D525700) |

-continued

| Experimental materials | Supplier (Cat. No.) |
|---|---|
| Doxycycline | Sigma-Aldrich (Shanghai) Trading Co., Ltd. (D9891) |
| Carbon dioxide incubator | Thermo Fisher Scientific (China) Co., Ltd. (371) |
| Puller | American Sutter Company (P-97) |
| Micromanipulator | American Siskiyou Company (MC1000e) |
| Micromanipulator | American Sutter Company (ROE-200; MP285) |
| Amplifier | Germany HEKA company (EPC10) |
| Microscope | Olympus (China) Co., Ltd. (IX51/71/73) |
| Perfusion system | American ALA company (VM8 gravity drug delivery system) |

2. Cell Lines and Culture

HEK293 cell line stably expressing hERG ion channel (Cat. No. K1236) was purchased from Invitrogen. The cell line was cultured in the medium containing 85% DMEM, 10% dialysis fetal bovine serum, 0.1 mM non-essential amino acid solution, 100 U/mL penicillin-streptomycin solution, 25 mM HEPES, 5 g/mL blasticidin and 400 g/mL geneticin. When the cell density increased to 40%-80% of the bottom area of the culture dish, trypsin was used for digestion and passage, and the cells were passaged three times weekly. Before the experiment, the cells were cultured in a 6 cm culture dish at a density of $5\times10^5$ and induced by adding 1 g/mL doxycycline for 48 hours, and then the cells were digested and inoculated on glass slides for subsequent manual patch clamp experiments.

3. Preparation of Compounds to be Tested

1) According to the SOP-ADMET-MAN-007 standard operating procedure, the compounds to be tested were dissolved with DMSO and prepared into the stock solution with a final concentration of 10 mM.
2) The stock solution was subjected to gradient dilution with DMSO at a ratio of 1:3 into solutions with three other intermediate concentrations of 3.33 mM, 1.11 mM, and 0.37 mM, respectively.
3) Before the start of the experiment, the stock solution of the compounds to be tested and the intermediate solutions were diluted 1000 times with extracellular fluid to obtain working solutions with a series of concentrations of 10 μM, 3.33 μM, 1.11 μM and 0.37 μM; in addition, 10 mM of the stock solution was diluted 333.33 times with extracellular fluid to obtain a working solution with a concentration of 30 μM. The content of DMSO in the working solution is 0.1-0.3% (volume ratio).

(Notes: the content of DMSO in the working solution should be controlled within 1% (volume ratio) to avoid cytotoxicity.)

4) After the completion of the preparation of the working solution, visual observation was performed to check whether there were precipitates or turbid substances in the working solution. If there were precipitates or turbid substances, it was probably due to poor solubility of the compound in physiological solutions, and then same can be further subjected to ultrasonic treatment in a water bath for 30 minutes to improve the clarity of the solution.
5) The potential inhibitory effects of the test substances at 5 concentrations of 30 μM, M, 3.33 μM, 1.11 μM and 0.37 μM on hERG channel were determined, and the dose-effect curve was fitted and $IC_{50}$ was calculated.

II. Experimental Method

1. The small glass slide loaded with HEK293 cells in the culture dish was placed in the perfusion tank of the micromanipulator.
2. The appropriate amounts of cells were adjusted and placed in the center of the field of view under an Olympus IX51, IX71 or IX73 inverted microscope, and the tip of the glass electrode was found by using a ×10× objective and placed in the center of the field of view. Then, the electrode was moved down by using the micromanipulator, meanwhile, the coarse focusing adjustment knob was adjusted so as to allow the electrode to slowly approach the cells.
3. When approaching the cell, a ×40× objective was used for observation, and the micromanipulator is used for fine adjustment so as to allow the electrode to gradually approach the surface of the cells.
4. A negative pressure was applied to form a giga-seal with a resistance higher than 1 GΩ between the electrode tip and the cell membrane.
5. The instantaneous capacitive current Cfast was compensated in voltage-clamp mode. Then short negative pressure was applied repeatedly to rupture the membrane, thereby finally forming a whole-cell recording mode.
6. Under the membrane potential clamped at −60 mV, the slow capacitive current Cslow, cell membrane capacitance (Cm) and input membrane resistance (Ra) were compensated, respectively.
7. After the cells were stabilized, the clamping voltage was changed to −90 mV, the sampling frequency was set to 20 kHz, and the filtering frequency was set to 10 kHz. The detection condition of leakage current was that the clamping voltage was changed to −80 mV, and the time course was 500 ms.
8. The method for measuring hERG current is as follows: the membrane potential was depolarized from −80 mV to +30 mV by applying a depolarizing command voltage for 4.8 s, followed by an instantaneous application of a repolarizing voltage for 5.2 s to make the membrane potential down to −50 mV to remove channel inactivation, so that hERG tail current was observed. The peak value of the tail current is the magnitude of the hERG current.
9. The hERG currents used to detect the compounds to be tested were continuously recorded for 120 seconds before administration to evaluate the stability of the hERG currents produced by the test cells. Only stable cells within the acceptable range of the evaluation criteria can be used for subsequent compound testing.
10. Determination of the inhibitory effect of the compounds to be tested on hERG current: First, the hERG current measured in extracellular fluid containing 0.1% DMSO was used as the detection baseline. After the hERG current remained stable for at least 5 minutes, the solution containing the compound to be tested was perfused around the cells from low to high concentration. By waiting for about 5 minutes after the completion of each perfusion, the compound was allowed to fully act on the cells, and the hERG currents were simultaneously recorded. After the currents to be recorded became stable, the last 5 hERG current values were recorded, and the average value thereof was taken as the final current value thereof at a specific concentration. After the completion of the compound testing, 150 nM of dofetilide was added to the same cell to completely inhibit its current, which was used as a positive control for that cell. In addition, the positive compound dofelide was detected with the same patch clamp system both before and after the completion of the test compound experiment to ensure the reliability and sensitivity of the entire detection system.

III. Data Analysis

Data was exported by PatchMaster software and analyzed according to the following steps:

1) After perfusion of blank solvent or compound gradient solution, the average value of 5 continuous current values obtained in a stable state is calculated as "tail current $value_{blank}$" and "tail current $value_{compound}$", respectively.
2) The percent current inhibition was calculated by the following formula.

$$\text{Tail current inhibition rate} = \left\{1 - \frac{\text{Tail current value}_{Compound} - \text{Tail current value}_{Positive\ drug}}{\text{Tail current value}_{Blank} - \text{Tail current value}_{Positive\ drug}}\right\} \times 100$$

3) The dose-effect curve was fitted by Graphpad Prism 8.0 software, and $IC_{50}$ value was calculated.

The inhibition of hERG by the compounds of the present invention is as shown in Table 6 below

TABLE 6

Inhibitory activity of the compounds of the present invention against voltage-gated potassium ion channel hERG

| Example number | hERG $IC_{50}$ (μM) |
|---|---|
| Example 3 | 10 |
| Example 4 | 3.7 |
| Example 7 | 8.4 |

Test Example 7: Pharmacokinetic Evaluation of the Compounds of the Present Invention in Mice Experimental Materials CD-1 mice were purchased from Beijing Vital River Laboratory Animal Technology Co., Ltd. DMSO (dimethyl sulfoxide), HP-β-CD (hydroxypropyl-β-cyclodextrin), Tetraethylene Glycol, Captisol (SBE-β-CD, sulfobutyl-β-cyclodextrin) were purchased from Sigma. Acetonitrile was purchased from Merck (USA).

Experimental Method

Six female CD-1 mice (20-30 g, 4-6 weeks) were randomized into 2 groups, 3 mice/group. Group 1 was given the test compound via tail vein injection at a dose of 1 mg/kg, and the vehicle was 5% DMSO in 10% HP-β-CD in water, and group 2 was given the test compound orally at a dose of 10 mg/kg, and the vehicle was 40% Tetraethylene Glycol (v/v), 7.5% Captisol (w/v) in water. Prior to the experiment, the animals were given food and water as usual. Before administration and 0.083 (only for the vein injection group), 0.25, 0.5, 1, 2, 4, 6, 8 and 24 h after administration, blood was sampled from the veins of the mice in each group. The whole blood sample collected was placed in a K2EDTA anticoagulation tube and centrifuged for 5 min (12,000 rpm, 4° C.) and then the plasma was taken for later detection.

10 μL of the mouse plasma sample was taken and 150 μL of acetonitrile solvent (wherein internal standard compound was contained) was added to precipitate proteins. After the mixture was vortexed for 5 min, centrifugation (14,000 rpm) was performed for 5 min. The supernatant was diluted 2-fold with water containing 0.1% (v/v) FA and injected into the LC-MS/MS system (AB Sciex Triple Quad 6500+) for the quantitative detection. A calibration standard curve was prepared in CD-1 mouse plasma along with quality control samples to determine the plasma concentration. For the 10× diluted samples, 2 μL of the sample was taken and 18 μL of blank plasma was added. After the mixture was vortexed for 0.5 min, 300 μL of acetonitrile solvent (wherein an internal standard compound was contained) was added to precipitate proteins. The other processing steps were identical to those for the samples not diluted.

The PK test results are as shown below, the compounds of the present invention show good PK properties and oral bioavailability in mice:

ment, and feeding was resumed four hours after administration. Plasma and brain tissue were collected from rats of each group 2 h after administration. The whole blood sample collected was placed in a $K_2$EDTA anticoagulation tube and centrifuged for 5 min (12,000 rpm, 4° C.) and then the plasma was taken for later detection. After tissue collection, the tissue was dried with filter paper, and the samples were stored in a −80° C. freezer for later detection.

10 μL of the rat plasma sample was taken and 150 μL of acetonitrile solvent (wherein an internal standard compound was contained) was added to precipitate proteins. After the mixture was vortexed for 5 min, centrifugation (14,000 rpm) was performed for 5 min. The supernatant was diluted 2-fold with water containing 0.1% (v/v) FA and injected into the LC-MS/MS system (AB Sciex Triple Quad 6500+) for the quantitative detection. For the 10× diluted samples, 2 μL of the sample was taken and 18 μL of blank plasma was added. After the mixture was vortexed for 0.5 min, 300 μL of acetonitrile solvent (wherein an internal standard compound was contained) was added to precipitate proteins. The other processing steps were identical to those for the samples not diluted. A calibration standard curve was prepared in SD rat plasma along with plasma quality control samples to determine the plasma concentration.

TABLE 7

PK of the compounds of the present invention in mice

| Compound number | Administration/ dose mg/kg | Maximum drug concentration ng/ml | Time to peak drug concentration h | Time of half drug elimination h | Drug exposure ng * h/ml | Oral bioavailability (%) |
|---|---|---|---|---|---|---|
| Example 3 | IV-1 mpk | 98 | — | 13 | 414 | 68% |
| | PO-10 mpk | 219 | 3 | 9 | 2804 | |
| Example 4 | IV-1 mpk | 78 | — | 21 | 639 | 60% |
| | PO-10 mpk | 222 | 5 | 19 | 3853 | |
| Example 7 | IV-1 mpk | 259 | — | 5 | 879 | 62% |
| | PO-10 mpk | 555 | 1 | 4 | 5447 | |

Test Example 8: Blood-Brain Barrier (BBB) Permeability of the Compounds of the Present Invention in Rats Adequate exposure of drugs to the brain by means of permeating through the blood-brain barrier in animals is the key to achieving the effectiveness of drugs against brain metastatic lesion. Therefore, the distribution of drugs in the brain can be assessed by measuring the drug concentrations in plasma and brain tissue of animals after administration, so as to determine whether the drug can inhibit tumor growth in the intracranial model.

Experimental Materials

Female SD rats were purchased from Beijing Vital River Laboratory Animal Technology Co., Ltd. MC (methyl cellulose) was purchased from Sigma; Acetonitrile was purchased from Merck (USA). PBS (phosphate buffered saline) was purchased from Sangon Biotech Co., Ltd.

Experimental Method

Six female SD rats (200-300 g, 6-8 weeks) were randomized into 2 groups, 3 rats/group. Each rat was given the compounds of the present invention, and the vehicle was 0.5% methylcellulose aqueous solution. Animals were fed with water as usual and fasted overnight before the experi- Brain tissue samples from rat were first homogenized with 4 times the mass volume of PBS homogenate. 20 μL of brain tissue homogenate sample was taken, and 20 μL of blank mouse plasma was added. The mixture was diluted and mixed uniformly, and 600 μL of acetonitrile solvent (wherein an internal standard compound was contained) was added to precipitate proteins. After the mixture was vortexed for 5 min, centrifugation (14,000 rpm) was performed for 5 min. The supernatant was diluted 2-fold with water containing 0.1% (v/v) FA and injected into the LC-MS/MS system (AB Sciex Triple Quad 6500+) for the quantitative detection. The compound #Example 3 of the present invention shows an excellent blood-brain barrier permeability, and has a high drug exposure in the brain tissue of rats.

The results of BBB test are as shown below:

TABLE 8

Blood-brain barrier penetration experiment of compounds of present invention in rats

| Compound number | Dosage of administration mg/kg | Drug concentration in plasma ng/ml | Drug concentration in brain ng/g | B/P ratio |
|---|---|---|---|---|
| Example 3 | 100 QD | 2617 | 10560 | 4.2 |
| Example 7 | 100 QD | 2543 | 703 | 0.28 |

Test Example 9: Growth Inhibitory Experiment of the Compounds of the Present Invention in MCF-7 Subcutaneous Tumor Model in Mice

Experimental Reagents

Human breast cancer MCF-7 cells: ATCC, HTB-22
17β-estradiol tablets: Innovative Research of America, Cat No.: SE-121, 60-day release, 0.72 mg/pellet
EMEM medium: ATCC, Cat No.: 30-2003
Fetal bovine serum: Gbico; Cat No.: 1099-141C
Penicillin (Pen Strep): Gibco, Cat No.: 15240-122
Recombinant human insulin: Shanghai Yeasen Biotechnology Co., Ltd., Cat. No.: 40112ES60
0.25% trypsin-EDTA: Gibco, Cat No.: 25200-072
D-PBS (phosphate buffered saline free of Ca and Mg ions): Hyclone, Cat. No.: SH30256.01
Matrigel: Corning, Cat. No.: 356237

Experimental Method

Animal information: NPG mice (female, 6-7 weeks, body weight: about 19-28 g) were purchased from Beijing Vitalstar Biotechnology Co., Ltd. The mice were fed in SPF environment and each cage position was individually ventilated. All animals had free access to standard certified commercial laboratory food and water.

Cell culture: The human breast cancer MCF-7 cell line was cultured in vitro in EMEM (cell culture medium) supplemented with 10% fetal bovine serum, 1% Pen Strep and 10 g/ml recombinant human insulin in a 37° C., 5% $CO_2$ incubator. Conventional digestion treatment with 0.25% trypsin-EDTA digestion solution was carried out once weekly for passage. When the cell saturation was 80%-90%, and the number reached the requirement, the cells were collected and counted.

Cell inoculation: 0.1 ml/(containing $1\times10^7$) MCF-7 cell suspension (volume ratio of D-PBS:Matrigel=1:1) was inoculated subcutaneously on the right back of each mouse, and the mice were inoculated subcutaneously with 170-estradiol tablets four days before the cell inoculation. On day 24 after cell inoculation, the mice were randomized into groups for administration according to the tumor volume, and the day of grouping was Day 0.

Administration: The compound #Example 1 was administered at a dose of 1, 3, or 10 mg/kg, orally (PO), once daily (QD) for 3 weeks. The compound #Example 2 was administered at a dose of 10 mg/kg, orally (PO), once daily (QD) for 3 weeks. 8 mice were in the vehicle group and 6 mice were in the administration group.

Tumor Measurement and Experimental Index:

The diameter of the tumor was measured with vernier calipers twice weekly. The calculation formula of tumor volume was $V=0.5a\times b^2$, wherein a and b represented the long and short diameters of the tumor, respectively. The body weights of the mice were weighed twice weekly.

The tumor-inhibiting efficacy of the compound was evaluated using tumor growth inhibition (TGI) (%). TGI (%)=[(1−(average tumor volume at the end of administration in a certain treatment group−average tumor volume at the beginning of administration in the treatment group)/(average tumor volume at the end of administration in the solvent control group−average tumor volume at the beginning of administration in the solvent control group)]×100%.

Figure 2:
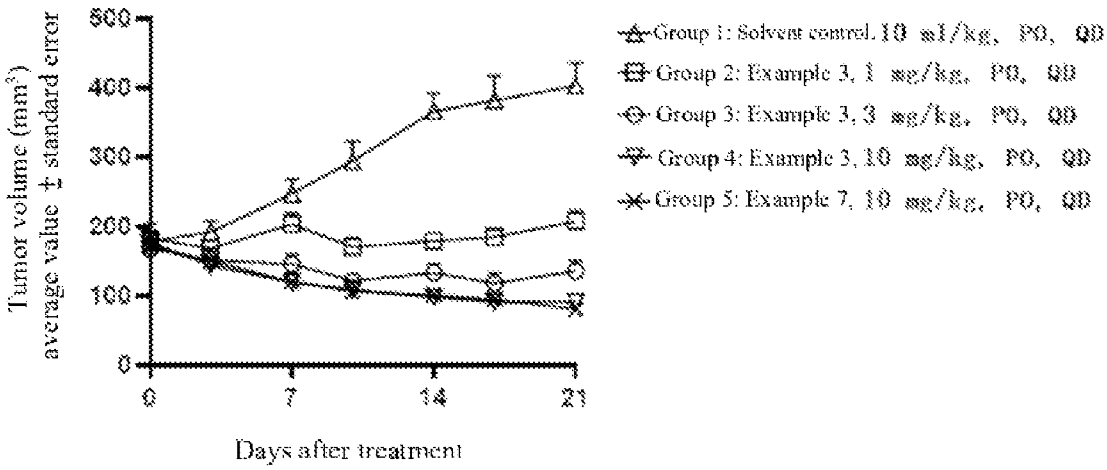
FIG. 2 is a tumor growth curve diagram of the MCF-7 hypodermic tumor model in test example 9.
Figure 3:
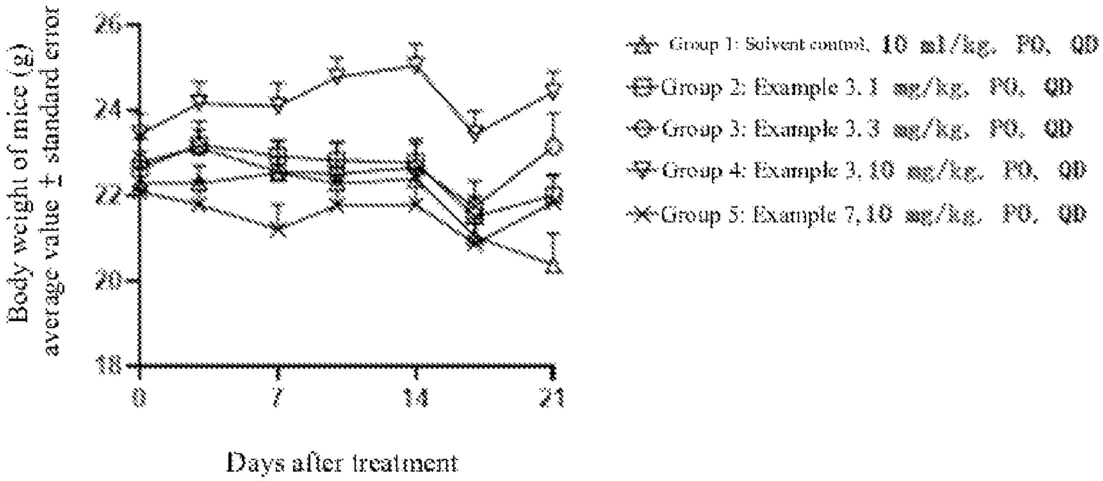
FIG. 3 is a body weight change diagram of MCF-7 hypodermic tumor model in animals in test example 9.

Experimental Results see Table 9, FIG. 2 and FIG. 3. In MCF-7 model of subcutaneous transplantation tumor in mice, the compound #Example 3 of the present invention has significant inhibitory effects (P<0.01) on tumor growth when it is administered orally once daily at 1 mg/kg, 3 mg/kg or 10 mg/kg and shows a good dose-response relationship. When administered at doses of 3 mg/kg and 10 mg/kg, the compound shows an effect of shrinking tumor. The compound #Example 3 of the present invention has significant inhibitory effects (P<0.01) on tumor growth when it is administered orally once daily at 10 mg/kg and shows an effect of shrinking tumor. The compound #Example 3 and Example 7 do not significantly affect the body weight of mice at the doses tried.

TABLE 9

Tumor volume of MCF-7 subcutaneous tumor model

| Test compounds | Dosage mg/kg | Mode of adminis-tration | Frequency of adminis-tration | Average tumor volume ($mm^3$) Day 0 | Day 21 | TGI (%) |
|---|---|---|---|---|---|---|
| Solvent control | / | PO | QD | 179 | 403 | / |
| Example 3 | 1 | PO | QD | 183 | 207 | 89.08 |
| Example 3 | 3 | PO | QD | 169 | 136 | 114.71 |
| Example 3 | 10 | PO | QD | 177 | 91 | 138.17 |
| Example 7 | 10 | PO | QD | 170 | 80 | 140.09 |

Test Example 10: Growth Inhibition Experiment of the Compounds of the Present Invention in MCF-7 Intracranial Tumor Model in Mice

Experimental Reagents/Instruments

Human breast cancer MCF-7 cells: ATCC, HTB-22
17β-estradiol tablets: Innovative Research of America, Cat No.: SE-121, 60-day release, 0.72 mg/pellet
EMEM medium: ATCC, Cat No.: 30-2003
Fetal bovine serum: Gibco, Cat. No.: 1099-141C
Penicillin (Pen Strep): Gibco, Cat No.: 15240-122
Recombinant human insulin: Shanghai Yeasen Biotechnology Co., Ltd., Cat. No.: 40112ES60
0.25% trypsin-EDTA: Gibco, Cat No.: 25200-072
Stereotaxic apparatus: RWD Life Technology Co., Ltd., Cat No.: Standard/Digital/Single Arm/Mouse/68055
Micro-injection pump: KDS, Cat No.: Legato130
Miniature handheld cranial drill: RWD Life Technology Co., Ltd., Cat No.: 78001

Experimental Method

Animal information: NPG mice (female, 6-8 weeks, body weight: about 17-29 g) were purchased from Beijing Vitalstar Biotechnology Co., Ltd. The mice were fed in SPF environment and each cage position was individually ventilated. All animals had free access to standard certified commercial laboratory food and water.

Cell culture: The human breast cancer MCF-7 cell line was cultured in vitro in EMEM (cell culture medium) supplemented with 10% fetal bovine serum, 1% Pen Strep and 10 g/ml recombinant human insulin in a 37° C., 5% $CO_2$ incubator. Conventional digestion treatment with 0.25% trypsin-EDTA digestion solution was carried out twice weekly for passage. When the cell saturation was 80%-90%, and the number reached the requirement, the cells were collected and counted.

Cell inoculation: 15 μl/(containing 2×10$^6$) MCF-7 cell suspension was inoculated into the brain of mice using a stereotaxic apparatus, a micro-injection pump and a miniature handheld cranial drill, and the mice were subcutaneously inoculated with 170-estradiol tablets three days before the cell inoculation. On day 8 after cell inoculation, the mice were randomized into groups for administration according to the body weight thereof, and the day of grouping was Day 0.

Administration: Fulvestrant (AstraZeneca) was administered at a dose of 250 mg/kg by subcutaneous injection (SC), once weekly (QW), and the compound #Example 3 was administered at a dose of 30 mg/kg, orally (PO), once daily (QD). 11 mice were in the vehicle group and 8 mice were in the administration group. Mice in all groups were continuously administered until the mice died, which were euthanized due to poor state or the end of the experiment.

Experiment Observation and Endpoint

The body weight of the mice was measured twice weekly, and the survival status of the mice was observed.

At the end of the experiment on Day 48, all mice were euthanized.

Figure 4:
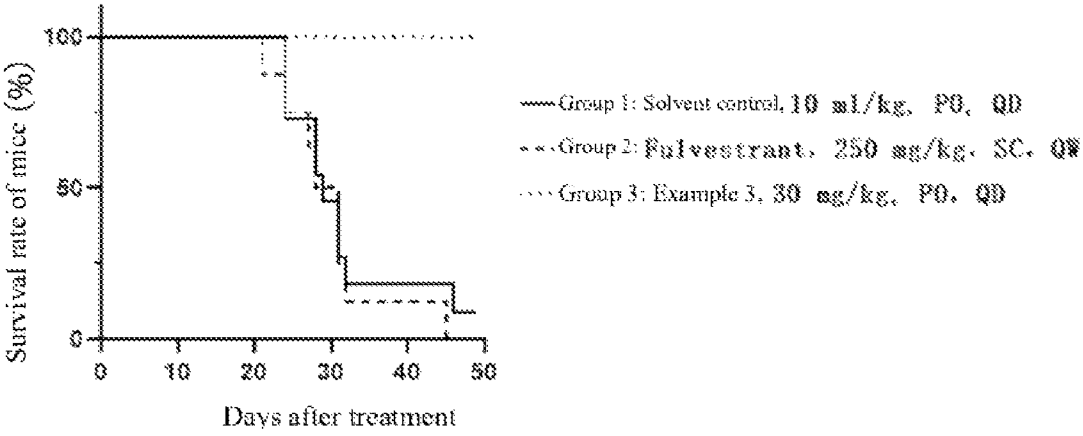
FIG. 4 is a survival curve diagram of MCF-7 intracranial model in mice in test example 10.
Figure 5:
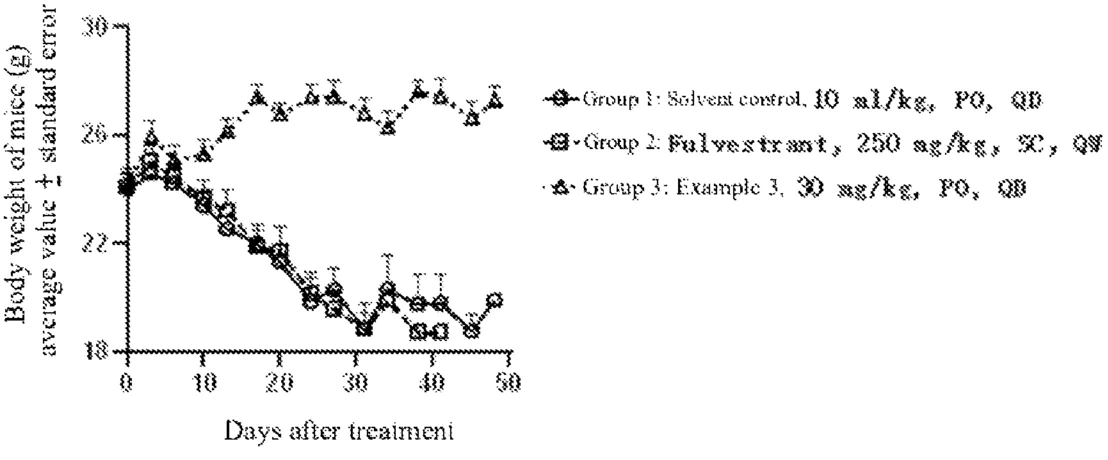
FIG. 5 is a body weight change diagram of MCF-7 intracranial model in mice in test example 10.

Experimental Results see FIG. 4 and FIG. 5. In the MCF-7 intracranial tumor model in mice, the mice in Fulvestrant group (250 mg/kg subcutaneously administered once weekly) continued to lose weight, and the survival status of the mice was not significantly different from that of the solvent control group (median survival period, 29 days for solvent control group, 29.5 days for Fulvestrant group). The mice in the group of the compound #Example 3 of the present invention (30 mg/kg orally administered once daily) were stable in body weight and had no abnormality until the end of the experiment. No death case occurred in the mice in the group of example 3 compound of the present invention. Compared with the solvent control or Fulvestrant, the compound of example 3 has a significant inhibitory effect in MCF-7 intracranial tumor model in mice, and the survival period of the mice is significantly prolonged (P<0.01).

What is claimed is:

1. A compound as represented by formula (I), or a pharmaceutically acceptable salt thereof:

(I)

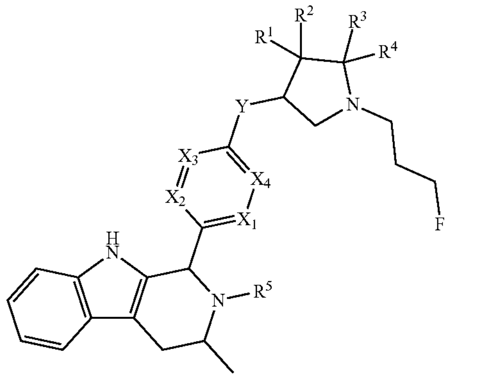

wherein $R^1$, $R^2$, $R^3$ and $R^4$ are independently selected from H, F, Cl, Br, I, CN, $C_1$-$C_6$alkyl, $C_1$-$C_6$alkoxy or $C_3$-$C_6$cycloalkyl;

the structure unit

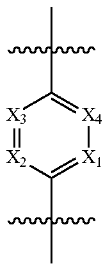

is

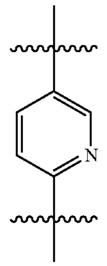

Y is selected from O or NH;

$R^5$ is independently selected from $C_1$-$C_6$alkyl, and the $C_1$-$C_6$alkyl is optionally substituted with $R^a$;

$R^a$ is selected from F, Cl, Br, I, OH, CN, $C_1$-$C_6$alkyl, $C_1$-$C_6$alkoxy or $C_3$-$C_6$cycloalkyl.

2. The compound as represented by formula (I) or the pharmaceutically acceptable salt thereof according to claim 1, wherein $R^1$, $R^2$, $R^3$ and $R^4$ are independently selected from H, F, Cl, Br, I, CN or $C_1$-$C_3$alkyl.

3. The compound as represented by formula (I) or the pharmaceutically acceptable salt thereof according to claim 1, wherein $R^5$ is selected from $C_1$-$C_3$alkyl, and the $C_1$-$C_3$alkyl is optionally substituted with $R^a$.

4. The compound as represented by formula (I) or the pharmaceutically acceptable salt thereof according to claim 1, wherein the structure unit

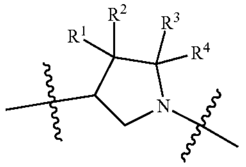

is selected from

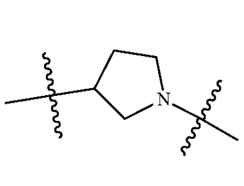
,
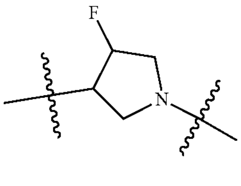
,

-continued

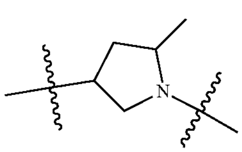 , 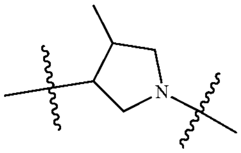 .

5. The compound as represented by formula (I) or the pharmaceutically acceptable salt thereof according to claim 1 is:

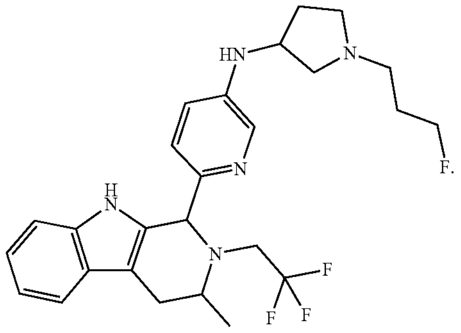 [SMILES: CC1Cc2c([nH]c3ccccc23)C(c2ccc(NC3CCN(CCCF)C3)cn2)N1CC(F)(F)F]

6. The compound as represented by formula (I) or the pharmaceutically acceptable salt thereof according to claim 1 is:

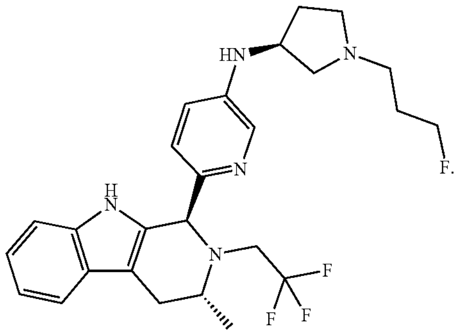 [SMILES: C[C@@H]1Cc2c([nH]c3ccccc23)[C@@H](c2ccc(N[C@H]3CCN(CCCF)C3)cn2)N1CC(F)(F)F]

7. A pharmaceutical composition, comprising the compound or the pharmaceutically acceptable salt thereof according to claim 1 and a pharmaceutically acceptable adjuvant.

8. A method for treating an estrogen receptor-related disease, ER-positive breast cancer comprising administering the compound or the pharmaceutically acceptable salt thereof according to claim 1 to a subject in need thereof.

9. The compound as represented by formula (I) or the pharmaceutically acceptable salt thereof according to claim 1, wherein the $R^a$ is selected from F, Cl, Br, I, OH or CN.

10. The compound as represented by formula (I) or the pharmaceutically acceptable salt thereof according to claim 1, wherein $R^5$ is selected from $CH_2CF_3$, $CH_2CHF_2$, $CH_2CF_2CH_2OH$ or $CH_2CF_2CH_2CN$.

11. The compound as represented by formula (I) or the pharmaceutically acceptable salt thereof according to claim 1 is:

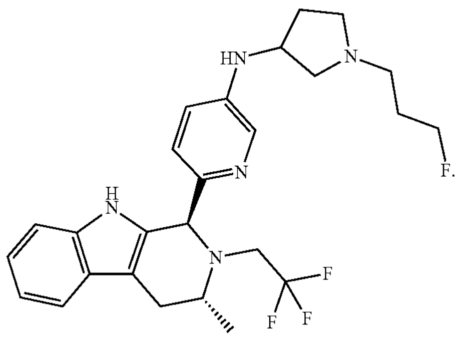 [SMILES: C[C@@H]1Cc2c([nH]c3ccccc23)[C@@H](c2ccc(NC3CCN(CCCF)C3)cn2)N1CC(F)(F)F]

12. The method according to claim 8, wherein the estrogen receptor-related disease is ER-positive breast cancer brain metastasis.

* * * * *